(12) United States Patent
Luttrull et al.

(10) Patent No.: US 10,953,241 B2
(45) Date of Patent: *Mar. 23, 2021

(54) PROCESS FOR PROVIDING PROTECTIVE THERAPY FOR BIOLOGICAL TISSUES OR FLUIDS

(71) Applicant: Ojai Retinal Technology, LLC, Ojai, CA (US)

(72) Inventors: Jeffrey K. Luttrull, Ojai, CA (US); Benjamin W. L. Margolis, Oakland, CA (US); David B. Chang, Tustin, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/583,096

(22) Filed: May 1, 2017

(65) Prior Publication Data

US 2017/0232269 A1    Aug. 17, 2017

Related U.S. Application Data

(63) Continuation-in-part of application No. 15/214,726, filed on Jul. 20, 2016, now Pat. No. 10,531,908, (Continued)

(51) Int. Cl.
*A61N 5/04* (2006.01)
*A61N 1/40* (2006.01)
(Continued)

(52) U.S. Cl.
CPC ............ *A61N 5/0625* (2013.01); *A61B 18/20* (2013.01); *A61F 9/00821* (2013.01); (Continued)

(58) Field of Classification Search
CPC combination set(s) only.
See application file for complete search history.

(56) References Cited

U.S. PATENT DOCUMENTS

| 3,408,593 A | 10/1968 | Hurwitz, Jr. |
| 4,048,011 A | 9/1977 | Kovin et al. |

(Continued)

FOREIGN PATENT DOCUMENTS

| DE | 10 2010 022 760 A1 | 12/2011 |
| WO | 2006/002949 A2 | 1/2006 |

(Continued)

OTHER PUBLICATIONS

Sramek et al. Non-damaging retinal phototherapy: dynamic range of heat shock protein expression. Invest Ophthalmol Vis Sci. Mar. 28, 2011;52(3):1780-7 (Year: 2011).*

(Continued)

*Primary Examiner* — Joseph A Stoklosa
*Assistant Examiner* — Adam J Avigan
(74) *Attorney, Agent, or Firm* — Kelly & Kelley, LLP

(57) ABSTRACT

A process that provides protective therapy for biological tissues or fluids includes applying a pulsed energy source to a target tissue or a target fluid having a chronic progressive disease or a risk of having a chronic progressive disease to therapeutically or prophylactically treat the target tissue or target fluid. The pulsed energy source has energy parameters selected so as to raise the target tissue or bodily target fluid temperature up to a predetermined temperature for a short period of time to achieve a therapeutic or prophylactic effect, while the average temperature rise of the target tissue or target fluid over a longer period of time is maintained at or below a predetermined level so as not to permanently damage the target tissue or target fluid.

20 Claims, 29 Drawing Sheets

Related U.S. Application Data which is a continuation-in-part of application No. 14/922,885, filed on Oct. 26, 2015, now Pat. No. 9,427,602, and a continuation-in-part of application No. 14/607,959, filed on Jan. 28, 2015, now Pat. No. 9,168,174, which is a continuation-in-part of application No. 13/798,523, filed on Mar. 13, 2013, now Pat. No. 10,219,947, which is a continuation-in-part of application No. 13/481,124, filed on May 25, 2012, now Pat. No. 9,381,115, application No. 15/583,096, which is a continuation-in-part of application No. 15/232,320, filed on Aug. 9, 2016, now Pat. No. 9,962,291, which is a continuation-in-part of application No. 15/148,842, filed on May 6, 2016, now Pat. No. 10,363,171, which is a continuation-in-part of application No. 14/921,890, filed on Oct. 23, 2015, now Pat. No. 9,381,116, which is a continuation-in-part of application No. 14/607,959, filed on Jan. 28, 2015, now Pat. No. 9,168,174.

(60) Provisional application No. 62/153,616, filed on Apr. 28, 2015.

(51) Int. Cl.

| | | |
|---|---|---|
| *A61N 5/067* | (2006.01) | |
| *A61B 18/00* | (2006.01) | |
| *A61B 18/18* | (2006.01) | |
| *A61N 2/02* | (2006.01) | |
| *A61N 5/06* | (2006.01) | |
| *A61N 5/02* | (2006.01) | |
| *A61B 18/20* | (2006.01) | |
| *A61N 7/00* | (2006.01) | |
| *A61B 18/22* | (2006.01) | |
| *A61F 9/008* | (2006.01) | |
| *A61N 7/02* | (2006.01) | |
| *A61B 17/00* | (2006.01) | |

(52) U.S. Cl.
CPC .............. *A61N 1/403* (2013.01); *A61N 2/02* (2013.01); *A61N 5/025* (2013.01); *A61N 5/045* (2013.01); *A61N 5/0603* (2013.01); *A61N 7/02* (2013.01); *A61B 18/1815* (2013.01); *A61B 18/22* (2013.01); *A61B 2017/00154* (2013.01); *A61B 2018/005* (2013.01); *A61B 2018/00494* (2013.01); *A61B 2018/00589* (2013.01); *A61B 2018/00726* (2013.01); *A61B 2018/00982* (2013.01); *A61B 2018/00994* (2013.01); *A61B 2018/20359* (2017.05); *A61F 9/00817* (2013.01); *A61F 2009/00863* (2013.01); *A61N 2005/063* (2013.01); *A61N 2005/0604* (2013.01); *A61N 2005/0607* (2013.01); *A61N 2005/067* (2013.01); *A61N 2005/0608* (2013.01); *A61N 2005/0609* (2013.01); *A61N 2005/0659* (2013.01); *A61N 2005/0662* (2013.01); *A61N 2007/0004* (2013.01); *A61N 2007/0043* (2013.01)

(56) References Cited

U.S. PATENT DOCUMENTS

| | | | |
|---|---|---|---|
| 4,176,325 | A | 11/1979 | Kajimura et al. |
| 4,194,114 | A | 3/1980 | Pankratov et al. |
| 4,410,365 | A | 10/1983 | Glukhovsky et al. |
| 4,556,051 | A * | 12/1985 | Maurer .................. A61N 2/02 600/14 |
| 4,695,733 | A | 9/1987 | Pesavento |
| 4,730,335 | A | 3/1988 | Clark et al. |
| 4,791,634 | A | 12/1988 | Miyake |
| 4,825,880 | A | 5/1989 | Stauffer et al. |
| 4,865,029 | A | 9/1989 | Pankratov et al. |
| 4,879,722 | A | 11/1989 | Dixon et al. |
| 4,930,504 | A | 6/1990 | Diamantopoulos et al. |
| 4,933,944 | A | 6/1990 | McGraw |
| 4,935,931 | A | 6/1990 | McGraw |
| 4,961,079 | A | 10/1990 | Owens et al. |
| 4,967,416 | A | 10/1990 | Esterowitz et al. |
| 5,037,421 | A | 8/1991 | Boutacoff et al. |
| 5,067,951 | A | 11/1991 | Greve |
| 5,085,492 | A | 2/1992 | Kelsoe et al. |
| 5,088,803 | A | 2/1992 | Buzawa |
| 5,147,354 | A | 9/1992 | Boutacoff et al. |
| 5,372,595 | A | 12/1994 | Gaasterland et al. |
| 5,394,199 | A | 2/1995 | Flower |
| 5,430,756 | A | 7/1995 | Hanihara |
| 5,520,680 | A | 5/1996 | Shapshay et al. |
| 5,651,019 | A | 7/1997 | Goldberg et al. |
| 5,982,789 | A | 11/1999 | Marshall et al. |
| 6,047,216 | A | 4/2000 | Carl et al. |
| 6,050,990 | A | 4/2000 | Tankovich et al. |
| 6,066,128 | A | 5/2000 | Bahmanyar et al. |
| 6,129,722 | A | 10/2000 | Ruiz |
| 6,156,028 | A | 12/2000 | Prescott |
| 6,208,769 | B1 | 3/2001 | Pankratov |
| 6,222,869 | B1 | 4/2001 | Marshall et al. |
| 6,259,952 | B1 | 7/2001 | Sluijter et al. |
| 6,327,291 | B1 | 12/2001 | Marshall |
| 6,377,599 | B1 | 4/2002 | Marshall |
| 6,540,391 | B2 | 4/2003 | Lanzetta et al. |
| 6,681,185 | B1 | 1/2004 | Young et al. |
| 6,715,877 | B2 | 4/2004 | Molebny |
| 6,733,490 | B1 | 5/2004 | Falsini et al. |
| 6,813,942 | B1 | 11/2004 | Vozhdaev et al. |
| 6,889,695 | B2 | 5/2005 | Pankratov et al. |
| 6,942,655 | B2 | 9/2005 | Peyman |
| 7,227,196 | B2 | 6/2007 | Burgener, II et al. |
| 7,229,435 | B2 | 6/2007 | Nakamura |
| 7,387,785 | B1 | 6/2008 | Rudin et al. |
| 7,452,081 | B2 | 11/2008 | Wiltberger et al. |
| 7,645,276 | B2 | 1/2010 | Pankratov et al. |
| 7,763,828 | B2 | 7/2010 | Talwar et al. |
| 7,766,903 | B2 | 8/2010 | Blumenkranz et al. |
| 7,766,904 | B2 | 8/2010 | McGowan, Sr. et al. |
| 7,771,417 | B2 | 8/2010 | Telfair et al. |
| 7,909,816 | B2 | 3/2011 | Buzawa |
| 8,454,161 | B2 | 6/2013 | Su et al. |
| 9,333,371 | B2 | 5/2016 | Bean et al. |
| 9,427,602 | B2 * | 8/2016 | Luttrull .............. A61F 9/00821 |
| 2002/0099363 | A1 | 7/2002 | Woodward et al. |
| 2002/0120255 | A1 | 8/2002 | Sotiropoulos et al. |
| 2002/0165525 | A1 | 11/2002 | Nakamura |
| 2003/0078567 | A1 | 4/2003 | Dorin et al. |
| 2004/0098070 | A1 | 5/2004 | Mohr et al. |
| 2005/0069531 | A1 | 3/2005 | Karageozian et al. |
| 2005/0176662 | A1 | 8/2005 | Inana et al. |
| 2007/0173793 | A1 | 7/2007 | Rathjen |
| 2007/0213693 | A1 | 9/2007 | Plunkett |
| 2008/0015553 | A1 | 1/2008 | Zacharias |
| 2008/0076958 | A1 | 3/2008 | Britva et al. |
| 2009/0093798 | A1 | 4/2009 | Charles |
| 2009/0276019 | A1 | 11/2009 | Perez et al. |
| 2010/0049180 | A1 * | 2/2010 | Wells .................. A61N 5/0616 606/12 |
| 2010/0068141 | A1 | 3/2010 | Kaushal et al. |
| 2010/0082024 | A1 | 4/2010 | Brannan et al. |
| 2010/0100162 | A1 | 4/2010 | Peyman |
| 2010/0152716 | A1 | 6/2010 | Previn et al. |
| 2010/0168724 | A1 | 7/2010 | Sramek et al. |
| 2010/0249760 | A1 | 9/2010 | Blumenkranz et al. |
| 2010/0290007 | A1 | 11/2010 | Van de Velde |
| 2011/0196350 | A1 | 8/2011 | Friedman et al. |
| 2013/0110095 | A1 | 5/2013 | Boxer Wachler |
| 2013/0116672 | A1 * | 5/2013 | Yee .................... A61F 9/00821 606/4 |
| 2013/0231721 | A1 | 9/2013 | DeCharms |
| 2013/0317487 | A1 | 11/2013 | Luttrull et al. |

(56) References Cited

U.S. PATENT DOCUMENTS

| | | |
|---|---|---|
| 2013/0317570 A1 | 11/2013 | Luttrull et al. |
| 2014/0121631 A1 | 5/2014 | Bean et al. |
| 2014/0228824 A1 | 8/2014 | Yee et al. |
| 2014/0364924 A1 | 12/2014 | Dunleavy et al. |
| 2015/0058204 A1 | 2/2015 | Dunleavy et al. |
| 2015/0217125 A1 | 8/2015 | Chornenky et al. |
| 2016/0082294 A1 | 3/2016 | Luttrull et al. |
| 2016/0220834 A1 | 8/2016 | Schwarz |
| 2016/0346126 A1 | 12/2016 | Luttrull et al. |
| 2017/0232269 A1 | 8/2017 | Luttrull et al. |
| 2017/0319383 A1 | 11/2017 | Luttrull et al. |

FOREIGN PATENT DOCUMENTS

| | | |
|---|---|---|
| WO | 2006005038 A2 | 1/2006 |
| WO | 2007035855 A2 | 3/2007 |
| WO | 2007106521 A2 | 9/2007 |
| WO | 2011/050056 A2 | 4/2011 |
| WO | 2012/018385 A2 | 2/2012 |

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Luttrull et al. Subthreshold diode micropulse panretinal photocoagulation for proliferative diabetic retinopathy. Eye (2007), 1-6 © 2007 Nature Publishing Group, www.nature.com/eye.

Small Beam Diameter Scanning Galvo Mirror Systems; Thorlabs; 1999-2013, 4 pgs.

Keller, Matthew D. et al.; Raman Spectroscopy for Cancer Diagnosis; www.spectroscopyonline.com; Nov. 2006 21(11); pp. 33-41 (including Reference (21) thereof).

International Search Report for PCT/US2015/0060836 dated Jan. 29, 2016.

Allingham RR, Damji KF, Freedman S, et al. Shields Textbook of Glaucoma, 6th Ed., 2010, Wolters Kluwer / Lippincott Williams & Wilkins, Philadelphia. ISBN-13: 978-0-7817-9585-2.

Danesh-Meyer HV, Levin LA. Glaucoma as a neurodegenerative disease. J Neuroophthalmol. Sep. 2015; 35 Suppl 1: S22-8.

Tian K, Shibata-Germanos S, Pahlitzsch M, Cordeiro MF. Current perspective of neuroprotection and glaucoma. Clin Ophthalmol. Nov. 11, 2015; 9: 2109-18.

Vujosevic S, Boffega E, Casciano M, et al. Microperimetry and fundus autofluorescence in diabetic macular edema. Subthreshold micropulse diode laser versus modified Early Treatment Diabetic Retinopathy Study Laser photocoagulation. Retina 2010; 30:908-16.

Lavinsky D, Cardillo JA, Melo, et al. Randomized clinical trial evaluating mETDRS versus normal or high-density micropulsephotocoagulation for diabetic macular edema. Invest Ophthalmol Vis Sci. Jun. 17, 2011; 52 (7): 4314-23.

Luttrull JK, Spink CJ, Musch DA. Subthreshold diode micropulse panretinal photocoagulation for proliferative diabetic retinopathy. Eye, May 2008; 22 (5): 607-12.

Luttrull JK, Sramek C, Palanker D, Spink CJ, Musch DC. Long-term safety, high-resolution imaging, and tissue temperature modeling of subvisible diode micropulse photocoagulation for retinovascular macular edema. Retina 2012; 32 (2): 375-86.

Malik KJ1, Sampat KM, Mansouri A, Steiner JN, Glaser BM. Low-intensity/high-density subthreshold microPulse diode laser for chronic central serous chorioretinopathy. Retina. Mar. 2015;35(3):532-6.

Luttrull, JK. Subthreshold diode micropulse laser (SDM) for central serous chorioretinopathy. Retina, Jan. 2016 (in press).

Luttrull JK, Dorin G. Subthreshold diode micropulse photocoagulation as invisible retinal phototherapy for diabetic macular edema. A review. Current Diabetes Reviews, 2012, 8, 274-284.

Luttrull JK, Chang DB, Margolis BWL, Darin G, Luttrull DK. Laser re-sensitization of medically unresponsive neovascular age-related macular degeneration: Efficacy and implications. Retina Jun. 2015; 35(6): 1184-1194.

Luttrull JK, Margolis BWL. Functionally guided retinal protective therapy as prophylaxis for age-related and inherited retinal degenerations. A pilot study. Invest Ophthalmol Vis Sci. Jan. 1, 2016;57(1):265-75. doi: 10.1167/iovs.15-18163.

McCulloch DL, Marmor MF, Brigell MG, et al. ISCEV Standard for full-field clinical electroretinography (2015 update). Doc Ophthalmol. Feb. 2015; 130 (1): 1-12.

Porciatti V, Ventura LM. Normative Data for a User-friendly Paradigm for Pattern Electroretinogram Recording. Ophthalmology, 2004; 111(1): 161-168.

Gutstein W, Sinclair SH, Presti P, North RV. Interactive thresholding of central acuity under contrast and luminance conditions mimicking real world environments: 1. Evaluation against LogMAR charts. J Comput Sci Sys Bio, 20125; 8 (4) 225-232.

Parisi V, Centofanti M, Ziccardi L, et al. Treatment with citicoline drops enhances retinal function and neural conduction along the visual pathways in open angle glaucoma. Graefes Arch Clin Exp Ophthamol, May 2015; DOI 10.1007/s00417-015-3044-9.

Miller NR, ed. Walsh and Hoyt's Clinical Neurophthalmology. 4th Ed, 1985; Chapter 3: 41-60.Williams and Wilkins, Baltimore Maryland.

Salomão SR, Berezovsky A, Andrade RE, et al. Visual electrophysiologic findings in patients from an extensive Brazilian family with Leber'shereditary optic neuropathy. Doc Ophthalmol. Mar. 2004;108(2):147-55.

Kolomeyer AM, Zarbin MA. Trophic factors in the pathogenesis and therapy for retinal degenerative diseases. Surv Ophthalmol. Mar.-Apr. 2014;59 (2):134-65.

Kenealey J, Subramanian P, Comitato A, et al. Small Retinoprotective Peptides Reveal a Receptor-binding Region on Pigment Epithelium-derived Factor. J Biol Chem. Oct. 16, 2015;290(42):25241-53.

Yu PK1, Cringle SJ, McAllister IL, Yu DY. Low power laser treatment of the retina ameliorates neovascularisation in a transgenic mouse model of retinalneovascularisation. Exp Eye Res. Nov. 2009;89(5):791-800.

Flaxel C1, Bradle J, Acott T, Samples JR. Retinal pigment epithelium produces matrix metalloproteinases after laser treatment. Retina. Jun. 2007;27 (5):629-34.

Sramek C, Mackanos M, Spitler R, et al. Non-damaging retinal phototherapy: dynamic range of heat shock protein expression. Invest Ophthalmol Vis Sci. Mar. 28, 2011; 52 (3):1780-7.

Ventura LM, Feuer WJ, Porciatti V. Progressive loss of retinal ganglion cell function is hindered with IOP-lowering treatment in early glaucoma. IOVS, Feb. 2012 53 (2): 659-663.

Ventura LM, Porciafti V. Restoration of retinal ganglion cell function in early glaucoma after intraocular pressure reduction. A pilot study. Ophthalmology 2005, 112 (1): 20-27.

Yap GH, Chen LY, Png R, et al. Clinical value of electrophysiology in determining the diagnosis of visual dysfunction in neuro-ophthalmology patients. Doc Ophthalmol. Dec. 2015;131(3):189-96.

Waisbourd M, Ahmed OM, Molineaux J, et al. Reversible structural and functional changes after intraocular pressure reduction in patients with glaucoma. Graefes Arch Clin Exp Ophthalmol. Mar. 19, 2016. [Epub ahead of print] PMID: 26995555.

(56) References Cited

OTHER PUBLICATIONS

Banitt MR, Ventura LM, Feuer WJ, Savatovsky E, et al. Progressive loss of retinal ganglion cell function precedes structural loss by several years in glaucoma suspects. IOVS, Mar. 2013; 54 (3): 2346-2352.

Karu T. Photobiology of low-power laser effects. Review. Health Phys. May 1989; 56 (5): 691-704.

Gao X, Xing D. Molecular mechanisms of cell proliferation induced by low power laser irradiation. J Biomed Sci. Jan. 12, 2009;16:4.

Dorin G, Luttrull JK, Samples JR. Chapter 21: Laser alteration of collector channel ostia. Pivotal paradigm shift from photocoagulation to photostimulation. Glaucoma Research and Clinical Advances: 2016 to 2018. Knepper and Samples, Eds. Kugler Pub. Jan. 1, 2016, Amsterdam, Netherlands. ISBN: 9789062992478.

Van Teijlingen ER1, Rennie AM, Hundley V, Graham W. The importance of conducting and reporting pilot studies: the example of the Scottish Births Survey. J Adv Nurs. May 2001; 34 (3): 289-95.

Luttrull JK, Sinclair SH. Safety of transfoveal subthreshold diode micropulse laser (SDM) for fovea-involving diabetic macular edema in eyes with good visual acuity. Retina. Oct. 2014; 34 (10): 2010-20.

Luttrull, JK and Margolis BWL. improved retinal function following SDM laser for chronic disease. American Society of Retina Specialists Annual Meeting Vienna, Austria. Jul. 11, 2015 [online]. [retrieved on Jan. 11, 2017] <URL: http://www.diopsys.com/wp-content/uploads/2015/07/Luttrutl_Improved-retinal-function-following-SDM-laser-for-chronic-disease_ASRS2015.pdf>.

International Search Report for the International application No. PCT/US2016/46043 dated Dec. 27, 2016.

International Search Report for International Application No. PCT/US2016/62421 dated Feb. 7, 2017.

International Search Report for the International Application No. PCT/US2017/064708, dated Feb. 9, 2018.

International Search Report for International Application No. PCT/US2017/044319, dated Jan. 11, 2018.

International Search Report for the International Application No. PCT/US2018/22201, dated Jun. 1, 2018.

* cited by examiner

PROCESS FOR PROVIDING PROTECTIVE THERAPY FOR BIOLOGICAL TISSUES OR FLUIDS

RELATED APPLICATIONS

This application is a continuation-in-part of U.S. application Ser. No. 15/214,726 filed on Jul. 20, 2016, which is a continuation-in-part of U.S. application Ser. No. 14/922,885 filed on Oct. 26, 2015 (now U.S. Pat. No. 9,427,602) (which claims priority from U.S. Provisional Application No. 62/153,616 filed on Apr. 28, 2015), which is a continuation-in-part of U.S. application Ser. No. 14/607,959 filed on Jan. 28, 2015 (now U.S. Pat. No. 9,168,174), which is a continuation-in-part of U.S. application Ser. No. 13/798,523 filed on Mar. 13, 2013, which is a continuation-in-part of U.S. application Ser. No. 13/481,124 filed on May 25, 2012 (now U.S. Pat. No. 9,381,115). This application is also a continuation-in-part of U.S. application Ser. No. 15/232,320 filed on Aug. 9, 2016, which is a continuation-in-part of U.S. application Ser. No. 15/188,608 filed Jun. 21, 2016, which is a continuation-in-part of U.S. application Ser. No. 15/148,842 filed on May 6, 2016, which is a continuation-in-part of U.S. application Ser. No. 14/921,890 filed Oct. 23, 2015 (now U.S. Pat. No. 9,381,116), which is a continuation-in-part of U.S. application Ser. No. 14/607,959 filed Jan. 28, 2015 (now U.S. Pat. No. 9,168,174).

BACKGROUND OF THE INVENTION

The present invention generally relates to processes for treating biological tissues or fluids. More particularly, the present invention relates to a process for providing protective therapy for biological tissues or fluids having a chronic progressive disease, or a risk for a chronic progressive disease.

Chronic progressive diseases (CPDs) currently, and increasingly in the future, are healthcare challenges. There are many such CPDs, including Type II Diabetes, Alzheimer's Disease, Idiopathic Pulmonary Fibrosis (IPF), heart disease and the like. There are many diseases for which the underlying cause is unknown, and which either have no treatment or suboptimal treatment. Some of these diseases are either uniformly terminal in short-order, or constitute major public health problems due to epidemic increase.

These diseases are both chronic and progressive. Chronic progressive diseases may have any number of underlying causes, including infectious, genetic, multi-factorial and immune. While there are many different causes of CPDs, they share fundamental commonalities. A unifying feature of all CPDs is the accumulation of abnormal intracellular proteins. Another common feature of all CPDs is increasing cellular and organ dysfunction, leading to failure. Yet another common and unifying feature of CPDs is cellular and organ dysfunction that causes and promotes chronic inflammation. These features of all CPDs is a vicious cycle leading to the disease worsening over time.

Thus, interruption of the cycle is essential to ameliorate the course of the disease. One approach to treatment of CPDs is gene therapy, which requires identification and repair or replacement of the defective gene that is the cause of the disease. However, for some CPDs, the gene defect is unknown. For others, there may be many potential gene defects which lead to the same disease. For example, retinitis pigmentosa can be caused by any of over 150 different genetic defects. This potential multiplicity of underlying defects makes gene therapy difficult.

Another approach to treatment of CPDs is drug therapy which typically attempts to target specific cellular proteins thought to be critical to the disease process to either inhibit or enhance their action. However, as there are an estimated 2,000 different protein types in the typical cell having $10^{680}$ potential interactions, successful, clinically effective without unacceptable side effects of targeted drug therapy is difficult.

Another approach to treatment of CPDs is non-specific and anti-inflammatory treatments. These include various steroidal and non-steroidal anti-inflammatory agents and immunosuppressive drugs. However, anti-inflammatory drugs have many drawbacks in CPDs. As they do not address the underlying cause of the disease, they must be used long-term and have limited effectiveness. Because of their modes of action and necessity of long-term use, the side effects and complications of treatment limit their usefulness. Immunosuppressive drugs have the same limitations as anti-inflammatory drugs. However, as they alter the normal function of the immune system apart from the disease process, they can cause further complications including other disease syndromes and neoplasia. Radiation therapy, such as using x-ray radiation, is another treatment for CPDs. It has effects similar to using anti-inflammatory and immunosuppressive drugs. However, it can also present more problematic side effects that worsen with time even after cessation of treatment, often making it unacceptable if long-term survival is anticipated.

Yet another, newer, approach to treatment of CPDs is identification and inhibitor of manager proteins. Such manager protein therapy attempts to address the problems presented by gene, drug, and anti-inflammatory/immunosuppression therapy by finding proteins or enzymes which are both key and common to several disease states, regardless of the underlying cause, and inhibiting them in various ways. As a single manager protein may be central to the development of a number of disease conditions, such as various and otherwise unrelated cancers, blocking this key protein could have wider therapeutic application than more disease-targeted therapies. However, manager protein therapy shares the general limitation of targeted drug therapy if the protein itself is targeted, with the additional problem of triggering compensatory mechanisms such as up-regulation leading to permanent insensitivity to a drug action. Moreover, manager protein therapy shares the general limitations of gene therapy if the transcriptional and translational mechanisms that produce the protein are targeted. Such manager protein therapy also shares the problems targeted drug therapy has, as mentioned above.

Stem cell transplantation (SCT) is yet another approach to treatment of CPDs. SCT attempts to replace dead or dysfunctional tissue with new functional tissue by transplanting stem cells into the tissue or area surrounding the tissue. SCT is highly complex and expensive, with significant risks and adverse treatment effects. Despite much public interest, SCT has been thus far ineffective.

The current approaches described above for treatment of CPDs are of limited success and usefulness and thus most CPDs have either no treatment currently or only palliative or ineffectual treatment. These treatments are of limited success and usefulness by virtue of practical limitations, including unknown or multiple causes, cost, time, as well as non-physiologic (being unnatural and artificial) modes of action, which by definition, impose a new drug-induced disease state overlying the CPD. In light of this, the ideal treatment for CPDs would be independent of the underlying cause, physiologic, and thus both effective and well tolerated without side-effects, and able to break the vicious CPD cycle by intervening at multiple points in the cycle including immediately distal to the primary defect for maximum effectiveness. The present invention fulfills these needs, and provides other related advantages.

SUMMARY OF THE INVENTION

The present invention is generally directed to a process for providing protective therapy for biological tissues or fluids which have a chronic progressive disease or a risk for chronic progressive disease. The present invention applies a pulsed energy source to a biological tissue or fluid which raises the temperature of the targeted tissue or targeted fluid and stimulates activation of heat shock proteins, which facilitate protein repair without damaging the tissue.

In accordance with the present invention, a pulsed energy source is provided having energy parameters including wavelength or frequency, duty cycle and pulse train duration. The pulsed energy source may comprise laser light, microwave, radiofrequency or ultrasound. The energy parameters are selected so as to raise the target tissue or bodily target fluid temperature up to 11° C., typically between 6° C. to 11° C. at least during the application of the pulsed energy source to the target tissue or target fluid, to achieve a therapeutic or prophylactic effect. The average temperature rise of the tissue or target fluid over several minutes is maintained at or below a predetermined level so as to not permanently damage the target tissue or target fluid. For example, the average temperature rise of the target tissue or target fluid over several minutes may be maintained at 6° C. or less. More often, the average temperature rise of the target tissue or target fluid is maintained at approximately 1° C. or less over several minutes, such as over a six-minute period of time.

The pulsed energy source may comprise a radiofrequency. The radiofrequency is typically between 3-6 megahertz (MHz), and has a duty cycle of between 2.5% to 5%, and a pulse train duration between 0.2 to 0.4 seconds. The radiofrequency may be generated with a device having a coil radii between 2 and 6 mm and between 13 and 57 amp turns.

When the pulsed energy source comprises a microwave frequency, the frequency is typically between 10 to 20 gigahertz (GHz), a pulse train duration between 0.2 and 0.6 seconds, and a duty cycle between 2% and 5%. The microwave may have an average power between 8 and 52 watts.

When the pulsed energy source is a pulsed light beam, the light beam may have a wavelength of between 530 nm to 1300 nm, a duty cycle of less than 10% and a pulse train duration between 0.1 and 0.6 seconds. The pulsed light beam preferably has a wavelength of between 800 nm and 1000 nm, and a power between 0.5 and 74 watts.

When the pulsed energy source comprises pulsed ultrasound, it typically has a frequency between 1 MHz and 5 MHz, a train duration between 0.1 and 0.5 seconds and a duty cycle between 2% to 10%. The ultrasound may have a power between 0.46 and 28.6 watts.

It may be determined that the target tissue or target fluid has a chronic progressive disease or is at risk of having a chronic progressive disease. The pulsed energy source is applied to the target tissue or target fluid having the chronic progressive disease or risk of having a chronic progressive disease to therapeutically or prophylactically treat the target tissue or target fluid. The pulsed energy source energy parameters may be selected so that 20 to 40 joules of energy is absorbed by each cubic centimeter of the target tissue or target fluid. The pulsed energy may be applied by inserting a device into a cavity of a body to apply the pulsed energy source to the target tissue or target fluid. Alternatively, or additionally, the pulsed energy source is directed to an exterior of a body which is adjacent to the target tissue or has a target bodily fluid supply close to the surface of the exterior of the body. The pulsed energy source may be applied to a plurality of target tissue areas. Adjacent target tissue areas are separated by at least a predetermined distance to avoid thermal tissue damage.

It is believed that the process of the present invention by selectively and controllably raising the target tissue or fluid temperature up to a predetermined temperature range over a short period of time, while maintaining the average temperature rise of the tissue at a predetermined temperature over a longer period of time, provides beneficial effects. These effects may be caused by inducing a heat shock response in order to increase the number or activity of heat shock proteins in body tissue or fluid in response to infection or other abnormalities. The present invention performs this in a controlled manner in order not to damage or destroy the tissue, fluid or the area of the body being treated.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
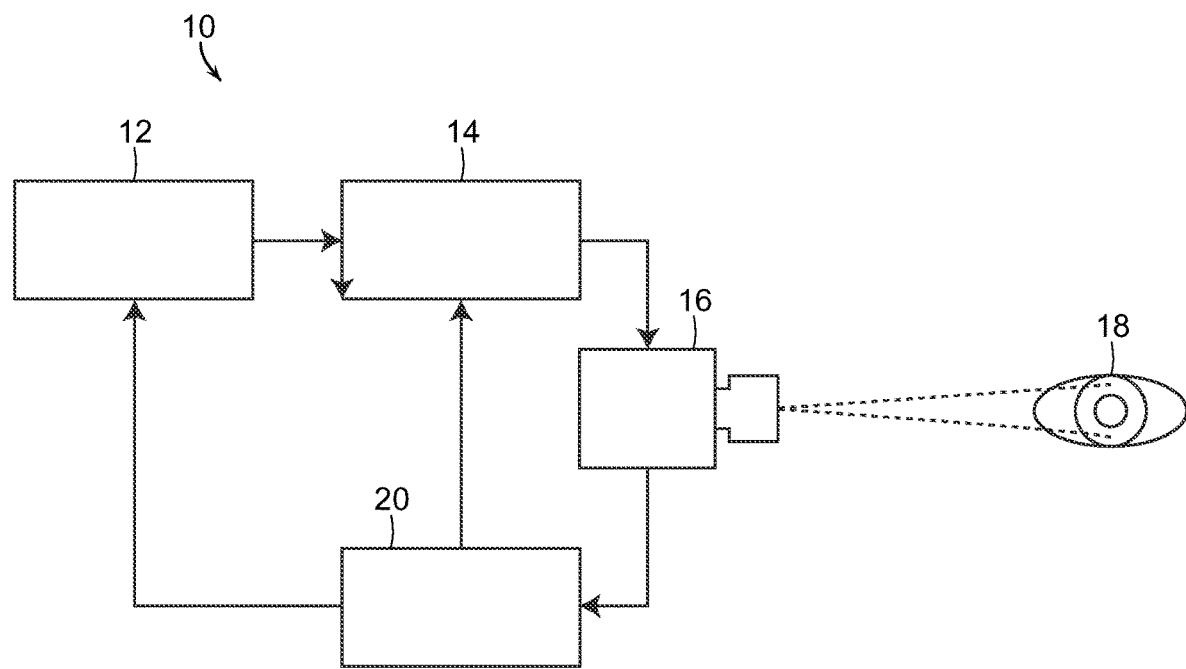
FIG. 1 is a diagrammatic view illustrating a system used to generate a pulsed energy source in the form of a laser light beam, in accordance with the present invention.

The present invention, as more fully described and illustrated herein, resides in processes and systems that provides protective therapy for biological tissues or fluids having a chronic progressive disease or at a risk of having a chronic progressive disease. In accordance with the invention, a pulsed energy source having energy parameters including wavelength or frequency, duty cycle and pulse train duration selected so as to raise a target tissue or bodily target fluid temperature up to eleven degrees Celsius for a short period of time of seconds or less, while maintaining an average temperature rise of the tissue or target fluid over several minutes at or below a predetermined level so as not to permanently damage the target tissue or target fluid. The pulsed energy source is applied to the target tissue or target fluid which is either determined to have a chronic progressive disease or at a risk of having a chronic progressive disease. This determination may be made before imaging, serologic, immunologic, or other abnormalities are detectable and may be done prophylactically. The determination may be accomplished by ascertaining if the patient is at risk for the chronic progressive disease. Alternatively, or additionally, results of an examination or test of the patient may be abnormal. A specific test, such as a genetic test, may be conducted to establish that the patient has a risk for the chronic progressive disease.

It is believed that a mechanism by which the invention is able to therapeutically or prophylactically treat the biological tissue or fluid is by stimulating heat shock protein activation in a target tissue or target fluid. Heat shock proteins (HSPs) are ubiquitous in highly conserved families of enzymes present in all cells of all creatures. This may account for as much as 40% of all proteins present in a given cell. HSPs are active and essential in maintenance of normal cell function and homeostasis. HSPs have many critical functions, one of which is to protect the cell from lethal injury of any kind and repair sublethal injuries.

While chronic inflammation is pathologic and destructive, acute inflammation can be reparative. Acute inflammation may occur in response to an acute injury. Common injuries requiring repair are typically associated with cellular and tissue damage, such as a wound. Depending upon the severity of injury and the functional sensitivity of the tissue, loss of key functions may result despite wound repair. Incomplete repair or continued or repeated injury may lead to chronic inflammation, as in CPDs.

The normal state of health of maintained by complex physiologic processes of constant surveillance for and repair of defective proteins and potential threats, such as bacteria, viruses and neoplasia. These normal physiologic processes and their actions are ideal as good health and function is the result of their normal function. While the normal function of these physiological processes are ideal, such homeostatic processes themselves are not always perfectively effective. Potential threats and abnormalities may either escape detection or exceed the ability for repair. Failure of surveillance and response may result from any number of reasons, including disease causing immunosuppression, evasion of detection by hiding of antigenic stimuli, such as occurring in certain cancers and retroviruses, and the onset and progression below the level of symptoms recognition and activation.

HSPs are the first step in the acute inflammatory process. Activation of HSPs by a threat initiates a cascade of subsequent events leading to improved cell function, reduced chronic inflammation, and reparative immunomodulation. The effective HSP activations preserve the life of the cell and normalize cell function, also referred to as homeotrophy. Sudden and severe stimuli are the most potent stimulators of homeotrophic HSP activation. Slowly progressive and chronic stimuli are not effective activators HSP response. Thus, CPDs do not stimulate a repairative response of the HSP activation. In some CPDs, like diabetes and Alzheimer disease, HSP function itself can become abnormal.

Typically, however, HSPs normalize cell function independent of the cause of abnormality by identifying and repairing abnormal cell proteins without regard to what made them abnormal, thus normalizing cell function. HSPs have an ability to restore every protein to its correct state or eliminate the irreparable, leading to replacement. As the HSP response is physiologic and thus perfect and without adverse effects, fixing what is broken without regard to the cause of the breakage, the repair response of HSPs is exactly tailored to the disease process. Homeotrophic HSP activation is thus a non-specific trigger of disease-specific repair.

The inventors have discovered that it is possible to stimulate HSP activation without cell or tissue damage by electromagnetic radiation-induced acute, but sublethal, cellular hyperthermy. In the absence of cell death or tissue damage, the cascade of physiologic repair and homeotrophy of the acute inflammatory response can thus be triggered without any adverse treatment effects. Acute inflammation incited without tissue damage may be thought of as "as if" acute inflammation. That is to say that homeotrophic cellular hyperthermy is able to elicit the acute inflammatory response that is entirely and only beneficial, "as if" it were caused by tissue damage, but in the absence of tissue damage. It has been found that the safest and most efficient stimulus of homeotrophic HSP activation is by pulsed electromagnetic radiation (PEMR). Pulsing allows significant increases in the abruptness and severity of the threat stimulus without killing the target cell to maximize HSP activation in the homeotrophic healing response. The various types of PEMR are best suited to different biological applications include light, laser, radio wave and microwave and ultrasound.

The eye is the most functionally sensitive organ in the body. There are a number of CPDs that effect the retina that share the typical characteristics of CPDs in general. Accordingly, CPDs of the retina may serve as a model for CPDs elsewhere in the body. Over many years of clinical experience in a large number of patients, it has been found that PEMR in the form of low-intensity/high-density subthreshold diode micropulsed laser treatment (SDM) has been shown to effectively treat, prevent, slow, reverse or stop the progression of every major chronic progressive disease of the retina, without regard to the cause. These include age-related, genetic, metabolic and diseases of unknown etiology of widely varying genotypes and phenotypes. Despite the thermal sensitivity of the retina, SDM does this without any known adverse treatment effects due to the selection of the operating parameters of the PEMR and thus is performed in complete safety.

With respect to conventional retinal photocoagulation, the physician must intentionally create retinal damage as a prerequisite to therapeutically effective treatment. However, the inventors surmised that the therapeutic alterations in the retinal pigment epithelium (RPE) cytokine production elicited by conventional photocoagulation comes from cells at the margins of traditional laser burns which were affected but not killed by the laser exposure. The inventors created energy parameters which created "true subthreshold photocoagulation", which is invisible and includes laser treatment non-discernable by any known means such as FFA, FAF, retrograde FAF, or even SD-OCT and produces absolutely no retinal damage detectable by any means at the time of treatment or any time thereafter by any known means of detection, but still yields the benefits of conventional retinal photocoagulation. This is discussed in U.S. Publication No. 2016/0346126 A1, the contents of which are hereby incorporated by reference.

Various parameters have been determined to achieve true subthreshold effective photocoagulation, including providing sufficient power to produce effective treatment but not too high to create tissue damage or destruction. It has been found that the intensity or power of a low duty cycle 810 nm laser beam between 100 watts to 590 watts per square centimeter is effective yet safe. A particularly preferred intensity or power of the laser light beam is approximately 250-350 watts per square centimeter for an 810 nm micropulsed diode laser.

Power limitations in current micropulsed diode lasers require fairly long exposure duration, although it is important that the generated heat be able to dissipate toward the unexposed tissue at the margins of the laser spot so as not to damage or destroy the cells or tissue. It has been found that a radiant beam of an 810 nm diode laser should have an exposure envelope of 500 milliseconds or less, and preferably approximately 100-300 milliseconds. If micropulsed diode lasers become more powerful, the exposure duration can be lessened accordingly. It has been found that invisible phototherapy or true subthreshold photocoagulation in accordance with the present invention can be performed at various laser light wavelengths, such as from a range of 532 nm to 1300 nm. Use of a different wavelength can impact the preferred intensity or power of the laser light beam and the exposure envelope duration in order that the retinal tissue is not damaged, yet therapeutic effect is achieved. Typically, the laser light pulse is less than a millisecond in duration, and typically between 50 microseconds to 100 microseconds in duration.

Another parameter of the present invention when utilizing laser light is the duty cycle, or the frequency of the train of micropulses or the length of the thermal relaxation time in between consecutive pulses. It has been found that the use of a 10% duty cycle or higher can increase the risk of lethal cell injury. Thus, duty cycles less than 10%, and preferably approximately 5% duty cycle or less are used as this parameter has been demonstrated to provide adequate thermal rise in treatment that remains below the level expected to produce lethal cell injury. The less the duty cycle, the longer the exposure envelope duration can be. For example, if the duty cycle is less than 5%, the exposure envelope duration in some instances can exceed 500 milliseconds.

Thus, the following key parameters have been found in order to create harmless, true subthreshold photocoagulation in retinal tissue in accordance with the present invention:
  a) light beam having a wavelength of at least 532 nm, and preferably between 532 nm to 1300 nm;
  b) low duty cycle, such as less than 10% and preferably 5% or less;
  c) small spot size to minimize heat accumulation and assure uniform heat distribution within a given laser spot so as to maximize heat dissipation; and
  d) sufficient power to produce retinal laser exposures between 18-55 times MPE producing an RPE temperature rise of 7° C.-14° C. and retinal irradiance of between 100-590 W/CM$^2$.

Using these foregoing parameters, harmless yet therapeutically effective true subthreshold or invisible photocoagulation phototherapy treatment can be obtained which can be attained which has been found to produce benefits of conventional photocoagulation phototherapy but avoid drawbacks and complications of conventional phototherapy. Adverse treatment effects are completely eliminated and functional retina preserved rather than sacrificed. Moreover, the entire retina can be exposed to the pulsed energy source of the present invention, allowing both preventative and therapeutic treatment of eyes with retinal disease completely rather than locally or subtotally.

In the retina, the clinical benefits of SDM are produced by sub-morbid photothermal RPE HSP activation. In dysfunctional RPE cells, HSP stimulation by SDM results in normalized cytokine expression and consequently improved retinal structure and function. As normally functioning cells are not in need of repair, HSP stimulation in normal cells would tend to have no notable clinical effect. The "patho-selectivity" of near infrared laser effects, such as SDM affecting sick cells but not affecting normal ones on various cell types, is consistent with clinical observations of SDM. This facility is key to the suitability of SDM for early and preventative treatment of eyes with chronic progressive disease and eyes with minimal retinal abnormality and minimal dysfunction. Despite the safety of SDM, the clinical effects of SDM are marked and profound. For instance, SDM reduces the rate of progression of diabetic retinopathy by 85% (P=0.0001) and age-related macular degeneration by 95% (P<0.0001), improves optic nerve function in glaucoma (P=0.001) and visual fields in glaucoma and all retinal diseases including retinitis pigmentosa (P=0001).

With reference now to FIG. 1, a schematic diagram is shown of a system for realizing the process of the present invention. The system, generally referred to by the reference number 10, includes a laser console 12, such as for example the 810 nm near infrared micropulsed diode laser in the preferred embodiment. The laser generates a laser light beam which is passed through optics, such as an optical lens or mask, or a plurality of optical lenses and/or masks 14 as needed. The laser projector optics 14 pass the shaped light beam to a coaxial wide-field non-contact digital optical viewing system/camera 16 for projecting the laser beam light onto the eye 18 of the patient, or other biological target tissue or bodily fluid as more fully discussed herein. It will be understood that the box labeled 16 can represent both the laser beam projector as well as a viewing system/camera, which might in reality comprise two different components in use. The viewing system/camera 16 provides feedback to a display monitor 20, which may also include the necessary computerized hardware, data input and controls, etc. for manipulating the laser 12, the optics 14, and/or the projection/viewing components 16.

Figure 2:
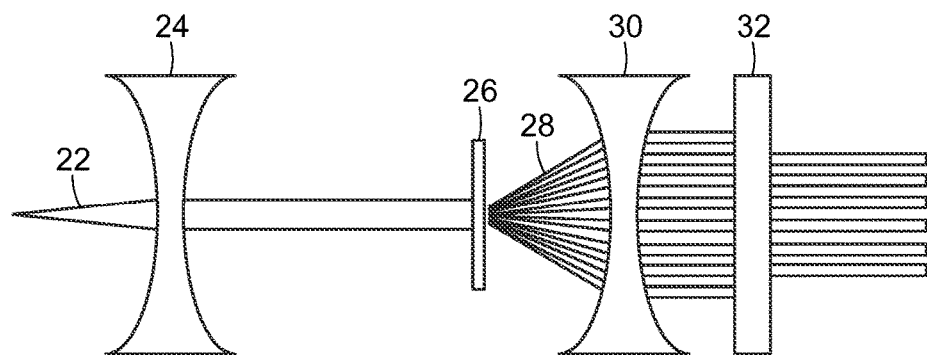
FIG. 2 is a diagrammatic view of optics used to generate a laser light geometric pattern, in accordance with the present invention.

With reference now to FIG. 2, in one embodiment, the laser light beam 22 is passed through a collimator lens 24 and then through a mask 26. In a particularly preferred embodiment, the mask 26 comprises a diffraction grating. The mask/diffraction grating 26 produces a geometric object, or more typically a geometric pattern of simultaneously produced multiple laser spots or other geometric objects. This is represented by the multiple laser light beams labeled with reference number 28. Alternatively, the multiple laser spots may be generated by a plurality of fiber optic wires. Either method of generating laser spots allows for the creation of a very large number of laser spots simultaneously over a very wide treatment field, such as consisting of the entire retina. In fact, a very high number of laser spots, perhaps numbering in the hundreds even thousands or more could cover the entire ocular fundus and entire retina, including the macula and fovea, retinal blood vessels and optic nerve. The intent of the process in the present invention is to better ensure complete and total coverage and treatment of the target area, which may comprise a retina, and sparing none of the retina by the laser so as to improve vision.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 26 diffracts, producing a periodic pattern a distance away from the mask 26, shown by the laser beams labeled 28 in FIG. 2. The single laser beam 22 has thus been formed into multiple, up to hundreds or even thousands, of individual laser beams 28 so as to create the desired pattern of spots or other geometric objects. These laser beams 28 may be passed through additional lenses, collimators, etc. 30 and 32 in order to convey the laser beams and form the desired pattern on the patient's retina. Such additional lenses, collimators, etc. 30 and 32 can further transform and redirect the laser beams 28 as needed.

Arbitrary patterns can be constructed by controlling the shape, spacing and pattern of the optical mask 26. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Although hundreds or even thousands of simultaneous laser spots could be generated and created and formed into patterns to be applied to the tissue, due to the requirements of not overheating the tissue, there are constraints on the number of treatment spots or beams which can be simultaneously used in accordance with the present invention. Each individual laser beam or spot requires a minimum average power over a train duration to be effective. However, at the same time, tissue cannot exceed certain temperature rises without becoming damaged. For example, using an 810 nm wavelength laser, the number of simultaneous spots generated and used could number from as few as 1 and up to approximately 100 when a 0.04 (4%) duty cycle and a total train duration of 0.3 seconds (300 milliseconds) is used.

Absorption by water increases as the wavelength is increased, resulting in heating over the long path length through the vitreous humor in front of the retina. For shorter wavelengths, e.g., 577 nm, the absorption coefficient in the RPE's melanin can be higher, and therefore the laser power can be lower. For example, at 577 nm, the power can be lowered by a factor of 4 for the invention to be effective. Accordingly, there can be as few as a single laser spot or up to approximately 400 laser spots when using the 577 nm wavelength laser light, while still not harming or damaging the eye or other tissue. The present invention can use a multitude of simultaneously generated therapeutic light beams or spots, such as numbering in the dozens or even hundreds, as the parameters and methodology of the present invention create therapeutically effective yet non-destructive and non-permanently damaging treatment.

Figure 3:
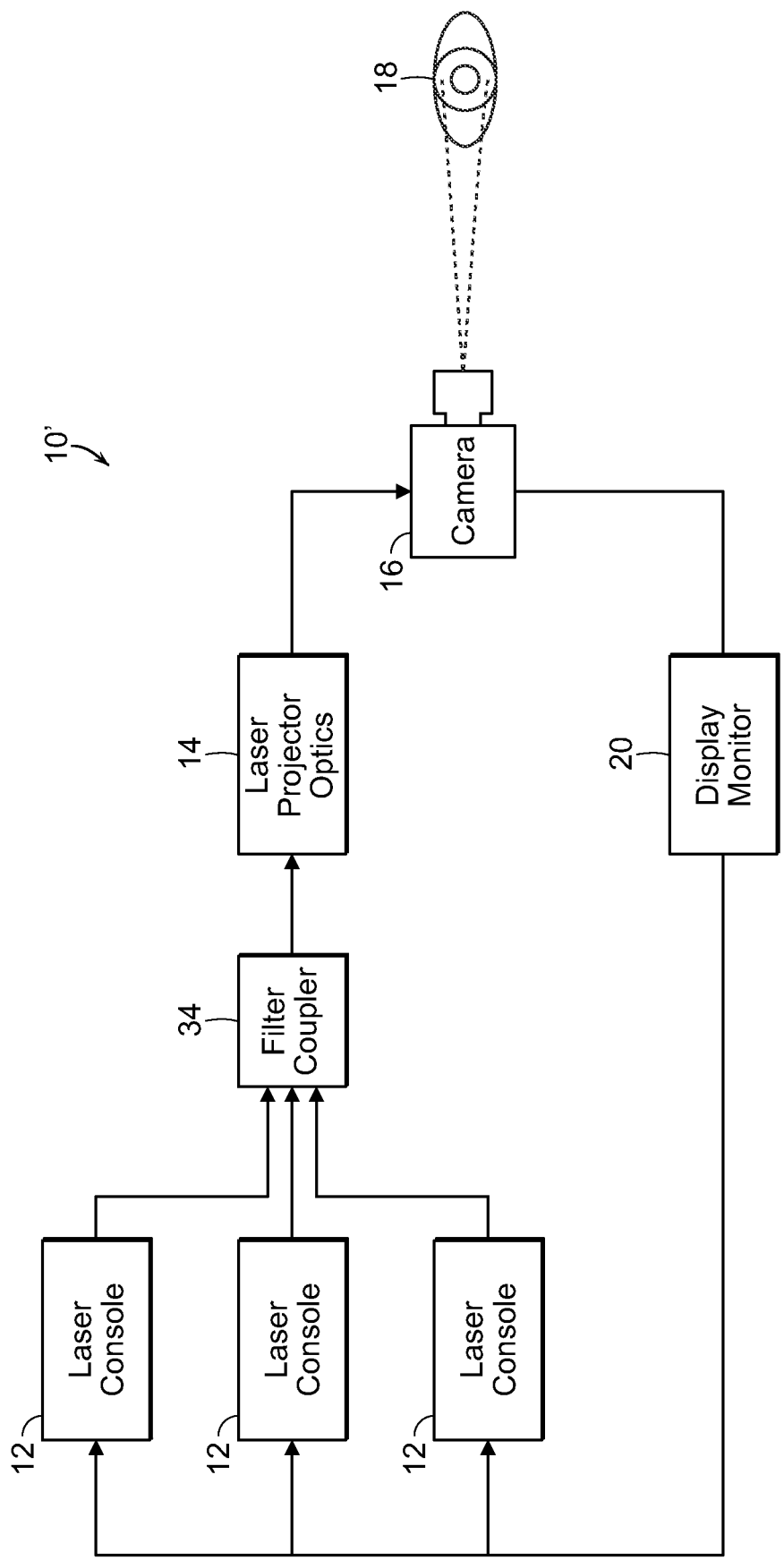
FIG. 3 is a diagrammatic view illustrating an alternate embodiment of the system to use to generate laser light beams for treating tissue and fluid, in accordance with the present invention.

FIG. 3 illustrates diagrammatically a system which couples multiple light sources into the pattern-generating optical subassembly described above. Specifically, this system 10' is similar to the system 10 described in FIG. 1 above. The primary differences between the alternate system 10' and the earlier described system 10 is the inclusion of a plurality of laser consoles 12, the outputs of which are each fed into a fiber coupler 34. The fiber coupler produces a single output that is passed into the laser projector optics 14 as described in the earlier system. The coupling of the plurality of laser consoles 12 into a single optical fiber is achieved with a fiber coupler 34 as is known in the art. Other known mechanisms for combining multiple light sources are available and may be used to replace the fiber coupler described herein.

In this system 10' the multiple light sources 12 follow a similar path as described in the earlier system 10, i.e., collimated, diffracted, recollimated, and directed into the retina with a steering mechanism. In this alternate system 10' the diffractive element functions differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the steering mechanism 16 to the retina 18 for treatment. The slight difference in the diffraction angles will affect how the steering pattern achieves coverage of the retina.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the tissue area to be treated, the application of the other wavelengths achieves either incomplete or overlapping coverage of the tissue. The second mode sequentially applies each light source of a varying or different wavelength with the proper steering pattern to achieve complete coverage of the tissue for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 4:
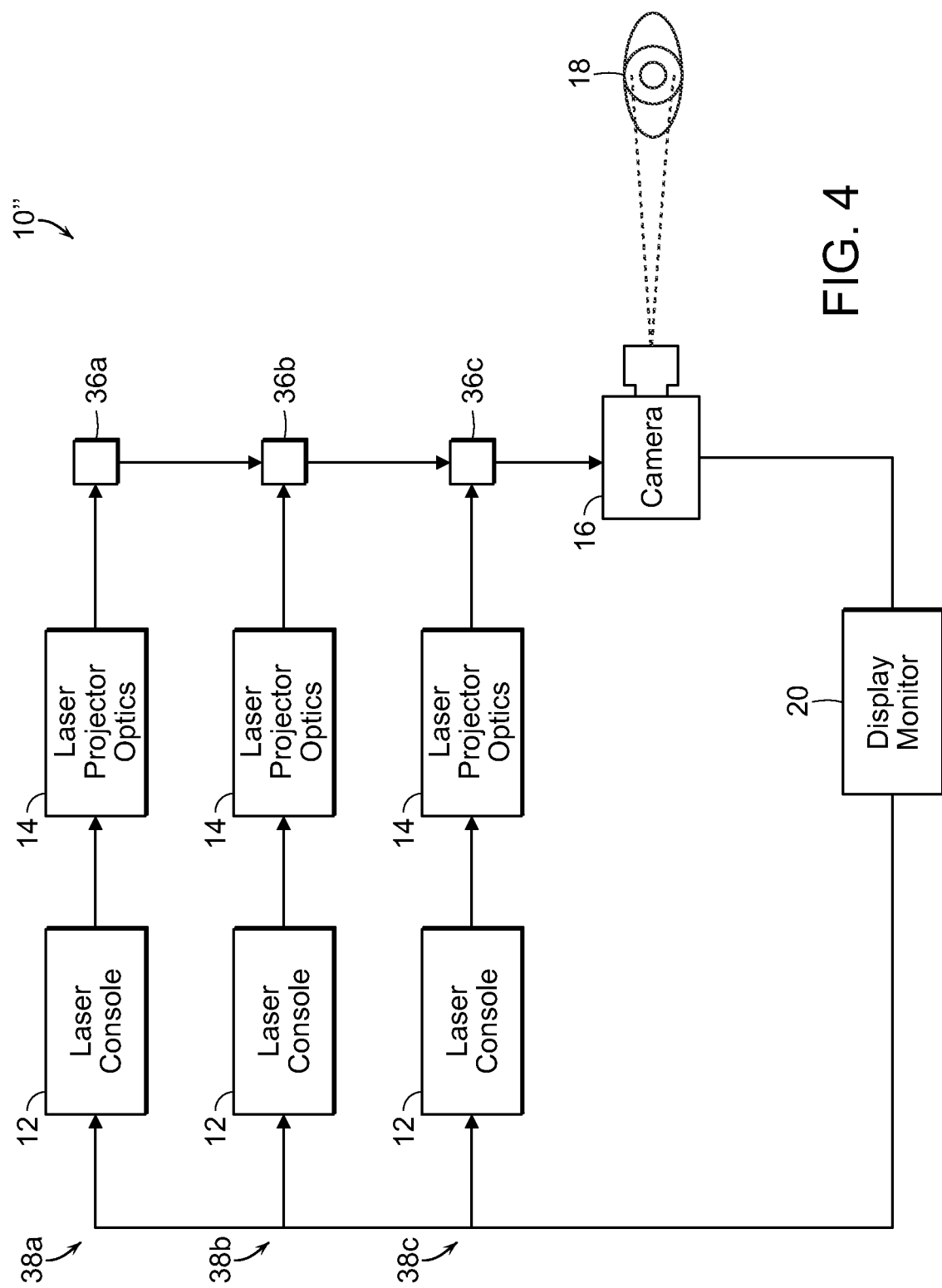
FIG. 4 is a diagrammatic view illustrating yet another embodiment of a system used to generate laser light beams to treat tissue in accordance with the present invention.

FIG. 4 illustrates diagrammatically yet another alternate embodiment of the inventive system 10". This system 10" is configured generally the same as the system 10 depicted in FIG. 1. The main difference resides in the inclusion of multiple pattern-generating subassembly channels tuned to a specific wavelength of the light source. Multiple laser consoles 12 are arranged in parallel with each one leading directly into its own laser projector optics 14. The laser projector optics of each channel 38a, 38b, 38c comprise a collimator 24, mask or diffraction grating 28 and recollimators 30, 32 as described in connection with FIG. 2 above—the entire set of optics tuned for the specific wavelength generated by the corresponding laser console 12. The output from each set of optics 14 is then directed to a beam splitter 36 for combination with the other wavelengths. It is known by those skilled in the art that a beam splitter used in reverse can be used to combine multiple beams of light into a single output.

The combined channel output from the final beam splitter 36c is then directed through the camera 16 which applies a steering mechanism to allow for complete coverage of the retina 18.

In this system 10" the optical elements for each channel are tuned to produce the exact specified pattern for that channel's wavelength. Consequently, when all channels are combined and properly aligned a single steering pattern may be used to achieve complete coverage of the retina for all wavelengths.

The system 10" may use as many channels 38a, 38b, 38c, etc. and beam splitters 36a, 36b, 36c, etc. as there are wavelengths of light being used in the treatment.

Implementation of the system 10" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 10", each channel begins with a light source 12, which could be from an optical fiber as in other embodiments of the pattern-generating subassembly. This light source 12 is directed to the optical assembly 14 for collimation, diffraction, recollimation and directed into the beam splitter which combines the channel with the main output.

The field of photobiology reveals that different biologic effects may be achieved by exposing target tissues to lasers of different wavelengths. The same may also be achieved by consecutively applying multiple lasers of either different or the same wavelength in sequence with variable time periods of separation and/or with different irradiant energies. The present invention anticipates the use of multiple laser, light or radiant wavelengths (or modes) applied simultaneously or in sequence to maximize or customize the desired treatment effects. This method also minimizes potential detrimental effects. The optical methods and systems illustrated and described above provide simultaneous or sequential application of multiple wavelengths.

Typically, the system of the present invention incorporates a guidance system to ensure complete and total treatment with photostimulation. Fixation/tracking/registration systems consisting of a fixation target, tracking mechanism, and linked to system operation can be incorporated into the present invention.

In a particularly preferred embodiment, the geometric pattern of simultaneous laser spots is sequentially offset so as to achieve confluent and complete treatment of the target tissue. This is done in a time-saving manner by placing a plurality of spots over the target tissue at once. This pattern of simultaneous spots is scanned, shifted, or redirected as an entire array sequentially, so as to cover the entire target tissue in a single treatment session.

Figure 5:
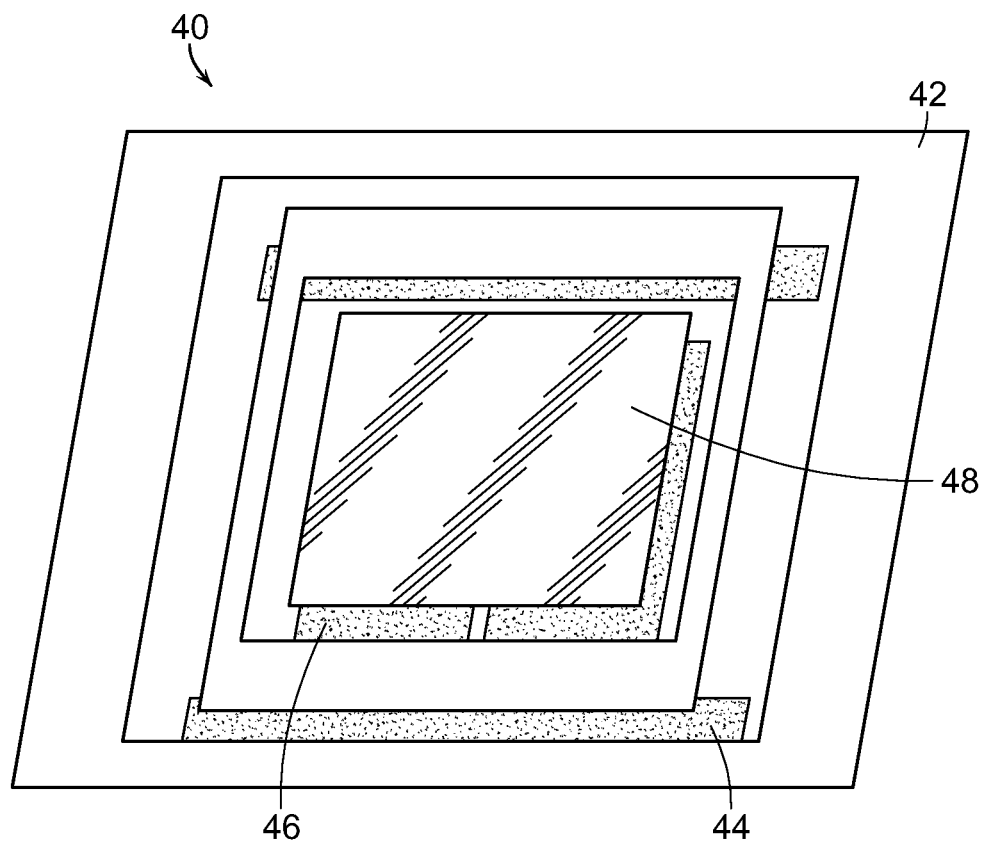
FIG. 5 is a top plan view of an optical scanning mechanism, used in accordance with the present invention.
Figure 6:
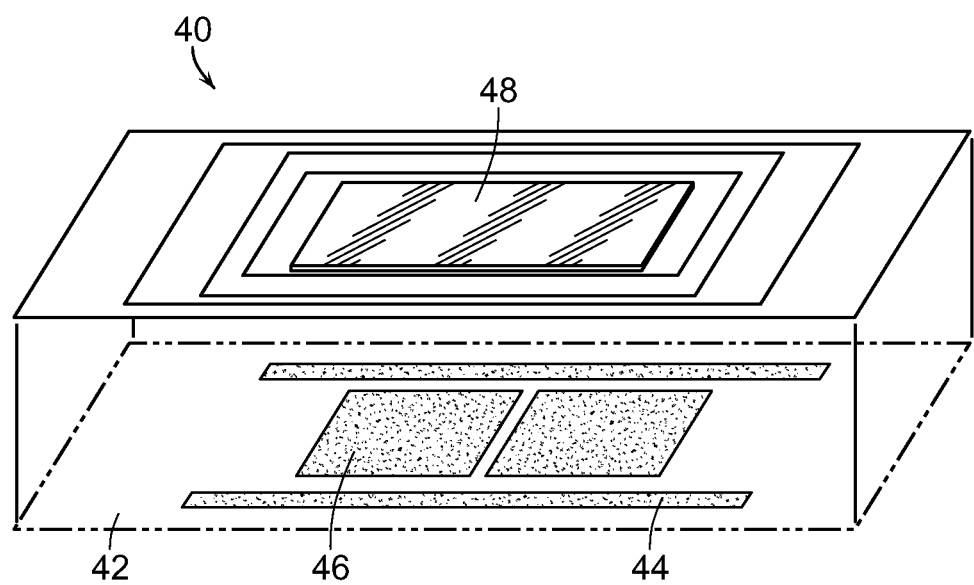
FIG. 6 is a partially exploded view of the optical scanning mechanism of FIG. 5, illustrating various component parts thereof.

This can be done in a controlled manner using an optical scanning mechanism 40. FIGS. 5 and 6 illustrate an optical scanning mechanism 40 which may be used in the form of a MEMS mirror, having a base 42 with electronically actuated controllers 44 and 46 which serve to tilt and pan the mirror 48 as electricity is applied and removed thereto. Applying electricity to the controller 44 and 46 causes the mirror 48 to move, and thus the simultaneous pattern of laser spots or other geometric objects reflected thereon to move accordingly on the target tissue of the patient. This can be done, for example, in an automated fashion using an electronic software program to adjust the optical scanning mechanism 40 until complete coverage of the target tissue, or at least the portion of the target tissue desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 7:
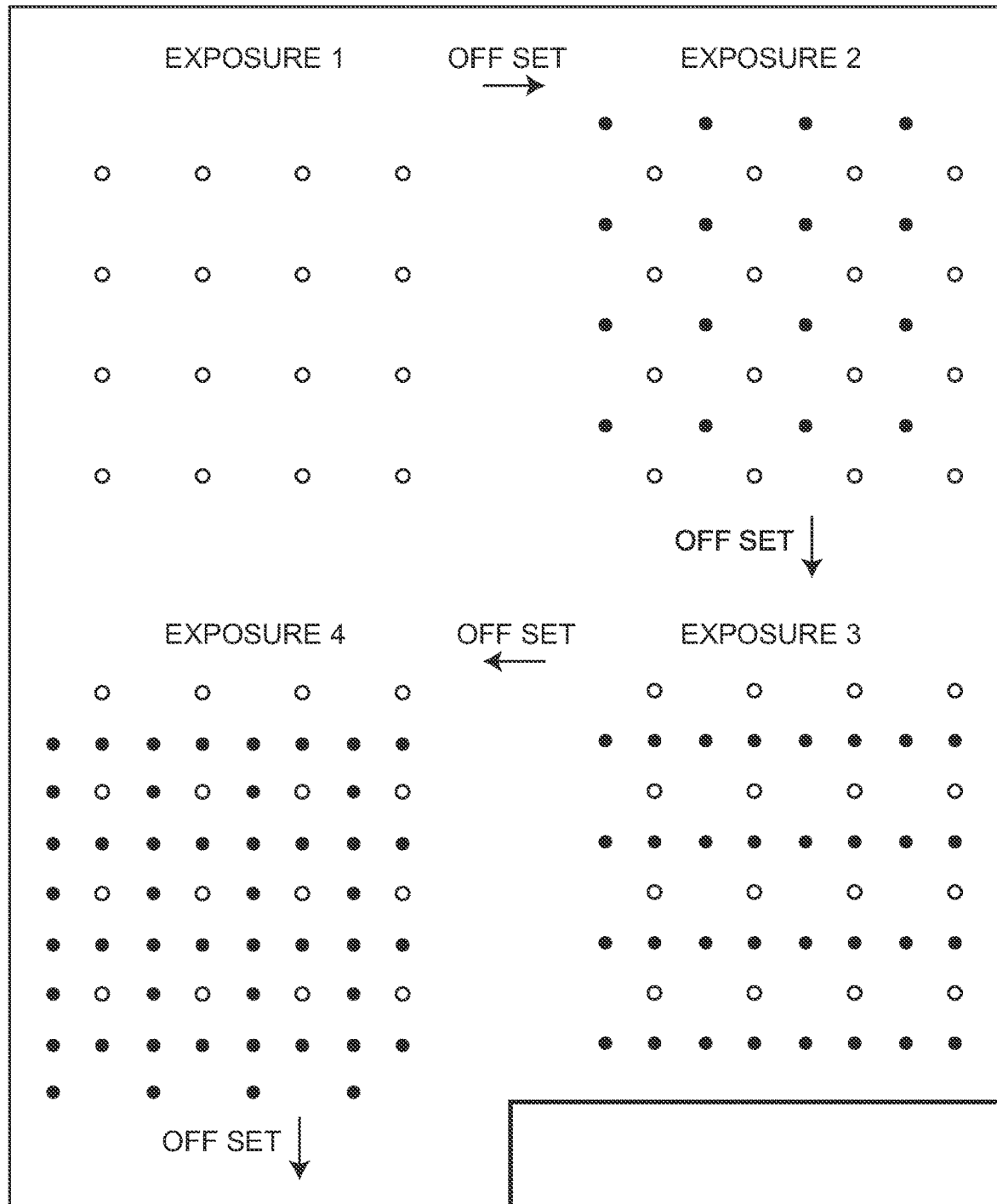
FIG. 7 illustrates controlled offset of exposure of an exemplary geometric pattern grid of laser spots to treat a target tissue, in accordance with the present invention.

Since the parameters of the present invention dictate that the applied radiant energy or laser light is not destructive or damaging, the geometric pattern of laser spots, for example, can be overlapped without destroying the tissue or creating any permanent damage. However, in a particularly preferred embodiment, as illustrated in FIG. 7, the pattern of spots are offset at each exposure so as to create space between the immediately previous exposure to allow heat dissipation and prevent the possibility of heat damage or tissue destruction. Thus, as illustrated in FIG. 7, the pattern, illustrated for exemplary purposes as a grid of sixteen spots, is offset each exposure such that the laser spots occupy a different space than previous exposures. It will be understood that the diagrammatic use of circles or empty dots as well as filled dots are for diagrammatic purposes only to illustrate previous and subsequent exposures of the pattern of spots to the area, in accordance with the present invention. The spacing of the laser spots prevents overheating and damage to the tissue. It will be understood that this occurs until the entire target tissue has received phototherapy, or until the desired effect is attained. This can be done, for example, by a scanning mechanism, such as by applying electrostatic torque to a micromachined mirror, as illustrated in FIGS. 5 and 6. By combining the use of small laser spots separated by exposure free areas, prevents heat accumulation, and grids with a large number of spots per side, it is possible to atraumatically and invisibly treat large target areas with short exposure durations very rapidly.

By rapidly and sequentially repeating redirection or offsetting of the entire simultaneously applied grid array of spots or geometric objects, complete coverage of the target tissue, such as a human retina, can be achieved rapidly without thermal tissue injury. This offsetting can be determined algorithmically to ensure the fastest treatment time and least risk of damage due to thermal tissue, depending on laser parameters and desired application.

For example, the following has been modeled using the Fraunhoffer Approximation. With a mask having a nine by nine square lattice, with an aperture radius 9 μm, an aperture spacing of 600 μm, using a 890 nm wavelength laser, with a mask-lens separation of 75 mm, and secondary mask size of 2.5 mm by 2.5 mm, the following parameters will yield a grid having nineteen spots per side separated by 133 μm with a spot size radius of 6 μm. The number of exposures "m" required to treat (cover confluently with small spot applications) given desired area side-length "A", given output pattern spots per square side "n", separation between spots "R", spot radius "r" and desired square side length to treat area "A", can be given by the following formula:

$$m = \frac{A}{nR} \text{floor}\left(\frac{R}{2r}\right)^2$$

With the foregoing setup, one can calculate the number of operations m needed to treat different field areas of exposure. For example, a 3 mm times 3 mm area, which is useful for treatments, would require 98 offsetting operations, requiring a treatment time of approximately thirty seconds. Another example would be a 3 cm times 3 cm area. For such a large treatment area, a much larger secondary mask size of 25 mm by 25 mm could be used, yielding a treatment grid of 190 spots per side separated by 133 μm with a spot size radius of 6 μm. Since the secondary mask size was increased by the same factor as the desired treatment area, the number of offsetting operations of approximately 98, and thus treatment time of approximately thirty seconds, is constant. Field sizes of 3 mm would, for example, allow treatment of the entire human macula in a single exposure, useful for treatment of common blinding conditions such as diabetic macular edema and age-related macular degeneration. Performing the entire 98 sequential off settings would ensure entire coverage of the macula.

Of course, the number and size of spots produced in a simultaneous pattern array can be easily and highly varied such that the number of sequential offsetting operations required to complete treatment can be easily adjusted depending on the therapeutic requirements of the given application.

Furthermore, by virtue of the small apertures employed in the diffraction grating or mask, quantum mechanical behavior may be observed which allows for arbitrary distribution of the laser input energy. This would allow for the generation of any arbitrary geometric shapes or patterns, such as a plurality of spots in grid pattern, lines, or any other desired pattern. Other methods of generating geometric shapes or patterns, such as using multiple fiber optical fibers or microlenses, could also be used in the present invention.

Figure 8:
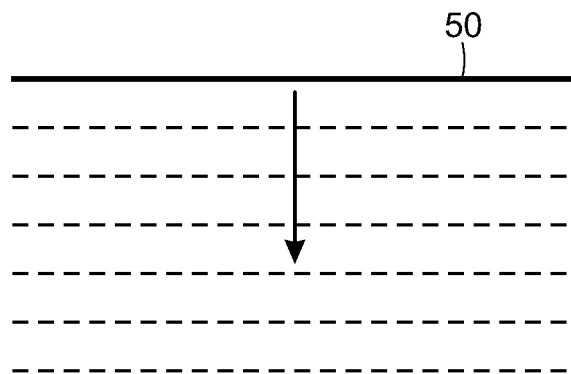
FIG. 8 is a diagrammatic view illustrating a geometric object in the form of a line controllably scanned to treat a target tissue, in accordance with the present invention.
Figure 9:
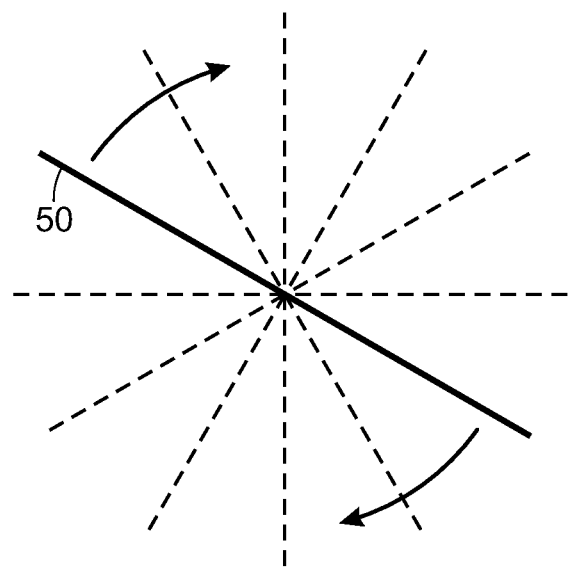
FIG. 9 is a diagrammatic view similar to FIG. 8, but illustrating the geometric line or bar rotated to treat an area, in accordance with the present invention.

With reference now to FIGS. 8 and 9, instead of a geometric pattern of small laser spots, the present invention contemplates use of other geometric objects or patterns. For example, a single line 50 of laser light, formed continuously or by means of a series of closely spaced spots, can be created. An offsetting optical scanning mechanism can be used to sequentially scan the line over an area, illustrated by the downward arrow in FIG. 8. With reference now to FIG. 9, the same geometric object of a line 50 can be rotated, as illustrated by the arrows, so as to create a circular field of phototherapy. The potential negative of this approach, however, is that the central area will be repeatedly exposed, and could reach unacceptable temperatures. This could be overcome, however, by increasing the time between exposures, or creating a gap in the line such that the central area is not exposed.

Power limitations in current micropulsed diode lasers require fairly long exposure duration. The longer the exposure, the more important the center-spot heat dissipating ability toward the unexposed tissue at the margins of the laser spot. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Aside from power limitations, another parameter of the present invention is the duty cycle, or the frequency of the train of micropulses, or the length of the thermal relaxation time between consecutive pulses. It has been found that the use of a 10% duty cycle or higher adjusted to deliver micropulsed laser at similar irradiance at similar MPE levels significantly increase the risk of lethal cell injury. However, duty cycles of less than 10%, and preferably 5% or less demonstrate adequate thermal rise and treatment at the level of the MPE cell to stimulate a biological response, but remain below the level expected to produce lethal cell injury. The lower the duty cycle, however, the exposure envelope duration increases, and in some instances can exceed 500 milliseconds.

Each micropulse lasts a fraction of a millisecond, typically between 50 microseconds to 100 microseconds in duration. Thus, for the exposure envelope duration of 300-

500 milliseconds, and at a duty cycle of less than 5%, there is a significant amount of time between micropulses to allow the thermal relaxation time between consecutive pulses. Typically, a delay of between 1 and 3 milliseconds, and preferably approximately 2 milliseconds, of thermal relaxation time is needed between consecutive pulses. For adequate treatment, the cells are typically exposed or hit by the laser light between 50-200 times, and preferably between 75-150 at each location. With the 1-3 milliseconds of relaxation or interval time, the total time in accordance with the embodiments described above to treat a given area, or more particularly the locations of the target tissue which are being exposed to the laser spots is between 200 milliseconds and 500 milliseconds on average. The thermal relaxation time is required so as not to overheat the cells within that location or spot and so as to prevent the cells from being damaged or destroyed.

The inventors have found that treatment in accordance with the invention of patients suffering from age-related macular degeneration (AMD) can slow the progress or even stop the progression of AMD. Further evidence of this restorative treatment effect is the inventor's finding that treatment can uniquely reduce the risk of vision loss in AMD due to choroidal neovascularization by as much as 90%. Most of the patients have seen significant improvement in dynamic functional mesopic log MAR visual acuity and contrast visual acuity after the treatment in accordance with the invention, with some experiencing better vision. It is believed that this works by targeting, preserving, and "normalizing" (moving toward normal) function of the retinal pigment epithelium (RPE).

Treatment in accordance with the invention has also been shown to stop or reverse the manifestations of the diabetic retinopathy disease state without treatment-associated damage or adverse effects, despite the persistence of systemic diabetes mellitus. Studies by the inventor have shown that the restorative effect of treatment can uniquely reduce the risk of progression of diabetic retinopathy by 85%. On this basis it is hypothesized that the invention might work by inducing a return to more normal cell function and cytokine expression in diabetes-affected RPE cells, analogous to hitting the "reset" button of an electronic device to restore the factory default settings.

Based on the above information and studies, SDM treatment may directly affect cytokine expression and heat shock protein (HSP) activation in the targeted tissue, particularly the retinal pigment epithelium (RPE) layer. Panretinal and panmacular SDM has been noted by the inventors to reduce the rate of progression of many retinal diseases, including severe non-proliferative and proliferative diabetic retinopathy, AMD, DME, etc. The known therapeutic treatment benefits of individuals having these retinal diseases, coupled with the absence of known adverse treatment effects, allows for consideration of early and preventative treatment, liberal application and retreatment as necessary. The reset theory also suggests that the invention may have application to many different types of RPE-mediated retinal disorders. In fact, the inventor has recently shown that panmacular treatment can significantly improve retinal function and health, retinal sensitivity, and dynamic log MAR visual acuity and contrast visual acuity in dry age-related macular degeneration, retinitis pigmentosa, cone-rod retinal degenerations, and Stargardt's disease where no other treatment has previously been found to do so.

Currently, retinal imaging and visual acuity testing guide management of chronic, progressive retinal diseases. As tissue and/or organ structural damage and vision loss are late disease manifestations, treatment instituted at this point must be intensive, often prolonged and expensive, and frequently fails to improve visual acuity and rarely restores normal vision. As the invention has been shown to be an effective treatment for a number of retinal disorders without adverse treatment effects, and by virtue of its safety and effectiveness, it can also be used to treat an eye to stop or delay the onset or symptoms of retinal diseases prophylactically or as a preventative treatment for such retinal diseases. Any treatment that improves retinal function, and thus health, should also reduce disease severity, progression, untoward events and visual loss. By beginning treatment early, prior to pathologic structural change, and maintaining the treatment benefit by regular functionally-guided retreatment, structural degeneration and visual loss might thus be delayed if not prevented. Even modest early reductions in the rate of disease progression may lead to significant long-term reductions and complications in visual loss. By mitigating the consequences of the primary defect, the course of disease may be muted, progression slowed, and complications and visual loss reduced. This is reflected in the inventor's studies, finding that treatment reduces the risk of progression and visual loss in diabetic retinopathy by 85% and AMD by 80%.

In accordance with an embodiment of the present invention, it is determined that a patient, such as an eye of the patient, has a risk for a disease. This may be before imaging abnormalities are detectable. Such a determination may be accomplished by ascertaining if the patient is at risk for a chronic progressive disease, such as retinopathy, including diabetes, a risk for age-related macular degeneration or retinitis pigmentosa. Alternatively, or additionally, results of an examination or test of the patient may be abnormal. A specific test, such as a physiology test or a genetic test, may be conducted to establish that the patient has a risk for a disease.

When treating or prophylactically protecting retinal or other eye tissue having a chronic progressive disease or a risk of a chronic progressive disease, a laser light beam, that is sublethal and creates true subthreshold photocoagulation and retinal tissue, is generated and at least a portion of the retinal tissue is exposed to the generated laser light beam without damaging the exposed retinal or foveal tissue, so as to provide preventative and protective treatment of the retinal tissue of the eye. The treated retina may comprise the fovea, foveola, retinal pigment epithelium (RPE), choroid, choroidal neovascular membrane, subretinal fluid, macula, macular edema, parafovea, and/or perifovea. The laser light beam may be exposed to only a portion of the retina, or substantially the entire retina and fovea.

While most treatment effects appear to be long-lasting, if not permanent, clinical observations suggest that it can appear to wear off on occasion. Accordingly, the tissue is periodically retreated. This may be done according to a set schedule or when it is determined that the tissue of the patient is to be retreated, such as by periodically monitoring visual and/or retinal function or condition of the patient.

Although the present invention is particularly suited for treatment of retinal diseases, such as diabetic retinopathy and macular edema, it has been found that it can be used for other diseases as well. The system and process of the present invention could target the trabecular mesh work as treatment for glaucoma, accomplished by another customized treatment field template. Moreover, treatment of retinal tissue using SDM, as explained above, in eyes with advanced open-angle glaucoma have shown improved key measures of optic nerve and ganglion cell function, indicating a significant neuroprotective effect of this treatment. Visual fields also improved, and there was no adverse treatment effects. Thus, it is believed that SDM, in accordance with the present invention, may aid in the clinical management of glaucoma by reducing the risk of visual loss, independent of intraocular pressure (10P) lowering.

Low-intensity/high density subthreshold (sublethal) diode micropulsed laser (SDM), as explained in detail above, has been shown to be effective in the treatment of traditional retinal laser indications such as diabetic macular edema, proliferative diabetic retinopathy, central serious chorioretinopathy, and branch retinal vein occlusion, without adverse treatment effects. As described above, the mechanism of the retinal laser treatment is sometimes referred to herein as "reset to default" theory, which postulates that the primary mode of retinal laser action is sublethal activation of the retinal pigment epithelial (RPE) heat shock proteins.

A study recently conducted by the inventors also shows that SDM should be neuroprotective in open-angle glaucoma. Linear regression analysis demonstrated that the most abnormal values prior to treatment improved the most following treatment for nearly all measures. Panmacular SDM treatment, in accordance with the present invention, in eyes with advanced open-angle glaucoma (OAG) improved key measures of optic nerve and ganglion cell function, indicating a significant neuroprotective effective treatment. The visual fields also improved, and there were no adverse treatment effects. Thus, generating a micropulsed laser light beam having characteristics and parameters discussed above and applying the laser light beam to the retinal and/or foveal tissue of an eye having glaucoma or a risk of glaucoma creates a therapeutic effect to the retinal and/or foveal tissue exposed to the laser light beam without destroying or permanently damaging the retinal and/or foveal tissue and also improves function or condition of an optic nerve and/or retinal ganglion cells of the eye.

Retinal ganglion cells and the optic nerve are subject to the health and function of the retinal pigment epithelium (RPE). Retinal homeostasis is principally maintained by the RPE via still the poorly understood but exquisitely complex interplay of small proteins excreted by the RPE into the intercellular space called "cytokines". Some RPE-derived cytokines, like pigment epithelial derived factor (PEDF) are neuroprotective. Retinal laser treatment may alter RPE cytokine expression, including, but not limited to, increasing expression of PEDF. Absent retinal damage, the effect of SDM, in accordance with the present invention, is "homeotrophic", moving retinal function toward normal. By normalizing RPE function, it follows that retinal autoregulation and cytokine expression is also normalized. This suggests the normalization of retinal cytokine expression may be the source of the neuroprotective effects from SDM in OAG.

Despite the markedly beneficial effects of SDM in chronic progressive retinal diseases, there are no other treatments for most of these diseases that have any benefit at all. In this respect, retinal CPDs are also like CPDs elsewhere. In all CPDs including type II diabetes, Alzheimer disease, idiopathic pulmonary fibrosis (IPF) and ischemic heart disease and various cardiomyopathies, abnormalities of the HSP system has been recognized and stimulation found to be beneficial. Currently, outside of the present invention, there is no non-physical therapy to stimulate HSP homeotrophic effects in systemic CPDs. Experience with SDM in connection with eye diseases suggests that appropriately designed PEMR should effectively and safely treat any CPDs affecting any other part of the body. Moreover, experience with SDM in otherwise untreatable retinal diseases suggests that the beneficial effects of PEMR elsewhere should be major and not minor, robust, significant and safe. As with SDM, the effect of PEMR for CPDs elsewhere in the body would most likely not cure the primary cause of disease (age, diabetes, genetic defect, etc.), but instead the effect would be to slow, stop or reverse the disease process by repair of the abnormalities that develop as a consequence of the primary disease defect. By maintenance of the treatment benefits via periodic retreatment, the course of the disease process should be attenuated, reducing the risks of death and disability.

As heat shock proteins play a role in responding to a large number of abnormal conditions in body tissue other than eye tissue, it is believed that similar systems and methodologies can be advantageously used in treating such abnormal conditions, infections, etc. As such, the present invention is also directed to the controlled application of pulsed ultrasound or electromagnetic radiation to treat abnormal conditions including inflammations, autoimmune conditions, and cancers that are accessible by means of fiber optics of endoscopes or surface probes as well as focused electromagnetic/sound waves. For example, cancers on the surface of the prostate that have the largest threat of metastasizing can be accessed by means of fiber optics in a proctoscope. Colon tumors can be accessed by an optical fiber system, like those used in colonoscopy.

As indicated above, subthreshold diode micropulsed laser (SDM) photostimulation has been effective in stimulating direct repair of slightly misfolded proteins in eye tissue. Besides HSP activation, another way this may occur is because the spikes in temperature caused by the micropulses in the form of a thermal time-course allows diffusion of water inside proteins, and this allows breakage of the peptide-peptide hydrogen bonds that prevent the protein from returning to its native state. The diffusion of water into proteins results in an increase in the number of restraining hydrogen bonds by a factor on the order of a thousand. Thus, it is believed that this process could be applied to other diseases advantageously as well.

Laser treatment can induce HSP production or activation and alter cytokine expression. The more sudden and severe the non-lethal cellular stress (such as laser irradiation), the more rapid and robust HSP activation. Thus, a burst of repetitive low temperature thermal spikes at a very steep rate of change (~7° C. elevation with each 100 µs micropulse, or 70,000° C./sec) produced by each SDM exposure is especially effective in stimulating activation of HSPs, particularly compared to non-lethal exposure to subthreshold treatment with continuous wave lasers, which can duplicate only the low average tissue temperature rise.

In accordance with the system and method of the present invention, a pulsed energy source, such as laser, ultrasound, ultraviolet, radiofrequency, microwave radiofrequency and the like, having energy parameters selected to cause a thermal time-course in tissue or bodily fluid to raise the target tissue or bodily fluid temperature over a short period of time to a sufficient level to achieve a therapeutic effect while maintaining average tissue temperature over a prolonged period of time below a predetermined level so as to avoid permanent tissue damage. It is believed that the creation of the thermal time-course stimulates heat shock protein activation or production and facilitates protein repair without causing any cellular damage. The parameters of the pulsed energy source and its application to the target tissue or target bodily fluid is important in creating the thermal time-course so as to have a therapeutic effect without causing damage.

The selection of these parameters may be determined by requiring that the Arrhenius integral for HSP activation be greater than 1 or unity. Arrhenius integrals are used for analyzing the impacts of actions on biological tissue. See, for instance, The CRC Handbook of Thermal Engineering, ed. Frank Kreith, Springer Science and Business Media (2000). At the same time, the selected parameters must not permanently damage the tissue. Thus, the Arrhenius integral for damage may also be used, wherein the solved Arrhenius integral is less than 1 or unity.

Alternatively, the FDA/FCC constraints on energy deposition per unit gram of tissue and temperature rise as measured over periods of minutes be satisfied so as to avoid permanent tissue damage. The FDA/FCC requirements on energy deposition and temperature rise are widely used and can be referenced, for example, at www.fda.gov/medicaldevices/deviceregulationandguidance/guidancedocuments/ucm073817.htm#attacha for electromagnetic sources, and Anastosio and P. LaRivero, ed., Emerging Imaging Technologies. CRC Press (2012), for ultrasound sources.

Generally speaking, tissue temperature rises of between 6° C. and 11° C. for a short period of time, such as seconds or fractions of a second, can create therapeutic effect, such as by activating heat shock proteins, whereas maintaining the average tissue temperature over a prolonged period of time, such as over several minutes, such as six minutes, below a predetermined temperature, such as 6° C. and even 1° C. or less in certain circumstances, will not permanently damage the tissue.

As explained above, the energy source to be applied to the target tissue will have energy and operating parameters which must be determined and selected so as to achieve the therapeutic effect while not permanently damaging the tissue. Using a light beam energy source, such as a laser light beam, as an example, the laser wavelength, duty cycle and total pulse train duration parameters must be taken into account. Other parameters which can be considered include the radius of the laser source as well as the average laser power. Adjusting or selecting one of these parameters can have an effect on at least one other parameter.

Figure 10:
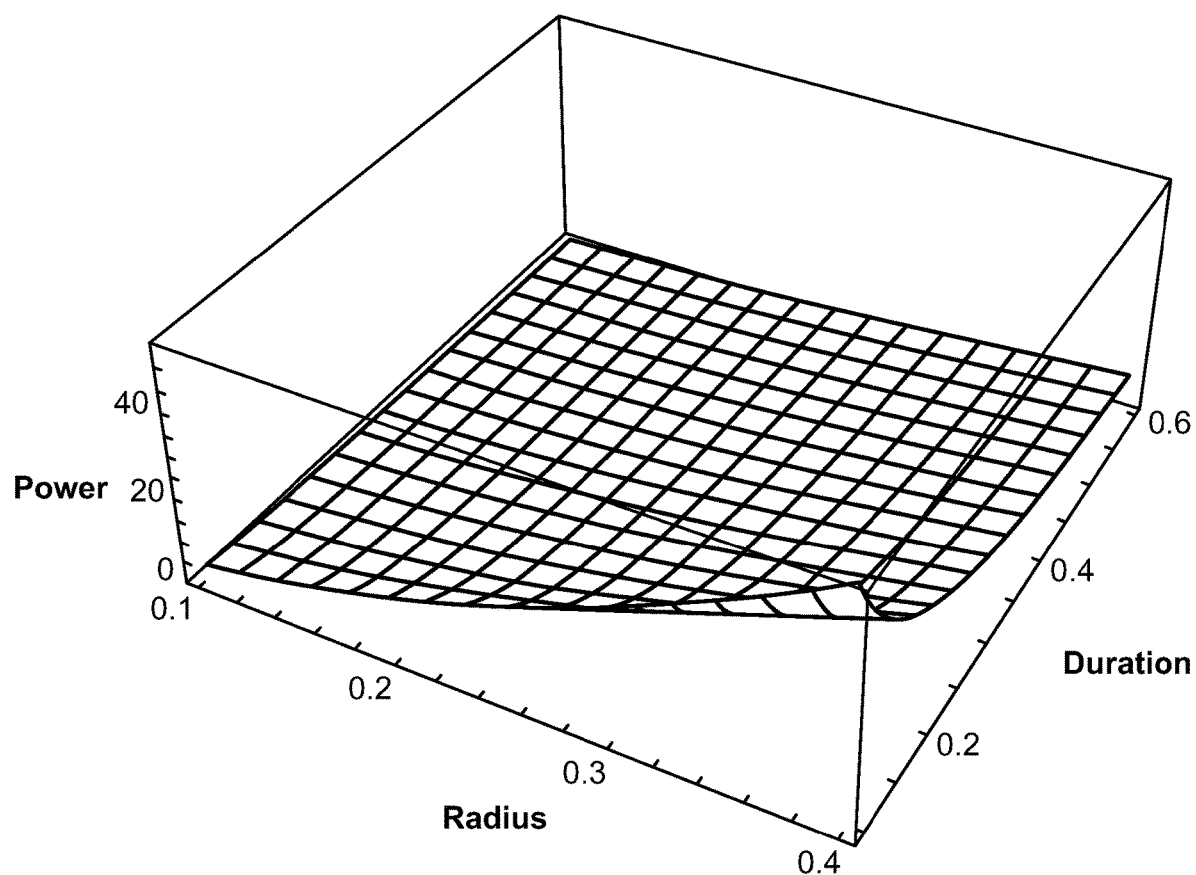
FIGS. 10 and 11 are graphs illustrating the average power of a laser source compared to a source radius and pulse train duration of the laser.
Figure 11:
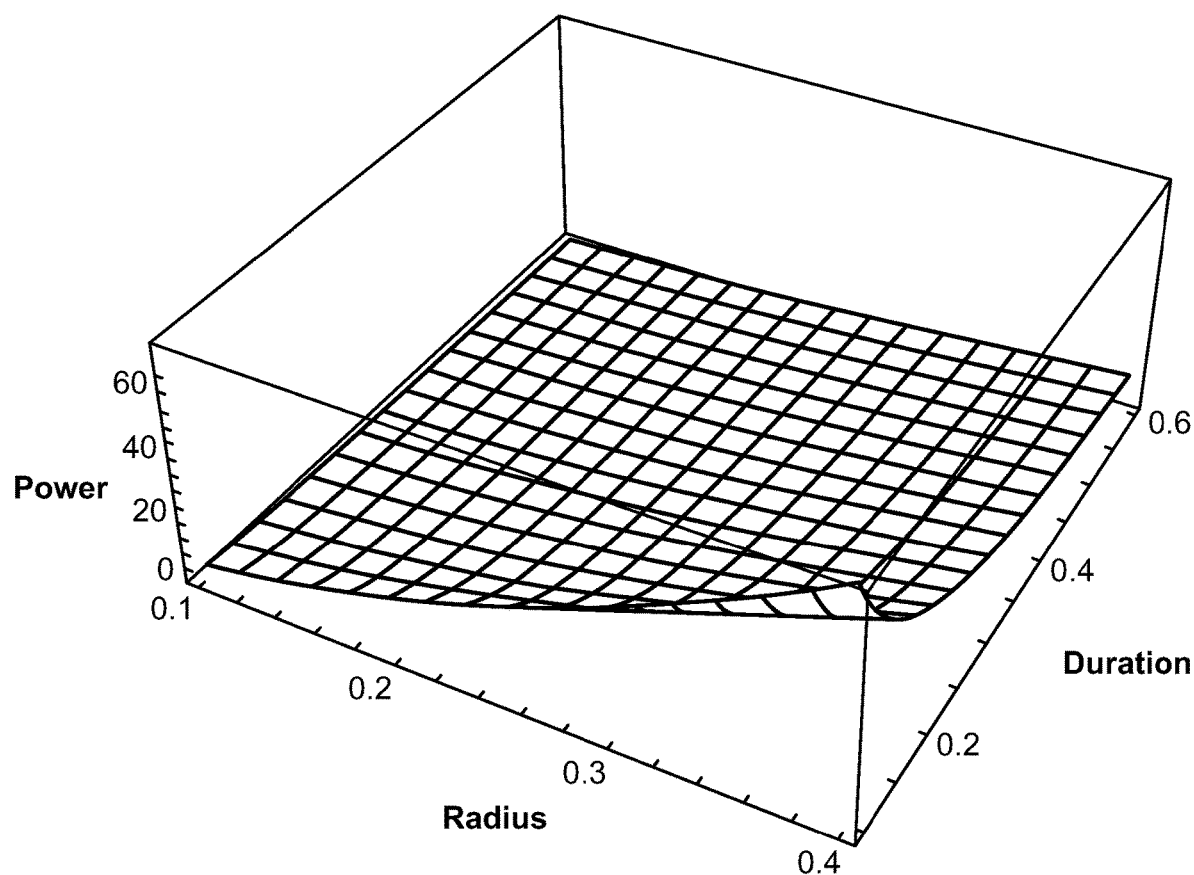

FIGS. 10 and 11 illustrate graphs showing the average power in watts as compared to the laser source radius (between 0.1 cm and 0.4 cm) and pulse train duration (between 0.1 and 0.6 seconds). FIG. 10 shows a wavelength of 880 nm, whereas FIG. 11 has a wavelength of 1000 nm. It can be seen in these figures that the required power decreases monotonically as the radius of the source decreases, as the total train duration increases, and as the wavelength decreases. The preferred parameters for the radius of the laser source is 1 mm-4 mm. For a wavelength of 880 nm, the minimum value of power is 0.55 watts, with a radius of the laser source being 1 mm, and the total pulse train duration being 600 milliseconds. The maximum value of power for the 880 nm wavelength is 52.6 watts when the laser source radius is 4 mm and the total pulse drain duration is 100 milliseconds. However, when selecting a laser having a wavelength of 1000 nm, the minimum power value is 0.77 watts with a laser source radius of 1 mm and a total pulse train duration of 600 milliseconds, and a maximum power value of 73.6 watts when the laser source radius is 4 mm and the total pulse duration is 100 milliseconds. The corresponding peak powers, during an individual pulse, are obtained from the average powers by dividing by the duty cycle.

The volume of the tissue region to be heated is determined by the wavelength, the absorption length in the relevant tissue, and by the beam width. The total pulse duration and the average laser power determine the total energy delivered to heat up the tissue, and the duty cycle of the pulse train gives the associated spike, or peak, power associated with the average laser power. Preferably, the pulsed energy source energy parameters are selected so that approximately 20 to 40 joules of energy is absorbed by each cubic centimeter of the target tissue.

The absorption length is very small in the thin melanin layer in the retinal pigmented epithelium. In other parts of the body, the absorption length is not generally that small. In wavelengths ranging from 400 nm to 2000 nm, the penetration depth and skin is in the range of 0.5 mm to 3.5 mm. The penetration depth into human mucous tissues in the range of 0.5 mm to 6.8 mm. Accordingly, the heated volume will be limited to the exterior or interior surface where the radiation source is placed, with a depth equal to the penetration depth, and a transverse dimension equal to the transverse dimension of the radiation source. Since the light beam energy source is used to treat diseased tissues near external surfaces or near internal accessible surfaces, a source radii of between 1 mm to 4 mm and operating a wavelength of 880 nm yields a penetration depth of approximately 2.5 mm and a wavelength of 1000 nm yields a penetration depth of approximately 3.5 mm.

Figure 12:
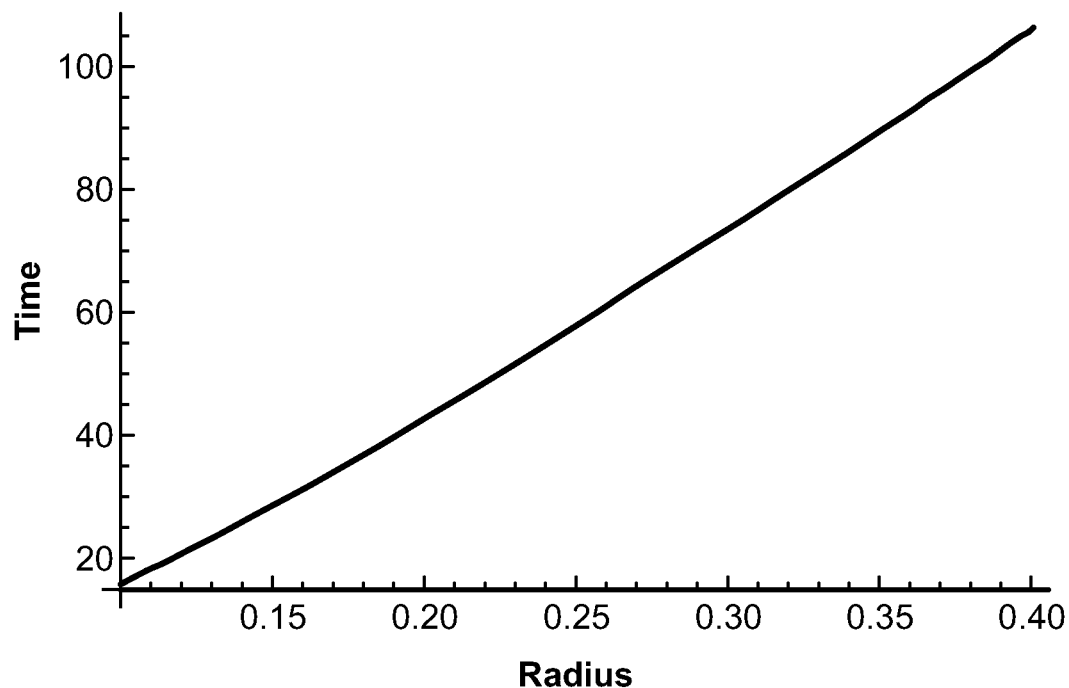
FIGS. 12 and 13 are graphs illustrating the time for the temperature for decay depending upon the laser source radius and wavelength.
Figure 13:
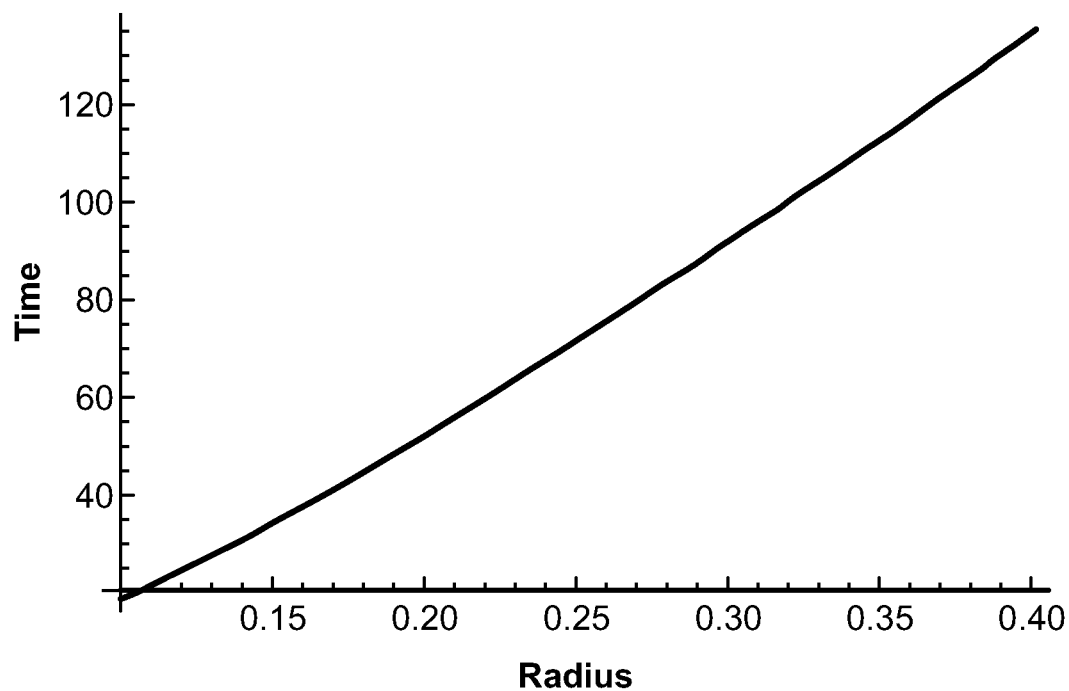

It has been determined that the target tissue can be heated to up to approximately 11° C. for a short period of time, such as less than one second, to create the therapeutic effect of the invention while maintaining the target tissue average temperature to a lower temperature range, such as less than 6° C. or even 1° C. or less over a prolonged period of time, such as several minutes. The selection of the duty cycle and the total pulse train duration provide time intervals in which the heat can dissipate. A duty cycle of less than 10%, and preferably between 2.5% and 5%, with a total pulse duration of between 100 milliseconds and 600 milliseconds has been found to be effective. FIGS. 12 and 13 illustrate the time to decay from 10° C. to 1° C. for a laser source having a radius of between 0.1 cm and 0.4 cm with the wavelength being 880 nm in FIG. 12 and 1000 nm in FIG. 13. It can be seen that the time to decay is less when using a wavelength of 880 nm, but either wavelength falls within the acceptable requirements and operating parameters to achieve the benefits of the present invention while not causing permanent tissue damage.

It has been found that the average temperature rise of the desired target region increasing at least 6° C. and up to 11° C., and preferably approximately 10° C., during the total irradiation period results in HSP activation. The control of the target tissue temperature is determined by choosing source and target parameters such that the Arrhenius integral for HSP activation is larger than 1, while at the same time assuring compliance with the conservative FDA/FCC requirements for avoiding damage or a damage Arrhenius integral being less than 1.

In order to meet the conservative FDA/FCC constraints to avoid permanent tissue damage, for light beams, and other electromagnetic radiation sources, the average temperature rise of the target tissue over any six-minute period is 1° C. or less. FIGS. 12 and 13 above illustrate the typical decay times required for the temperature in the heated target region to decrease by thermal diffusion from a temperature rise of approximately 10° C. to 1° C. as can be seen in FIG. 12 when the wavelength is 880 nm and the source diameter is 1 millimeter, the temperature decay time is 16 seconds. The temperature decay time is 107 seconds when the source diameter is 4 mm. As shown in FIG. 13, when the wavelength is 1000 nm, the temperature decay time is 18 seconds when the source diameter is 1 mm and 136 seconds when the source diameter is 4 mm. This is well within the time of the average temperature rise being maintained over the course of several minutes, such as 6 minutes or less. While the target tissue's temperature is raised, such as to approximately 10° C., very quickly, such as in a fraction of a second during the application of the energy source to the tissue, the relatively low duty cycle provides relatively long periods of time between the pulses of energy applied to the tissue and the relatively short pulse train duration ensure sufficient temperature diffusion and decay within a relatively short period of time comprising several minutes, such as 6 minutes or less, that there is no permanent tissue damage.

The parameters differ for the individual energy sources, including microwave, infrared lasers, radiofrequency and ultrasound, because the absorption properties of tissues differ for these different types of energy sources. The tissue water content can vary from one tissue type to another, however, there is an observed uniformity of the properties of tissues at normal or near normal conditions which has allowed publication of tissue parameters that are widely used by clinicians in designing treatments. Below are tables illustrating the properties of electromagnetic waves in biological media, with Table 1 relating to muscle, skin and tissues with high water content, and Table 2 relating to fat, bone and tissues with low water content.

TABLE 1

Properties of Electromagnetic Waves in Biological Media: Muscle, Skin, and Tissues with High Water Content

| Frequency (MHz) | Wavelength in Air (cm) | Dielectric Constant $\varepsilon_H$ | Conductivity $\varepsilon_H$ (mho/m) | Wavelength $\lambda_H$ (cm) | Depth of Penetration (cm) | Reflection Coefficient Air-Muscle Interface r | Reflection Coefficient Air-Muscle Interface ø | Reflection Coefficient Muscle-Fat Interface r | Reflection Coefficient Muscle-Fat Interface ø |
|---|---|---|---|---|---|---|---|---|---|
| 1 | 30000 | 2000 | 0.400 | 436 | 91.3 | 0.982 | +179 | | |
| 10 | 3000 | 160 | 0.625 | 118 | 21.6 | 0.956 | +178 | | |
| 27.12 | 1106 | 113 | 0.612 | 68.1 | 14.3 | 0.925 | +177 | 0.651 | −11.13 |
| 40.68 | 738 | 97.3 | 0.693 | 51.3 | 11.2 | 0.913 | +176 | 0.652 | −10.21 |
| 100 | 300 | 71.7 | 0.889 | 27 | 6.66 | 0.881 | +175 | 0.650 | −7.96 |
| 200 | 150 | 56.5 | 1.28 | 16.6 | 4.79 | 0.844 | +175 | 0.612 | −8.06 |
| 300 | 100 | 54 | 1.37 | 11.9 | 3.89 | 0.825 | +175 | 0.592 | −8.14 |
| 433 | 69.3 | 53 | 1.43 | 8.76 | 3.57 | 0.803 | +175 | 0.562 | −7.06 |
| 750 | 40 | 52 | 1.54 | 5.34 | 3.18 | 0.779 | +176 | 0.532 | −5.69 |
| 915 | 32.8 | 51 | 1.60 | 4.46 | 3.04 | 0.772 | +177 | 0.519 | −4.32 |
| 1500 | 20 | 49 | 1.77 | 2.81 | 2.42 | 0.761 | +177 | 0.506 | −3.66 |
| 2450 | 12.2 | 47 | 2.21 | 1.76 | 1.70 | 0.754 | +177 | 0.500 | −3.88 |
| 3000 | 10 | 46 | 2.26 | 1.45 | 1.61 | 0.751 | +178 | 0.495 | −3.20 |
| 5000 | 6 | 44 | 3.92 | 0.89 | 0.788 | 0.749 | +177 | 0.502 | −4.95 |
| 5800 | 5.17 | 43.3 | 4.73 | 0.775 | 0.720 | 0.746 | +177 | 0.502 | −4.29 |
| 8000 | 3.75 | 40 | 7.65 | 0.578 | 0.413 | 0.744 | +176 | 0.513 | −6.65 |
| 10000 | 3 | 39.9 | 10.3 | 0.464 | 0.343 | 0.743 | +176 | 0.518 | −5.95 |

TABLE 2

Properties of Electromagnetic Waves in Biological Media:
Fat, Bone, and Tissues with Low Water Content

| Frequency (MHz) | Wavelength in Air (cm) | Dielectric Constant $\epsilon_L$ | Conductivity $\sigma_L$, (mmho/m) | Wavelength $\lambda_L$ (cm) | Depth of Penetration (cm) | Reflection Coefficient Air-Fat Interface r | Reflection Coefficient Air-Fat Interface ø | Reflection Coefficient Fat-Muscle Interface r | Reflection Coefficient Fat-Muscle Interface ø |
|---|---|---|---|---|---|---|---|---|---|
| 1 | 30000 | | | | | | | | |
| 10 | 3000 | | | | | | | | |
| 27.12 | 1106 | 20 | 10.9-43.2 | 241 | 159 | 0.660 | +174 | 0.651 | +169 |
| 40.68 | 738 | 14.6 | 12.6-52.8 | 187 | 118 | 0.617 | +173 | 0.652 | +170 |
| 100 | 300 | 7.45 | 19.1-75.9 | 106 | 60.4 | 0.511 | +168 | 0.650 | +172 |
| 200 | 150 | 5.95 | 25.8-94.2 | 59.7 | 39.2 | 0.458 | +168 | 0.612 | +172 |
| 300 | 100 | 5.7 | 31.6-107 | 41 | 32.1 | 0.438 | +169 | 0.592 | +172 |
| 433 | 69.3 | 5.6 | 37.9-118 | 28.8 | 26.2 | 0.427 | +170 | 0.562 | +173 |
| 750 | 40 | 5.6 | 49.8-138 | 16.8 | 23 | 0.415 | +173 | 0.532 | +174 |
| 915 | 32.8 | 5.6 | 55.6-147 | 13.7 | 17.7 | 0.417 | +173 | 0.519 | +176 |
| 1500 | 20 | 5.6 | 70.8-171 | 8.41 | 13.9 | 0.412 | +174 | 0.506 | +176 |
| 2450 | 12.2 | 5.5 | 96.4-213 | 5.21 | 11.2 | 0.406 | +176 | 0.500 | +176 |
| 3000 | 10 | 5.5 | 110-234 | 4.25 | 9.74 | 0.406 | +176 | 0.495 | +177 |
| 5000 | 6 | 5.5 | 162-309 | 2.63 | 6.67 | 0.393 | +176 | 0.502 | +175 |
| 5900 | 5.17 | 5.05 | 186-338 | 2.29 | 5.24 | 0.388 | +176 | 0.502 | +176 |
| 8000 | 3.75 | 4.7 | 255-431 | 1.73 | 4.61 | 0.371 | +176 | 0.513 | +173 - |
| 10000 | 3 | 4.5 | 324-549 | 1.41 | 3.39 | 0.363 | +175 | 0.518 | +174,- |

The absorption lengths of radiofrequency in body tissue are long compared to body dimensions. Consequently, the heated region is determined by the dimensions of the coil that is the source of the radiofrequency energy rather than by absorption lengths. Long distances r from a coil the magnetic (near) field from a coil drops off as $1/r^3$. At smaller distances, the electric and magnetic fields can be expressed in terms of the vector magnetic potential, which in turn can be expressed in closed form in terms of elliptic integrals of the first and second kind. The heating occurs only in a region that is comparable in size to the dimensions of the coil source itself. Accordingly, if it is desired to preferentially heat a region characterized by a radius, the source coil will be chosen to have a similar radius. The heating drops off very rapidly outside of a hemispherical region of radius because of the $1/r^3$ drop off of the magnetic field. Since it is proposed to use the radiofrequency the diseased tissue accessible only externally or from inner cavities, it is reasonable to consider a coil radii of between approximately 2 to 6 mm.

The radius of the source coil(s) as well as the number of ampere turns (NI) in the source coils give the magnitude and spatial extent of the magnetic field, and the radiofrequency is a factor that relates the magnitude of the electric field to the magnitude of the magnetic field. The heating is proportional to the product of the conductivity and the square of the electric field. For target tissues of interest that are near external or internal surfaces, the conductivity is that of skin and mucous tissue. The duty cycle of the pulse train as well as the total train duration of a pulse train are factors which affect how much total energy is delivered to the tissue.

Figure 14:
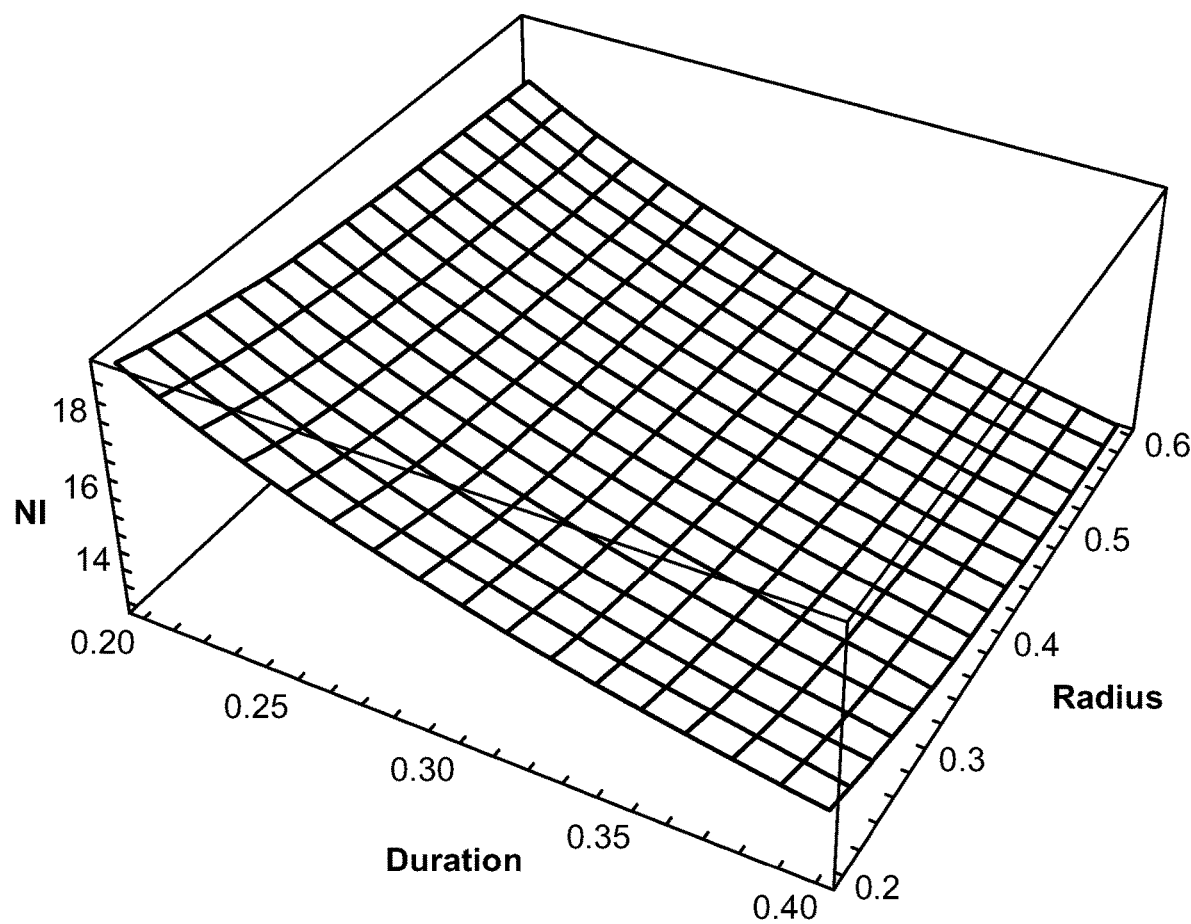
FIG. 14-17 are graphs illustrating peak ampere turns for various radiofrequencies, duty cycles and coil radii.
Figure 15:
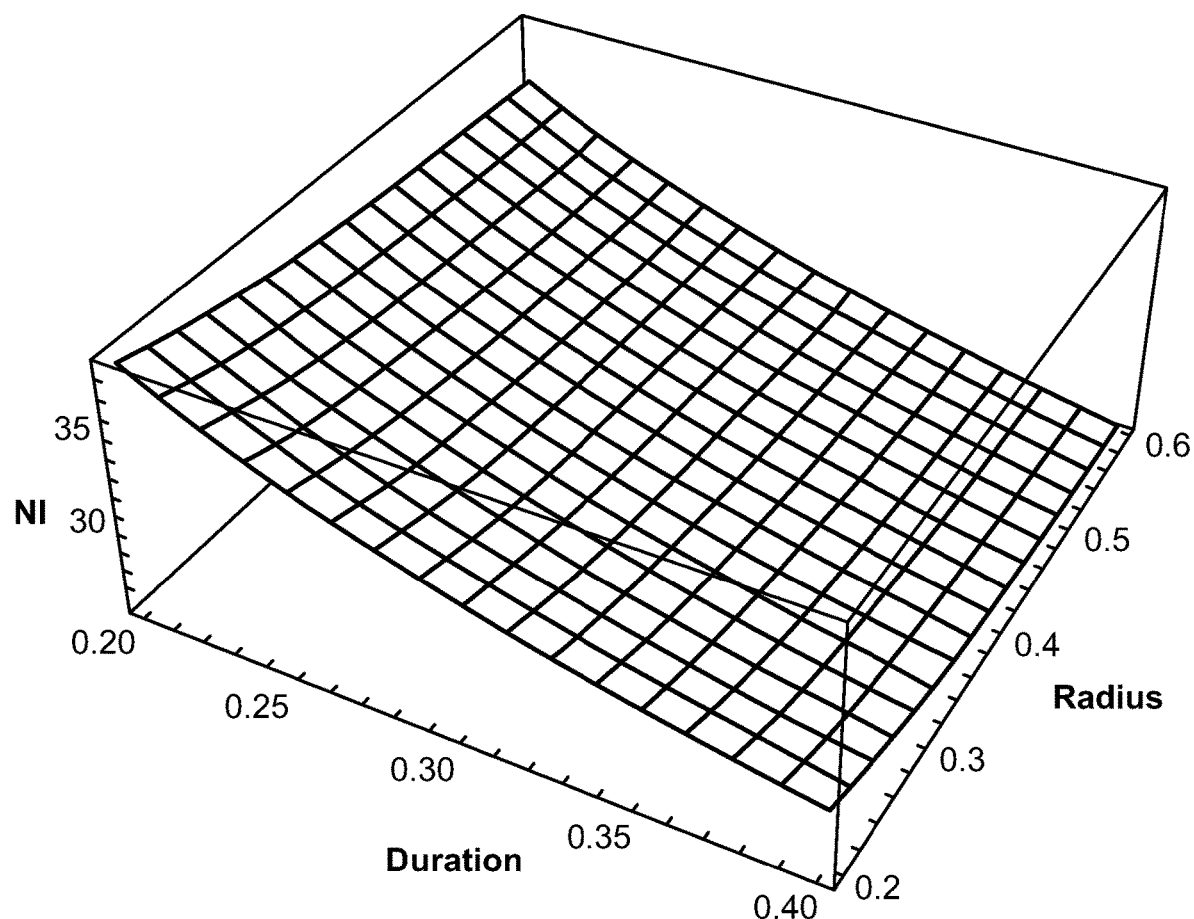
Figure 16:
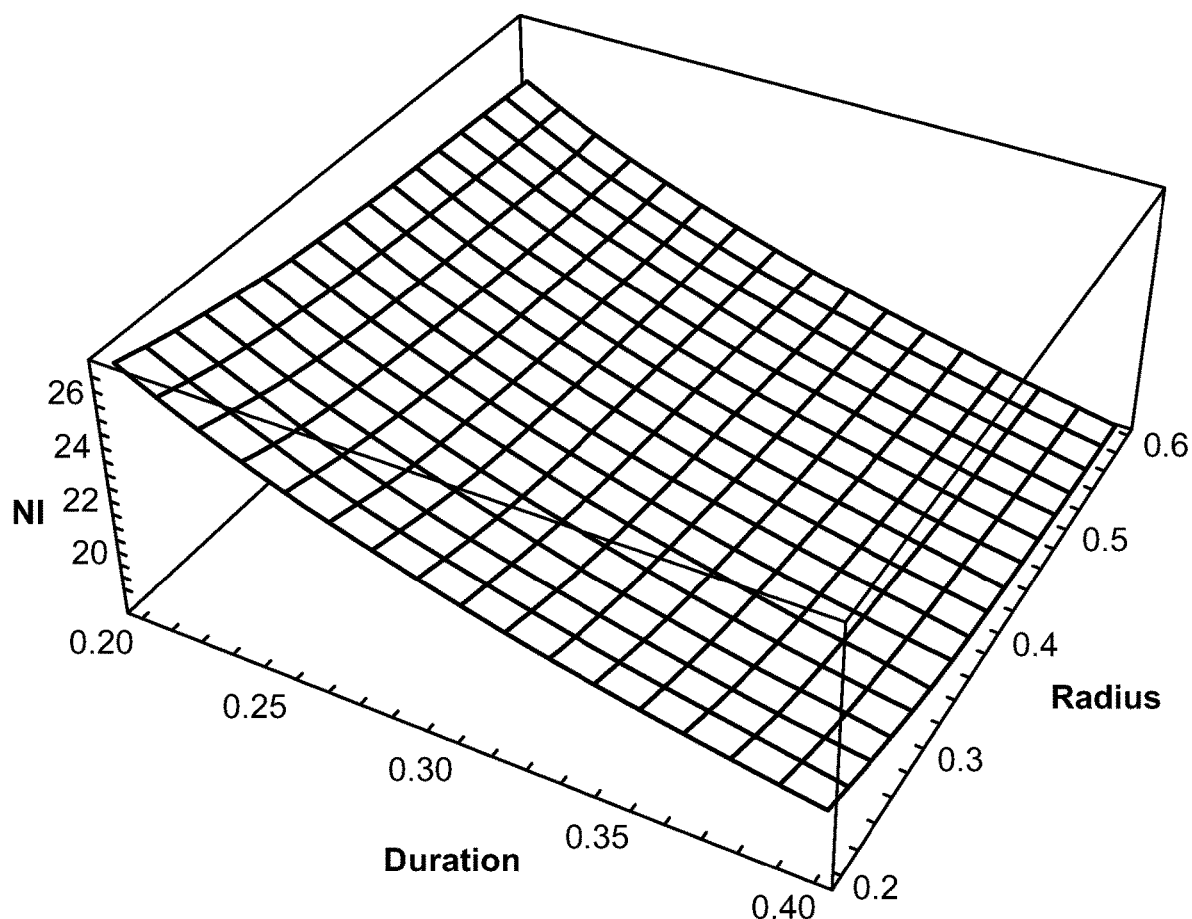
Figure 17:
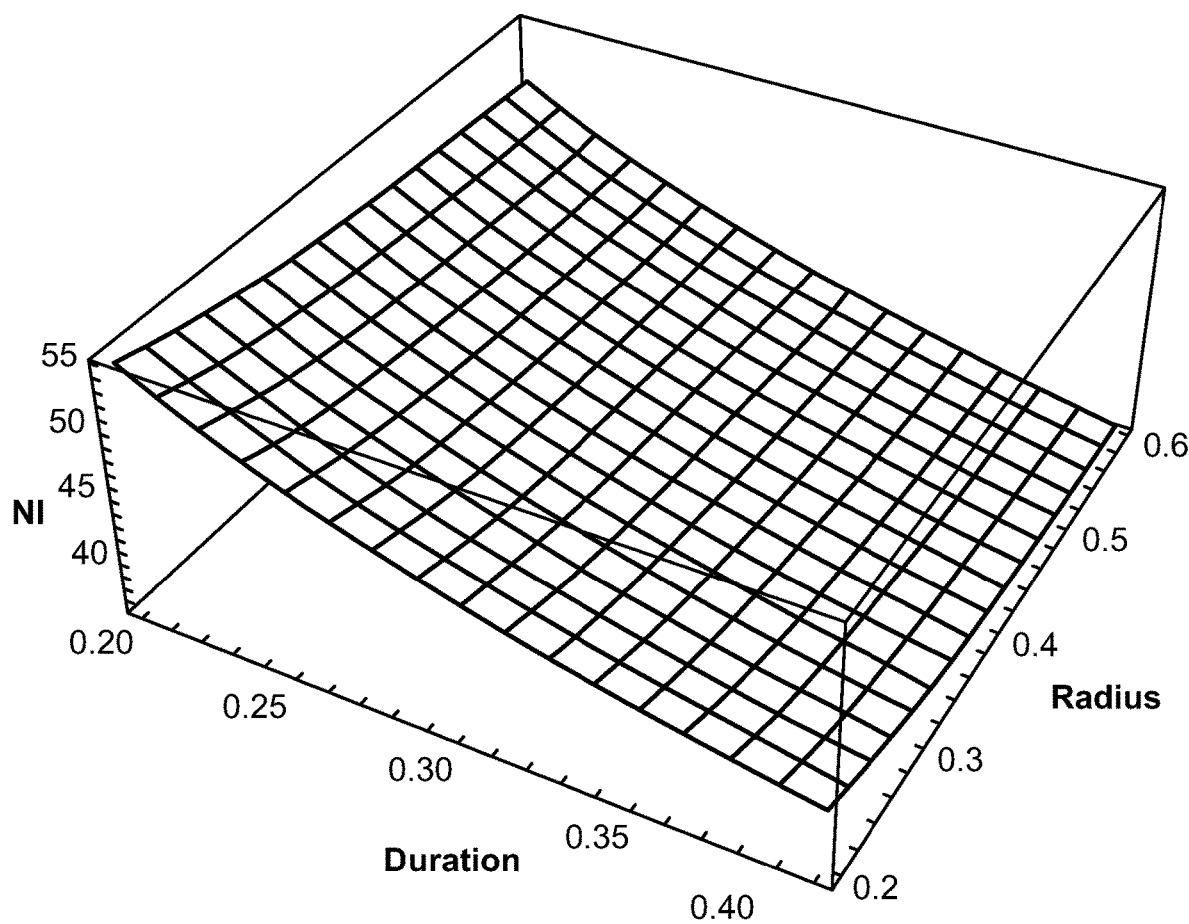

Preferred parameters for a radiofrequency energy source have been determined to be a coil radii between 2 and 6 mm, radiofrequencies in the range of 3-6 MHz, total pulse train durations of 0.2 to 0.4 seconds, and a duty cycle of between 2.5% and 5%. FIGS. 14-17 show how the number of ampere turns varies as these parameters are varied in order to give a temperature rise that produces an Arrhenius integral of approximately one or unity for HSP activation. With reference to FIG. 14, for an RF frequency of 6 MHz, a pulse train duration of between 0.2 and 0.4 seconds, a coil radius between 0.2 and 0.6 cm, and a duty cycle of 5%, the peak ampere turns (NI) is 13 at the 0.6 cm coil radius and 20 at the 0.2 cm coil radius. For a 3 MHz frequency, as illustrated in FIG. 15, the peak ampere turns is 26 when the pulse train duration is 0.4 seconds and the coil radius is 0.6 cm and the duty cycle is 5%. However, with the same 5% duty cycle, the peak ampere turns is 40 when the coil radius is 0.2 cm and the pulse train duration is 0.2 seconds. A duty cycle of 2.5% is used in FIGS. 16 and 17. This yields, as illustrated in FIG. 16, 18 amp turns for a 6 MHz radiofrequency having a coil radius of 0.6 cm and a pulse train duration of 0.4 seconds, and 29 amp turns when the coil radius is only 0.2 cm and the pulse train duration is 0.2 seconds. With reference to FIG. 17, with a duty cycle of 2.5% and a radiofrequency of 3 MHz, the peak ampere turns is 36 when the pulse train duration is 0.4 seconds and the coil radius is 0.6 cm, and 57 amp turns when the pulse train duration is 0.2 seconds and the coil radius is 0.2 cm.

Figure 18:
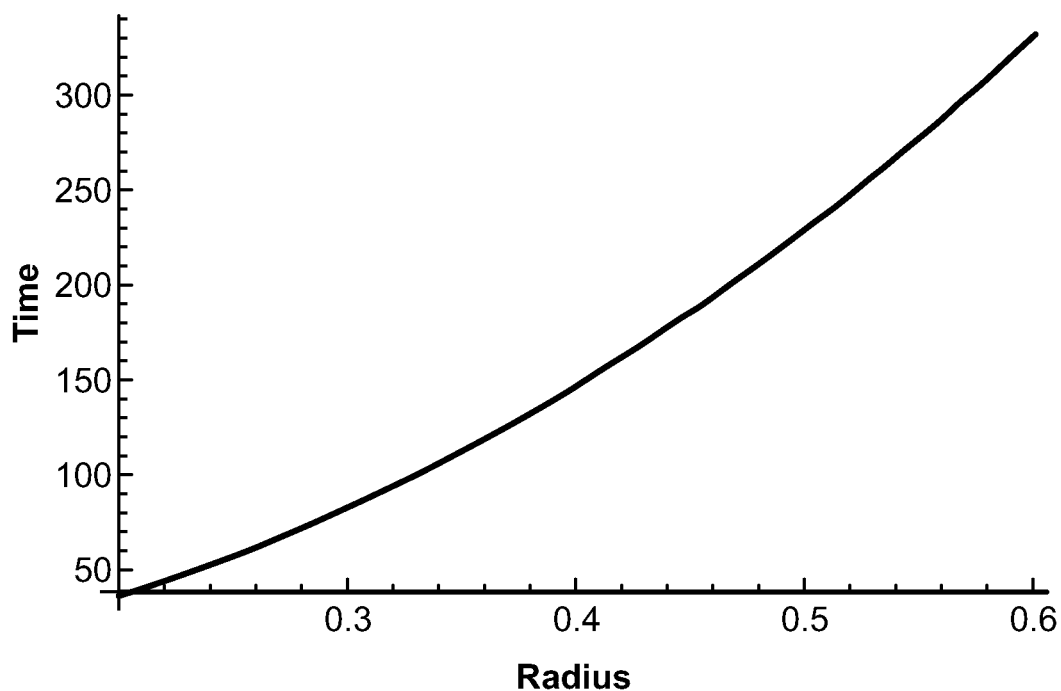
FIG. 18 is a graph depicting the time for temperature rise to decay compared to radiofrequency coil radius.

The time, in seconds, for the temperature rise to decay from approximately 10° C. to approximately 1° C. for coil radii between 0.2 cm and 0.6 cm is illustrated for a radiofrequency energy source in FIG. 18. The temperature decay time is approximately 37 seconds when the radiofrequency coil radius is 0.2 cm, and approximately 233 seconds when the radiofrequency coil radius is 0.5 cm. When the radiofrequency coil radius is 0.6 cm, the decay time is approximately 336 seconds, which is still within the acceptable range of decay time, but at an upper range thereof.

Microwaves are another electromagnetic energy source which can be utilized in accordance with the present invention. The frequency of the microwave determines the tissue penetration distance. The gain of a conical microwave horn is large compared to the microwave wavelength, indicating under those circumstances that the energy is radiated mostly in a narrow forward load. Typically, a microwave source used in accordance with the present invention has a linear dimension on the order of a centimeter or less, thus the source is smaller than the wavelength, in which case the microwave source can be approximated as a dipole antenna. Such small microwave sources are easier to insert into internal body cavities and can also be used to radiate external surfaces. In that case, the heated region can be approximated by a hemisphere with a radius equal to the absorption length of the microwave in the body tissue being treated. As the microwaves are used to treat tissue near external surfaces or surfaces accessible from internal cavities, frequencies in the 10-20 GHz range are used, wherein the corresponding penetration distances are only between approximately 2 and 4 mm.

The temperature rise of the tissue using a microwave energy source is determined by the average power of the microwave and the total pulse train duration. The duty cycle of the pulse train determines the peak power in a single pulse in a train of pulses. As the radius of the source is taken to be less than approximately 1 centimeter, and frequencies between 10 and 20 GHz are typically used, a resulting pulse train duration of 0.2 and 0.6 seconds is preferred.

The required power decreases monotonically as the train duration increases and as the microwave frequency increases. For a frequency of 10 GHz, the average power is 18 watts when the pulse train duration is 0.6 seconds, and 52 watts when the pulse train duration is 0.2 seconds. For a 20 GHz microwave frequency, an average power of 8 watts is used when the pulse train is 0.6 seconds, and can be 26 watts when the pulse train duration is only 0.2 seconds. The corresponding peak power are obtained from the average power simply by dividing by the duty cycle.

Figure 19:
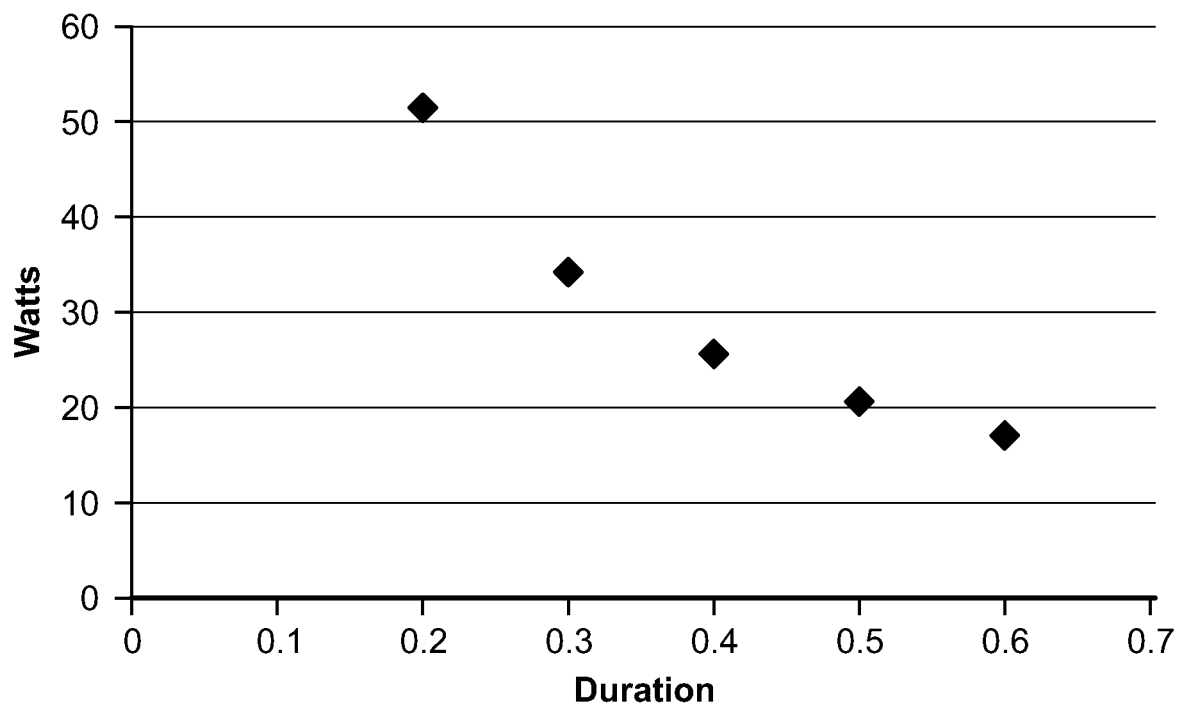
FIGS. 19 and 20 and graphs depicting the average microwave power compared to microwave frequency and pulse train duration.
Figure 20:
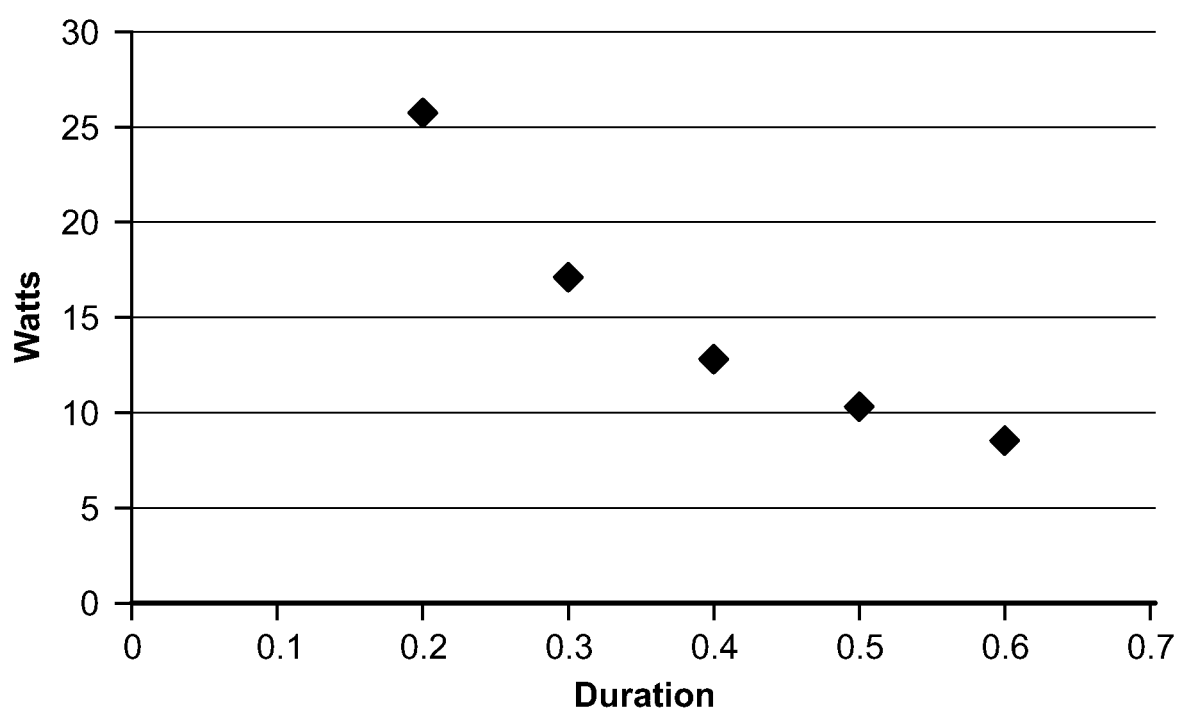

With reference now to FIG. 19, a graph depicts the average microwave power in watts of a microwave having a frequency of 10 GHz and a pulse train duration from between 0.2 seconds and 0.6 seconds. FIG. 20 is a similar graph, but showing the average microwave power for a microwave having a frequency of 20 GHz. Thus, it will be seen that the average microwave source power varies as the total train duration and microwave frequency vary. The governing condition, however, is that the Arrhenius integral for HSP activation in the heated region is approximately 1.

Figure 21:
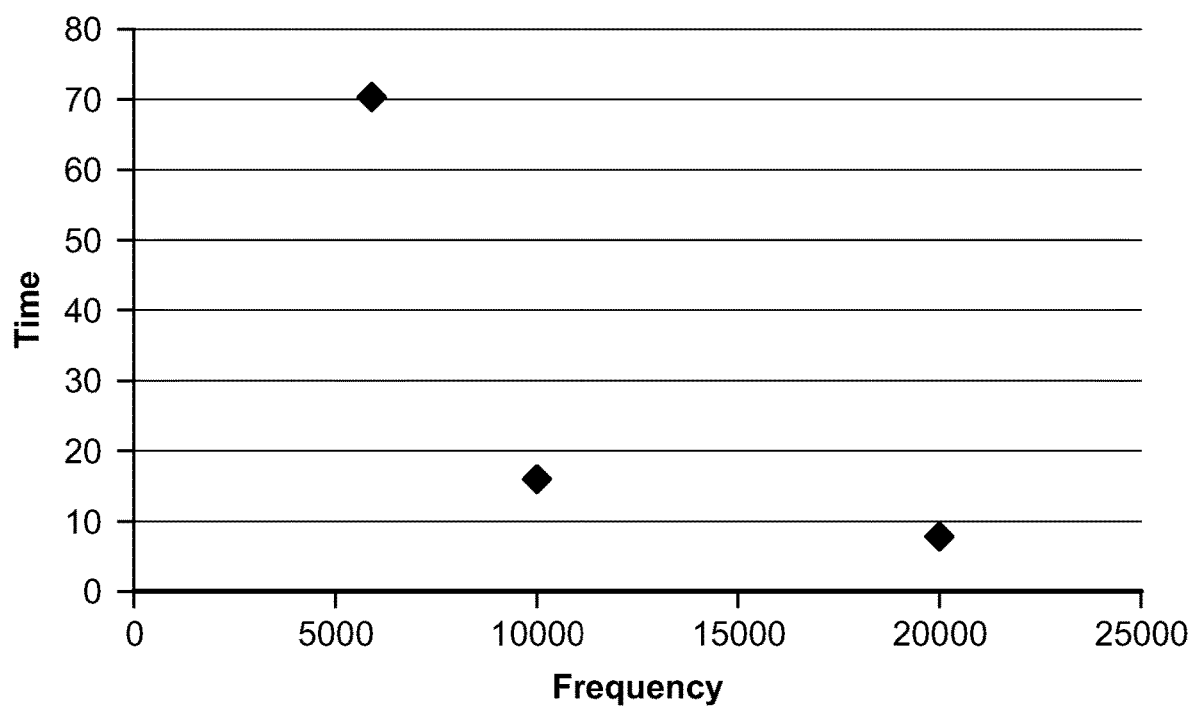
FIG. 21 is a graph depicting the time for the temperature to decay for various microwave frequencies.

With reference to FIG. 21, a graph illustrates the time, in seconds, for the temperature to decay from approximately 10° C. to 1° C. compared to microwave frequencies between 58 MHz and 20000 MHz. The minimum and maximum temperature decay for the preferred range of microwave frequencies are 8 seconds when the microwave frequency is 20 GHz, and 16 seconds when the microwave frequency is 10 GHz.

Utilizing ultrasound as an energy source enables heating of surface tissue, and tissues of varying depths in the body, including rather deep tissue. The absorption length of ultrasound in the body is rather long, as evidenced by its widespread use for imaging. Accordingly, ultrasound can be focused on target regions deep within the body, with the heating of a focused ultrasound beam concentrated mainly in the approximately cylindrical focal region of the beam. The heated region has a volume determined by the focal waist of the airy disc and the length of the focal waist region, that is the confocal parameter. Multiple beams from sources at different angles can also be used, the heating occurring at the overlapping focal regions.

For ultrasound, the relevant parameters for determining tissue temperature are frequency of the ultrasound, total train duration, and transducer power when the focal length and diameter of the ultrasound transducer is given. The frequency, focal length, and diameter determine the volume of the focal region where the ultrasound energy is concentrated. It is the focal volume that comprises the target volume of tissue for treatment. Transducers having a diameter of approximately 5 cm and having a focal length of approximately 10 cm are readily available. Favorable focal dimensions are achieved when the ultrasound frequency is between 1 and 5 MHz, and the total train duration is 0.1 to 0.5 seconds. For example, for a focal length of 10 cm and the transducer diameter of 5 cm, the focal volumes are 0.02 cc at 5 MHz and 2.36 cc at 1 MHz.

Figure 22:
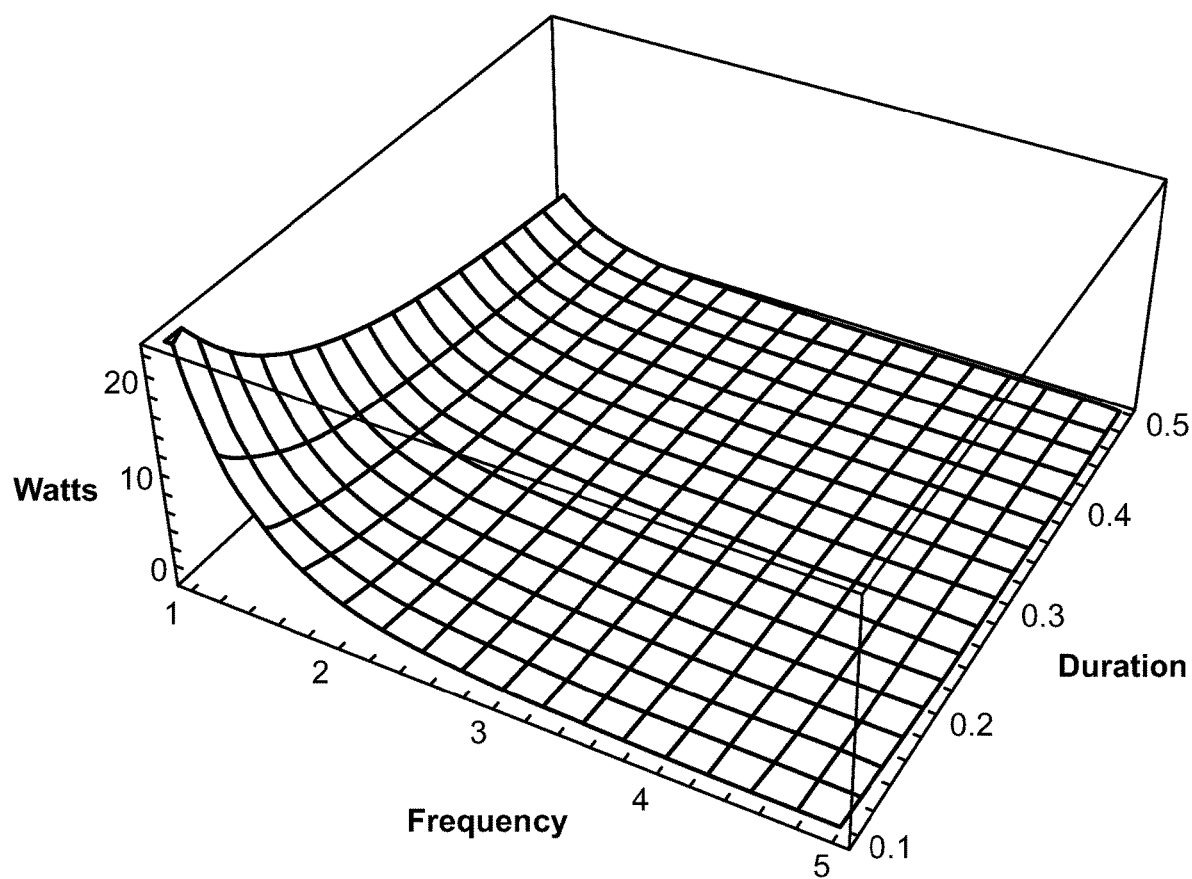
FIG. 22 is a graph depicting the average ultrasound source power compared to frequency and pulse train duration.

With reference now to FIG. 22, a graph illustrates the average source power in watts compared to the frequency (between 1 MHz and 5 MHz), and the pulse train duration (between 0.1 and 0.5 seconds). A transducer focal length of 10 cm and a source diameter of 5 cm have been assumed. The required power to give the Arrhenius integral for HSP activation of approximately 1 decreases monotonically as the frequency increases and as the total train duration increases. Given the preferred parameters, the minimum power for a frequency of 1 GHz and a pulse train duration of 0.5 seconds is 5.72 watts, whereas for the 1 GHz frequency and a pulse train duration of 0.1 seconds the maximum power is 28.6 watts. For a 5 GHz frequency, 0.046 watts is required for a pulse train duration of 0.5 seconds, wherein 0.23 watts is required for a pulse train duration of 0.1 seconds. The corresponding peak power during an individual pulse is obtained simply by dividing by the duty cycle.

Figure 23:
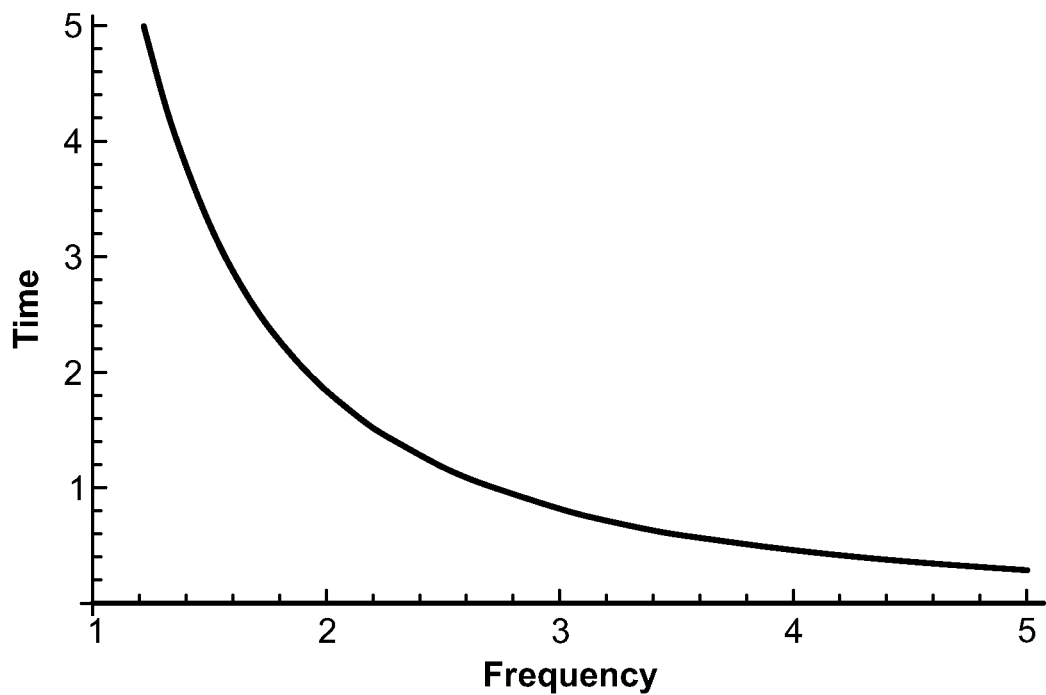
FIGS. 23 and 24 are graphs depicting the time for temperature decay for various ultrasound frequencies.
Figure 24:
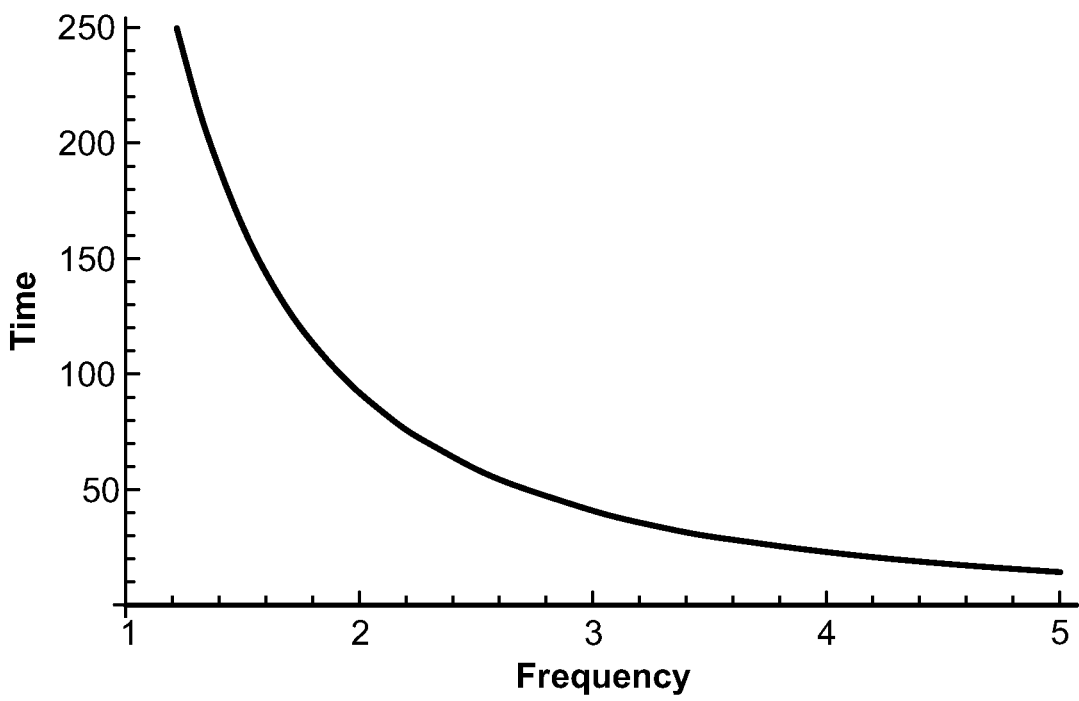

FIG. 23 illustrates the time, in seconds, for the temperature to diffuse or decay from 10° C. to 6° C. when the ultrasound frequency is between 1 and 5 MHz. FIG. 24 illustrates the time, in seconds, to decay from approximately 10° C. to approximately 1° C. for ultrasound frequencies from 1 to 5 MHz. For the preferred focal length of 10 cm and the transducer diameter of 5 cm, the maximum time for temperature decay is 366 seconds when the ultrasound frequency is 1 MHz, and the minimum temperature decay is 15 seconds when the microwave frequency is 5 MHz. As the FDA only requires the temperature rise be less than 6° C. for test times of minutes, the 366 second decay time at 1 MHz to get to a rise of 1° C. over the several minutes is allowable. As can be seen in FIGS. 23 and 24, the decay times to a rise of 6° C. are much smaller, by a factor of approximately 70, than that of 1° C.

Figure 25:
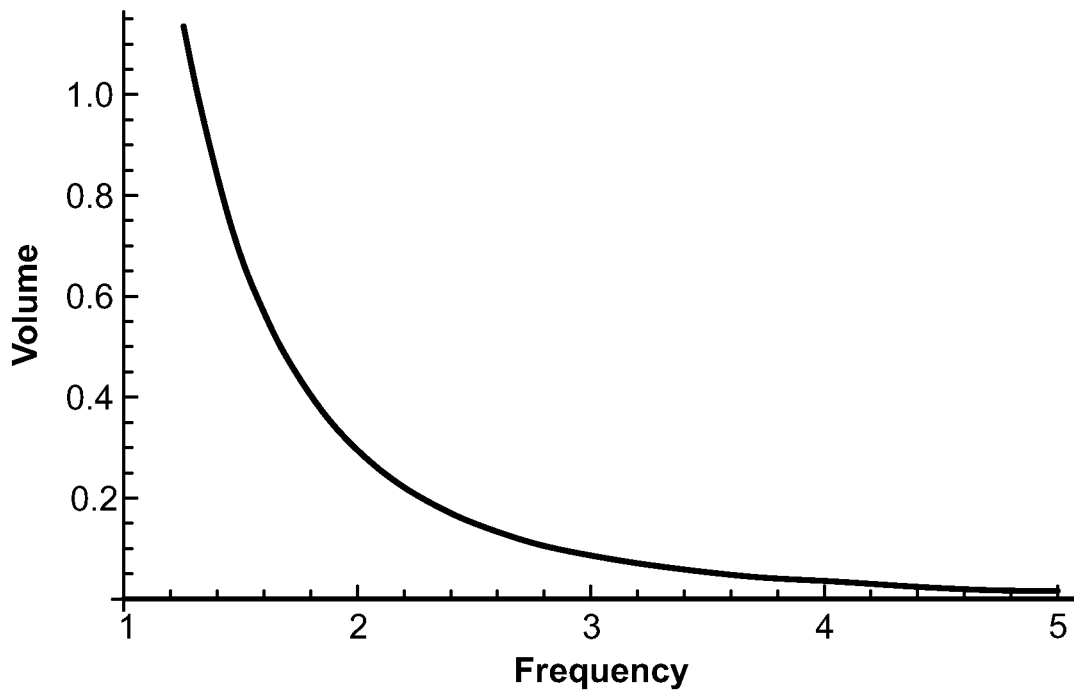
FIG. 25 is a graph depicting the volume of focal heated region compared to ultrasound frequency.

FIG. 25 illustrates the volume of focal heated region, in cubic centimeters, as compared to ultrasound frequencies from between 1 and 5 MHz. Considering ultrasound frequencies in the range of 1 to 5 MHz, the corresponding focal sizes for these frequencies range from 3.7 mm to 0.6 mm, and the length of the focal region ranges from 5.6 cm to 1.2 cm. The corresponding treatment volumes range from between approximately 2.4 cc and 0.02 cc.

Examples of parameters giving a desired HSP activation Arrhenius integral greater than 1 and damage Arrhenius integral less than 1 is a total ultrasound power between 5.8-17 watts, a pulse duration of 0.5 seconds, an interval between pulses of 5 seconds, with total number of pulses 10 within the total pulse stream time of 50 seconds. The target treatment volume would be approximately 1 mm on a side. Larger treatment volumes could be treatable by an ultrasound system similar to a laser diffracted optical system, by applying ultrasound in multiple simultaneously applied adjacent but separated and spaced columns. The multiple focused ultrasound beams converge on a very small treatment target within the body, the convergence allowing for a minimal heating except at the overlapping beams at the target. This area would be heated and stimulate the activation of HSPs and facilitate protein repair by transient high temperature spikes. However, given the pulsating aspect of the invention as well as the relatively small area being treated at any given time, the treatment is in compliance with FDA/FCC requirements for long term (minutes) average temperature rise <1K. An important distinction of the invention from existing therapeutic heating treatments for pain and muscle strain is that there are no high T spikes in existing techniques, and these are required for efficiently activating HSPs and facilitating protein repair to provide healing at the cellular level.

The pulse train mode of energy delivery has a distinct advantage over a single pulse or gradual mode of energy delivery, as far as the activation of remedial HSPs and the facilitation of protein repair is concerned. There are two considerations that enter into this advantage:

First, a big advantage for HSP activation and protein repair in a PEMR energy delivery mode comes from producing a spike temperature of the order of 10° C. This large rise in temperature has a big impact on the Arrhenius integrals that describe quantitatively the number of HSPs that are activated and the rate of water diffusion into the proteins that facilitates protein repair. This is because the temperature enters into an exponential that has a big amplification effect.

It is important that the temperature rise not remain at the high value (10° C. or more) for long, because then it would violate the FDA and FCC requirements that over periods of minutes the average temperature rise must be less than 1° C. (or in the case of ultrasound 6°).

An SDM or other PEMR mode of energy delivery uniquely satisfies both of these foregoing considerations by judicious choice of the power, pulse time, pulse interval, and the volume of the target region to be treated. The volume of the treatment region enters because the temperature must decay from its high value of the order of 10° C. fairly rapidly in order for the long term average temperature rise not to exceed the long term FDA/FCC limit of 6° C. for ultrasound frequencies and 1° C. or less for electromagnetic radiation energy sources.

For a region of linear dimension L, the time that it takes the peak temperature to e-fold in tissue is roughly $L^2/16D$, where $D=0.00143$ cm$^2$/sec is the typical heat diffusion coefficient. For example, if L=1 mm, the decay time is roughly 0.4 sec. Accordingly, for a region 1 mm on a side, a train consisting of 10 pulses each of duration 0.5 seconds, with an interval between pulses of 5 second can achieve the desired momentary high rise in temperature while still not exceeding an average long term temperature rise of 1° C. This is demonstrated further below.

The limitation of heated volume is the reason why RF electromagnetic radiation is not as good of a choice for treatment of regions deep with the body as ultrasound. The long skin depths (penetration distances) and Ohmic heating all along the skin depth results in a large heated volume whose thermal inertia does not allow both the attainment of a high spike temperature that activates HSPs and facilitates protein repair, and the rapid temperature decay that satisfies the long term FDA and FCC limit on average temperature rise.

Ultrasound has already been used to therapeutically heat regions of the body to ease pain and muscle strain. However, the heating has not followed the protocol of the invention and does not have the temperature spikes that are responsible for the excitation of HSPs.

Consider, then, a group of focused ultrasound beams that are directed at a target region deep within the body. To simplify the mathematics, suppose that the beams are replaced by a single source with a spherical surface shape that is focused on the center of the sphere. The absorption lengths of ultrasound can be fairly long. Table 3 below shows typical absorption coefficients for ultrasound at 1 MHz. The absorption coefficients are roughly proportional to the frequency.

TABLE 3

Typical absorption coefficients for 1 MHz ultrasound in body tissue:

| Body Tissue | Attenuation Coefficient at 1 MHz (cm$^{-1}$) |
|---|---|
| Water | 0.00046 |
| Blood | 0.0415 |
| Fat | 0.145 |
| Liver | 0.115-0.217 |
| Kidney | 0.23 |
| Muscle | 0.3-0.76 |
| Bone | 1.15 |

Assuming that the geometric variation of the incoming radiation due to the focusing dominates any variation due to attenuation, the intensity of the incoming ultrasound at a distance r from the focus can be written approximately as:

$$I(r)=P/(4\pi r^2) \quad [1]$$

where P denotes the total ultrasound power.

The temperature rise at the end of a short pulse of duration $t_p$ at r is then $$dT(t_p)=P\alpha t_p/(4\pi C_v r^2) \quad [2]$$

where $\alpha$ is the absorption coefficient and $C_v$ is the specific volume heat capacity. This will be the case until the r is reached at which the heat diffusion length at $t_p$ becomes comparable to r, or the diffraction limit of the focused beam is reached. For smaller r, the temperature rise is essentially independent of r. As an example, suppose the diffraction limit is reached at a radial distance that is smaller than that determined by heat diffusion. Then $$r_{dif}=(4Dt_p)^{1/2} \quad [3]$$

where D is the heat diffusion coefficient, and for $r<r_{dif}$ the temperature rise at $t_p$ is $$dT(r_{dif},t_p)=3P\alpha/(8\pi C_v D) \text{ when } r<r_{dif} \quad [4]$$

Thus, at the end of the pulse, we can write for the temperature rise:

$$dT_p(r)=\{P\alpha t_p/(4\pi C_v)\}[(6/r_{dif}^2)U\{r_{dif}-r\}/r^2)U(r-r_{dif})] \quad [5]$$

On applying the Green's function for the heat diffusion equation, $$G(r,t)=(4\Omega Dt)^{-3/2}\exp[-r^2/(4Dt)] \quad [6]$$

to this initial temperature distribution, we find that the temperature dT(t) at the focal point r=0 at a time t is $$dT(t)=[dT_o/\{(\tfrac{1}{2})+(\pi^{1/2}/6)\}][(\tfrac{1}{2})(t_p/t)^{3/2}+(\pi^{1/2}/6)(t_p/t)] \quad [7]$$

with $$dT_o=3P\alpha/(8\pi C_v D) \quad [8]$$

Figure 26:
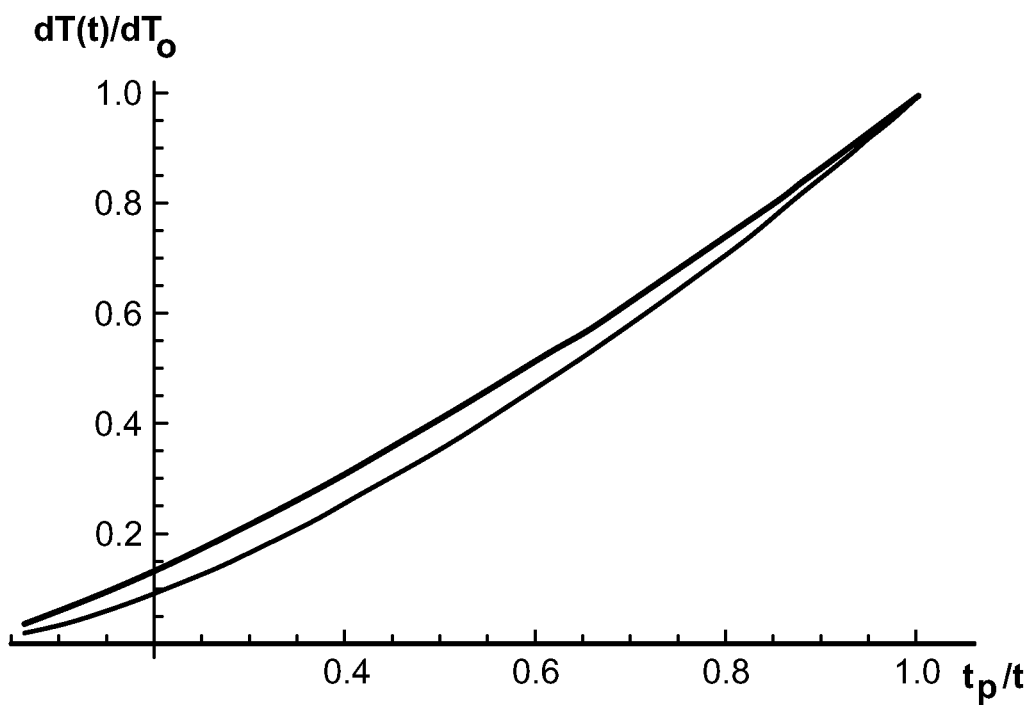
FIG. 26 is a graph comparing equations for temperature over pulse durations for an ultrasound energy source.

A good approximation to eq. [7] is provided by:

$$dT(t)\approx dT_o(t_p/t)^{3/2} \quad [9]$$

as can be seen in FIG. 26, which is a comparison of eqs. [7] and [9] for $dT(t)/dT_o$ at the target treatment zone. The bottom curve is the approximate expression of eq [9].

The Arrhenius integral for a train of N pulses can now be evaluated with the temperature rise given by eq. [9]. In this expression, $$dT_N(t)=\Sigma dT(t-nt_I) \quad [11]$$

where dT(t−nt$_I$) is the expression of eq. [9] with t replaced by t−nt$_I$ and with t$_I$ designating the interval between pulses.

The Arrhenius integral can be evaluated approximately by dividing the integration interval into the portion where the temperature spikes occur and the portion where the temperature spike is absent. The summation over the temperature spike contribution can be simplified by applying Laplace's end point formula to the integral over the temperature spike. In addition, the integral over the portion when the spikes are absent can be simplified by noting that the non-spike temperature rise very rapidly reaches an asymptotic value, so that a good approximation is obtained by replacing the varying time rise by its asymptotic value. When these approximations are made, eq. [10] becomes:

$$\Omega = AN[\{t_p(2k_BT_o^2/(3EdT_o)\}\exp[-(E/k_B)1/(T_o+dT_o+dT_N(Nt_I))]+\exp[-(E/k_B)1/(T_o+dT_N(Nt_I))]] \quad [12]$$

where $$dT_N(Nt_I) \approx 2.5 dT_o(t_p/t_I)^{3/2} \quad [13]$$

(The 2.5 in eq. [13] arises from the summation over n of $(N-n)^{-3/2}$ and is the magnitude of the harmonic number (N,3/2) for typical N of interest).

It is interesting to compare this expression with that for SDM applied to the retina. The first term is very similar to that from the spike contribution in the retina case, except that the effective spike interval is reduced by a factor of 3 for this 3D converging beam case. The second term, involving $dT_N(Nt_I)$ is much smaller than in the retina case. There the background temperature rise was comparable in magnitude to the spike temperature rise. But here in the converging beam case, the background temperature rise is much smaller by the ratio $(t_p/t_I)^{3/2}$. This points up the importance of the spike contribution to the activation or production of HSP's and the facilitation of protein repair, as the background temperature rise which is similar to the rise in a continuous ultrasound heating case is insignificant compared to the spike contribution. At the end of the pulse train, even this low background temperature rise rapidly disappears by heat diffusion.

Figure 27:
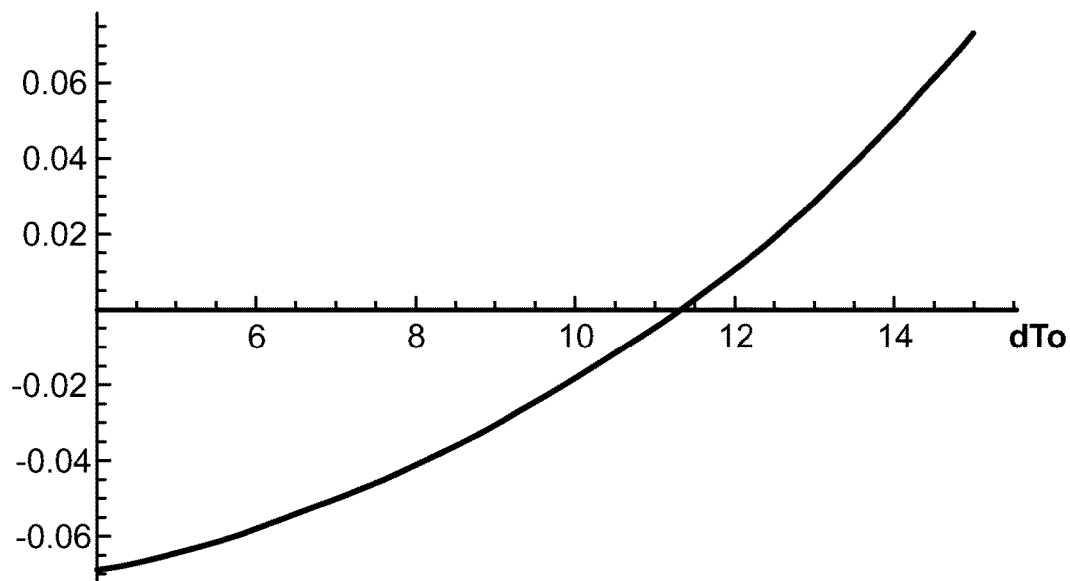
FIGS. 27 and 28 are graphs illustrating the magnitude of the logarithm of damage and HSP activation Arrhenius integrals as a function of temperature and pulse duration.
Figure 28:
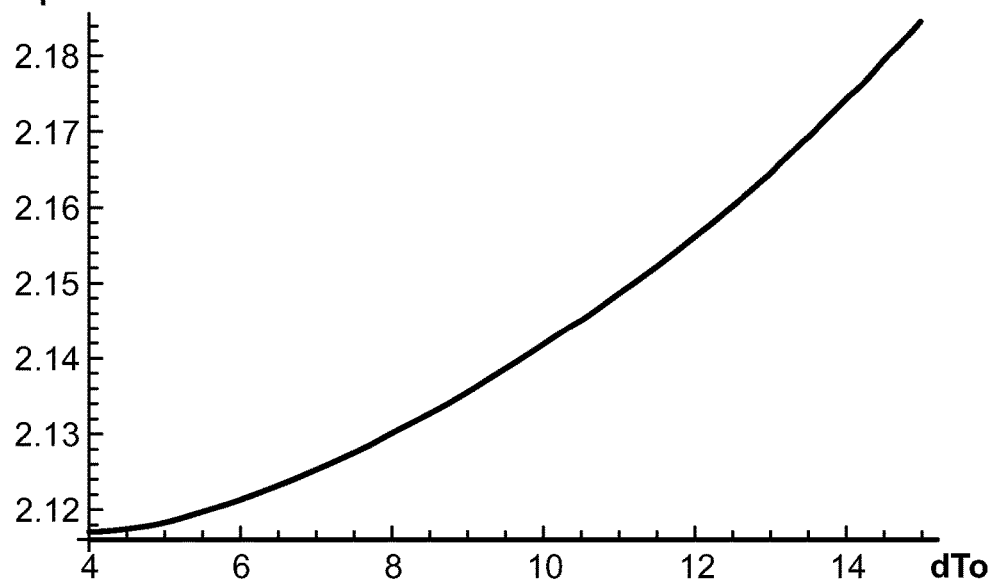

FIGS. 27 and 28 show the magnitude of the logarithm of the Arrhenius integrals for damage and for HSP activation or production as a function of $dT_o$ for a pulse duration $t_p=0.5$ sec, pulse interval $t_I=10$ sec, and total number of pulses N=10. Logarithm of Arrhenius integrals [eq. 12] for damage and for HSP activation as a function of the temperature rise in degrees Kelvin from a single pulse $dT_o$, for a pulse duration $t_p=0.5$ sec., pulse interval $t_I=10$ sec., and a total number of ultrasound pulses N=10. FIG. 27 shows the logarithm of the damage integral with the Arrhenius constants $A=8.71\times10^{33}$ sec$^{-1}$ and $E=3.55\times10^{-12}$ ergs. FIG. 28 shows the logarithm of the HSP activation integral with the Arrhenius constants $A=1.24\times10^{27}$ sec$^{-1}$ and $E=2.66\times10^{-12}$ ergs. The graphs in FIGS. 27 and 28 show that $\Omega_{damage}$ does not exceed 1 until $dT_o$ exceeds 11.3 K, whereas $\Omega_{hsp}$ is greater than 1 over the whole interval shown, the desired condition for cellular repair without damage.

Equation [8] shows that when $\alpha=0.1$ cm$^{-1}$, a $dT_o$ of 11.5 K can be achieved with a total ultrasound power of 5.8 watts. This is easily achievable. If a is increased by a factor of 2 or 3, the resulting power is still easily achievable. The volume of the region where the temperature rise is constant (i.e. the volume corresponding to $r=r_d=(4Dt_p)^{1/2}$) is 0.00064 cc. This corresponds to a cube that is 0.86 mm on a side.

This simple example demonstrates that focused ultrasound should be usable to stimulate reparative HSP's deep in the body with easily attainable equipment:

Total ultrasound power: 5.8 watts-17 watts
Pulse time 0.5 sec
Pulse interval 5 sec
Total train duration (N=10) 50 sec To expedite the treatment of larger internal volumes, a SAPRA system can be used.

The pulsed energy source may be directed to an exterior of a body which is adjacent to the target tissue or has a blood supply close to the surface of the exterior of the body. Alternatively, a device may be inserted into a cavity of a body to apply the pulsed energy source to the target tissue. Whether the energy source is applied outside of the body or inside of the body and what type of device is utilized depends upon the energy source selected and used to treat the target tissue.

Photostimulation, in accordance with the present invention, can be effectively transmitted to an internal surface area or tissue of the body utilizing an endoscope, such as a bronchoscope, proctoscope, colonoscope or the like. Each of these consist essentially of a flexible tube that itself contains one or more internal tubes. Typically, one of the internal tubes comprises a light pipe or multi-mode optical fiber which conducts light down the scope to illuminate the region of interest and enable the doctor to see what is at the illuminated end. Another internal tube could consist of wires that carry an electrical current to enable the doctor to cauterize the illuminated tissue. Yet another internal tube might consist of a biopsy tool that would enable the doctor to snip off and hold on to any of the illuminated tissue.

Figure 29:
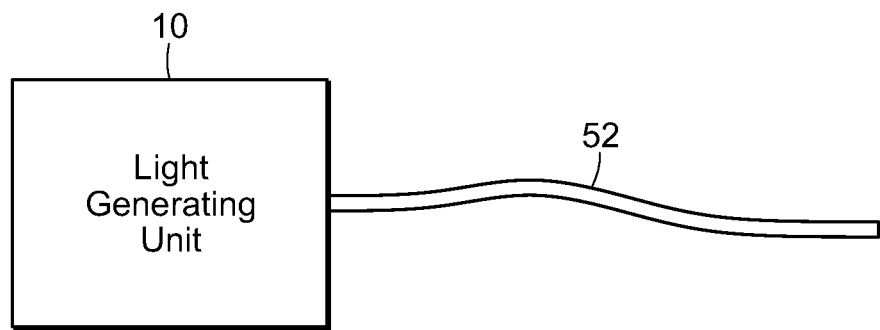
FIG. 29 is a diagrammatic view of a light generating unit that produces timed series of pulses, having a light pipe extending therefrom, in accordance with the present invention.
Figure 30:
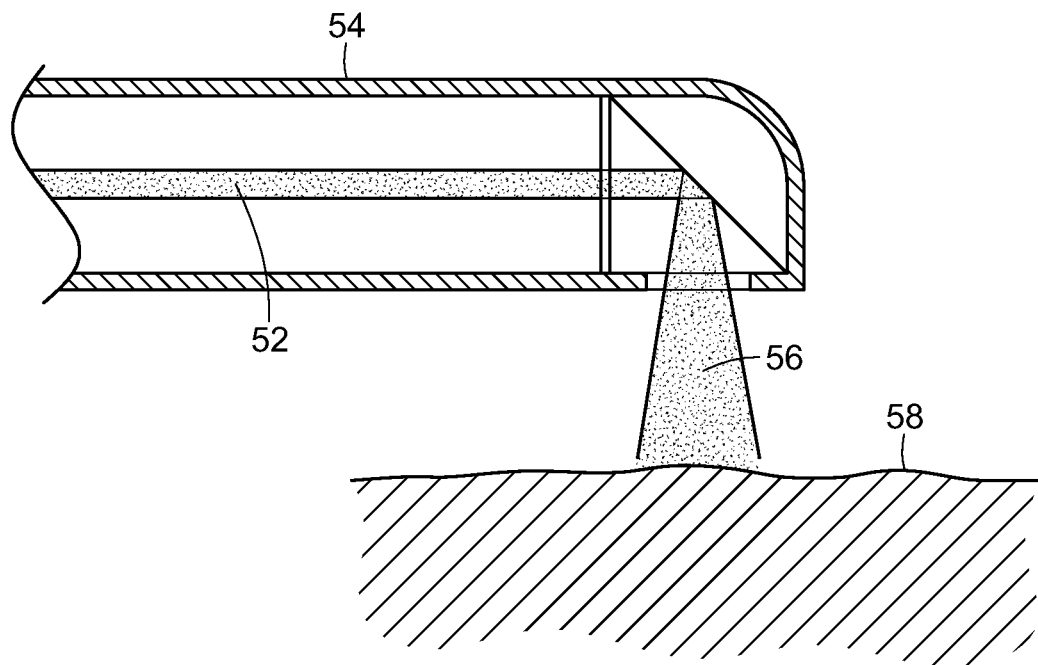
FIG. 30 is a cross-sectional view of a photostimulation delivery device delivering electromagnetic energy to target tissue, in accordance with the present invention.

In the present invention, one of these internal tubes is used as an electromagnetic radiation pipe, such as a multi-mode optical fiber, to transmit the SDM or other electromagnetic radiation pulses that are fed into the scope at the end that the doctor holds. With reference now to FIG. 29, a light generating unit 10, such as a laser having a desired wavelength and/or frequency is used to generate electromagnetic radiation, such as laser light, in a controlled, pulsed manner to be delivered through a light tube or pipe 52 to a distal end of the scope 54, illustrated in FIG. 30, which is inserted into the body and the laser light or other radiation 56 delivered to the target tissue 58 to be treated.

The light generator unit 10 of FIG. 29 could comprise the light generator units discussed above with respect to FIGS. 1-6. The delivery device or component, however could comprise an endoscope, bronchoscope, with the generated laser light beam passed through a light tube or pipe 52. The system could include both a laser beam projector or delivery device, such as a scope, as well as a viewing system/camera will comprise two different components in use. The viewing system/camera could provide feedback to a display monitor which may also include the necessary computerized hardware, data input and controls, for manipulating the optics, delivered laser light or other pulsed energy source and/or the projection/viewing components. Moreover, patterns can be generated which may be offset, as described above. Of course, the laser light generating systems of FIGS. 1-6 are exemplary, and other devices and systems can be utilized to generate a source of laser light or other pulsed electromagnetic radiation which can be operably passed through a projector device, such as the endoscope or light pipe or the like illustrated in FIGS. 29 and 30.

Other forms of electromagnetic radiation may also be generated and used, including ultraviolet waves, microwaves, other radiofrequency waves, and laser light at predetermined wavelengths. Moreover, ultrasound waves may also be generated and used to create a thermal time-course temperature spike in the target tissue sufficient to activate or produce heat shock proteins in the cells of the target tissue without damaging the target tissue itself. In order to do so, typically, a pulsed source of ultrasound or electromagnetic radiation energy is provided and applied to the target tissue in a manner which raises the target tissue temperature, such as between 6° C. and 11° C., transiently while only 6° C. or 1° C. or less for the long term, such as over several minutes.

For deep tissue that is not near an internal orifice, a light pipe is not an effective means of delivering the pulsed energy. In that case, pulsed low frequency electromagnetic energy or preferably pulsed ultrasound can be used to cause a series of temperature spikes in the target tissue.

Thus, in accordance with the present invention, a source of pulsed ultrasound or electromagnetic radiation is applied to the target tissue or fluid in order to stimulate HSP production or activation and to facilitate protein repair in the living animal tissue. In general, electromagnetic radiation may be ultraviolet waves, microwaves, other radiofrequency waves, laser light at predetermined wavelengths, etc. On the other hand, if electromagnetic energy is to be used for deep tissue targets away from natural orifices, absorption lengths restrict the wavelengths to those of microwaves or radiofrequency waves, depending on the depth of the target tissue. However, ultrasound is to be preferred to long wavelength electromagnetic radiation for deep tissue targets away from natural orifices.

The ultrasound or electromagnetic radiation is pulsed so as to create a thermal time-course in the tissue that stimulates HSP production or activation and facilitates protein repair without causing damage to the cells and tissue being treated. The area and/or volume of the treated tissue is also controlled and minimized so that the temperature spikes are on the order of several degrees, e.g. approximately 10° C., while maintaining the long-term rise in temperature to be less than the FDA mandated limit, such as 1° C. It has been found that if too large of an area or volume of tissue is treated, the increased temperature of the tissue cannot be diffused sufficiently quickly enough to meet the FDA requirements. However, limiting the area and/or volume of the treated tissue as well as creating a pulsed source of energy accomplishes the goals of the present invention of stimulating HSP activation or production by heating or otherwise stressing the cells and tissue, while allowing the treated cells and tissues to dissipate any excess heat generated to within acceptable limits.

Figure 31:
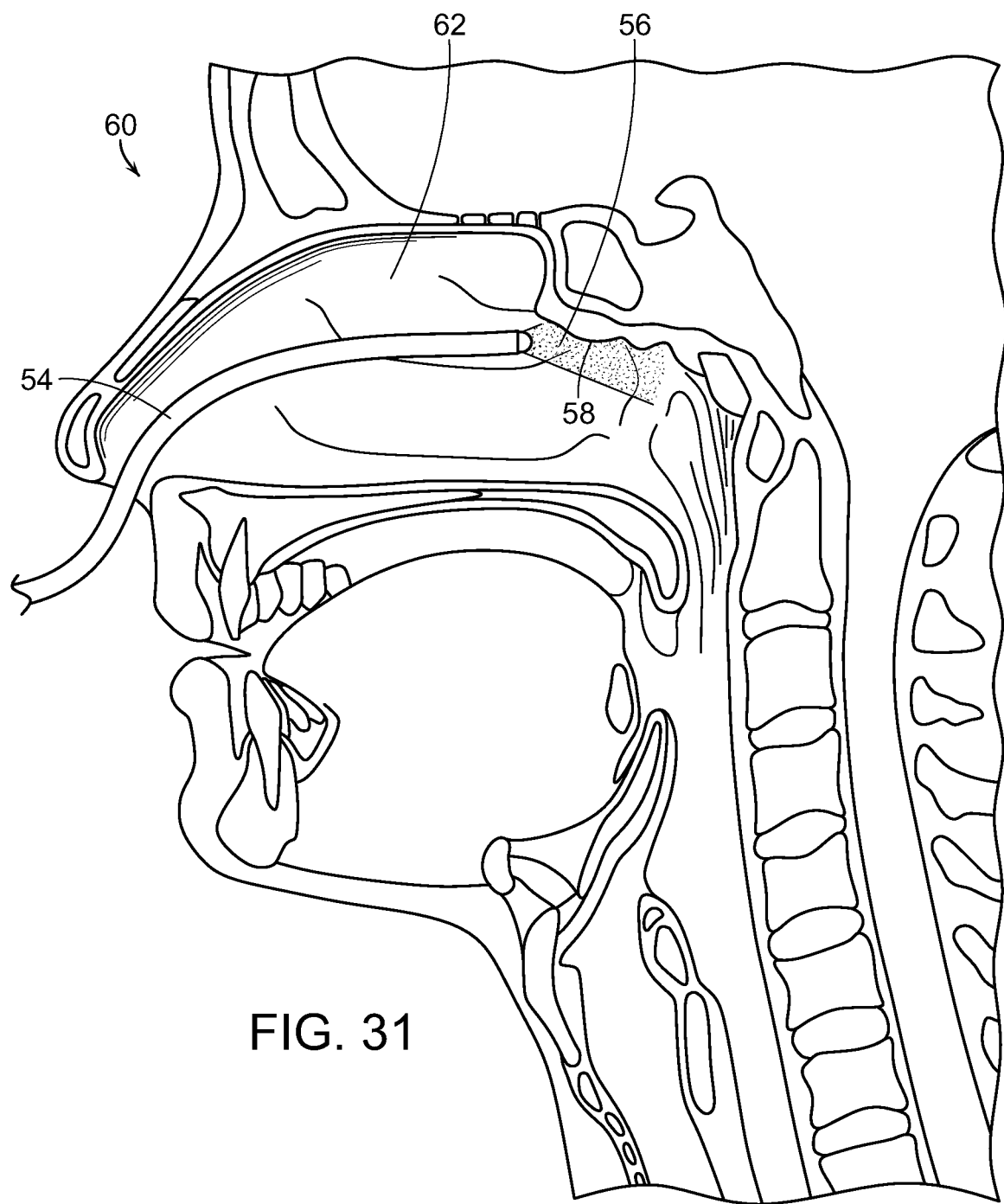
FIG. 31 is a cross-sectional and diagrammatic view of an end of an endoscope inserted into the nasal cavity and treating tissue therein, in accordance with the present invention.

It is believed that stimulating HSP production in accordance with the present invention can be effectively utilized in treating a wide array of tissue abnormalities, ailments, and even infections. For example, the viruses that cause colds primarily affect a small port of the respiratory epithelium in the nasal passages and nasopharynx. Similar to the retina, the respiratory epithelium is a thin and clear tissue. With reference to FIG. 31, a cross-sectional view of a human head 60 is shown with an endoscope 54 inserted into the nasal cavity 62 and energy 56, such as laser light or the like, being directed to tissue 58 to be treated within the nasal cavity 62. The tissue 58 to be treated could be within the nasal cavity 62, including the nasal passages, and nasopharynx.

To assure absorption of the laser energy, or other energy source, the wavelength can be adjusted to an infrared (IR) absorption peak of water, or an adjuvant dye can be used to serve as a photosensitizer. In such a case, treatment would then consist of drinking, or topically applying, the adjuvant, waiting a few minutes for the adjuvant to permeate the surface tissue, and then administering the laser light or other energy source 56 to the target tissue 58 for a few seconds, such as via optical fibers in an endoscope 54, as illustrated in FIG. 31. To provide comfort of the patient, the endoscope 54 could be inserted after application of a topical anesthetic. If necessary, the procedure could be repeated periodically, such as in a day or so.

The treatment would stimulate the activation or production of heat shock proteins and facilitate protein repair without damaging the cells and tissues being treated. As discussed above, certain heat shock proteins have been found to play an important role in the immune response as well as the well-being of the targeted cells and tissue. The source of energy could be monochromatic laser light, such as 810 nm wavelength laser light, administered in a manner similar to that described in the above-referenced patent applications, but administered through an endoscope or the like, as illustrated in FIG. 31. The adjuvant dye would be selected so as to increase the laser light absorption. While this comprises a particularly preferred method and embodiment of performing the invention, it will be appreciated that other types of energy and delivery means could be used to achieve the same objectives in accordance with the present invention.

Figure 32:
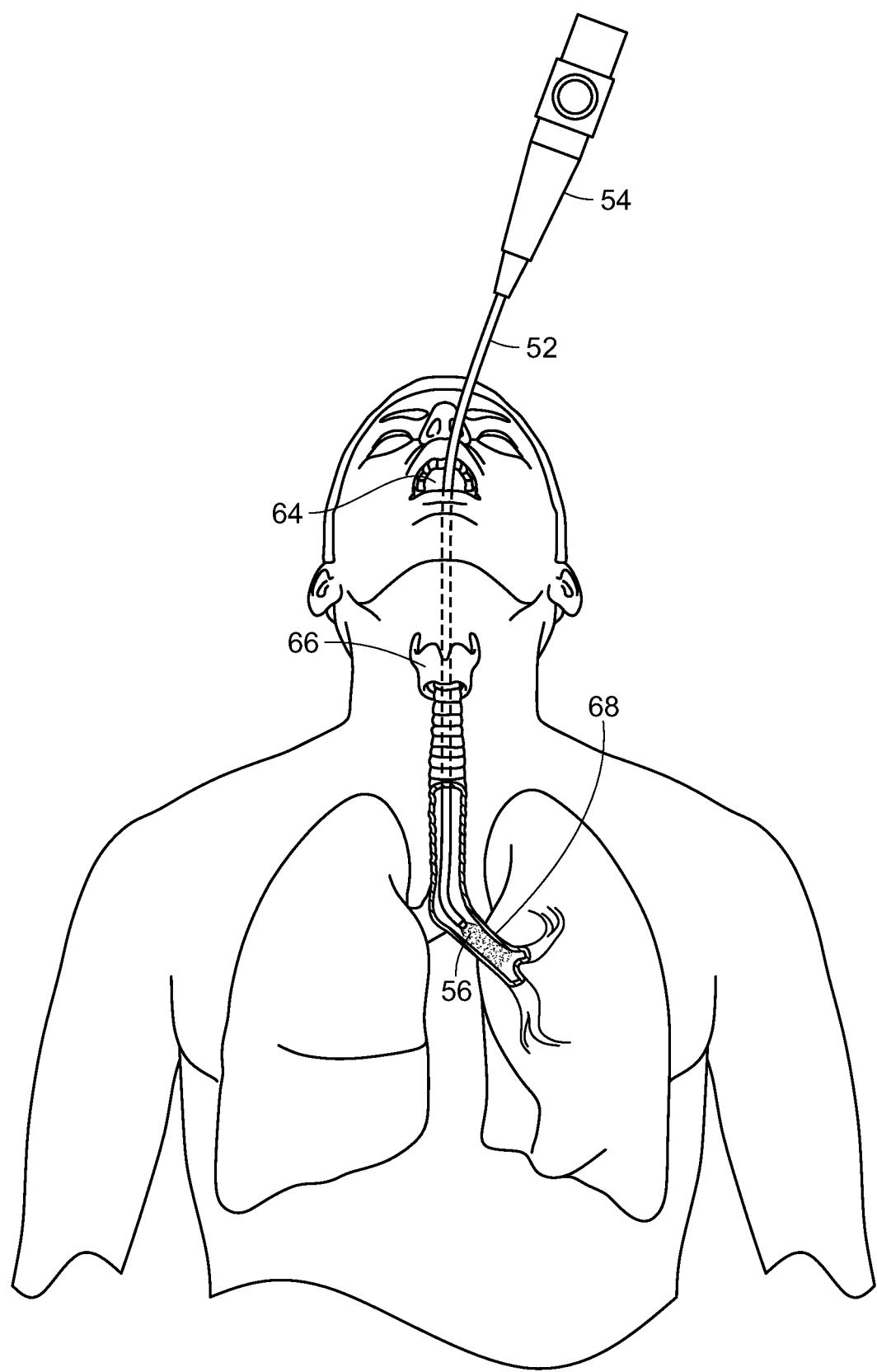
FIG. 32 is a diagrammatic and partially cross-sectioned view of a bronchoscope extending through the trachea and into the bronchus of a lung and providing treatment thereto, in accordance with the present invention.

With reference now to FIG. 32, a similar situation exists for other illnesses or diseases, where the primary target is the epithelium of the upper respiratory tree, in segments that have diameters greater than about 3.3 mm, namely, the upper six generations of the upper respiratory tree. A thin layer of mucous separates the targeted epithelial cells from the airway lumen, and it is in this layer that the antigen-antibody interactions occur that result in inactivation of viruses, such as cold and flu viruses.

With continuing reference to FIG. 32, the flexible light tube 52 of a bronchoscope 54 is inserted through the individual's mouth 64 through the throat and trachea 66 and into a bronchus 68 of the respiratory tree. There the laser light or other energy source 56 is administered and delivered to the tissue in this area of the uppermost segments to treat the tissue and area in the same manner described above with respect to FIG. 32. It is contemplated that a wavelength of laser or other energy would be selected so as to match an IR absorption peak of the water resident in the mucous to heat the tissue and stimulate HSP activation or production and facilitate protein repair, with its attendant benefits.

Figure 33:
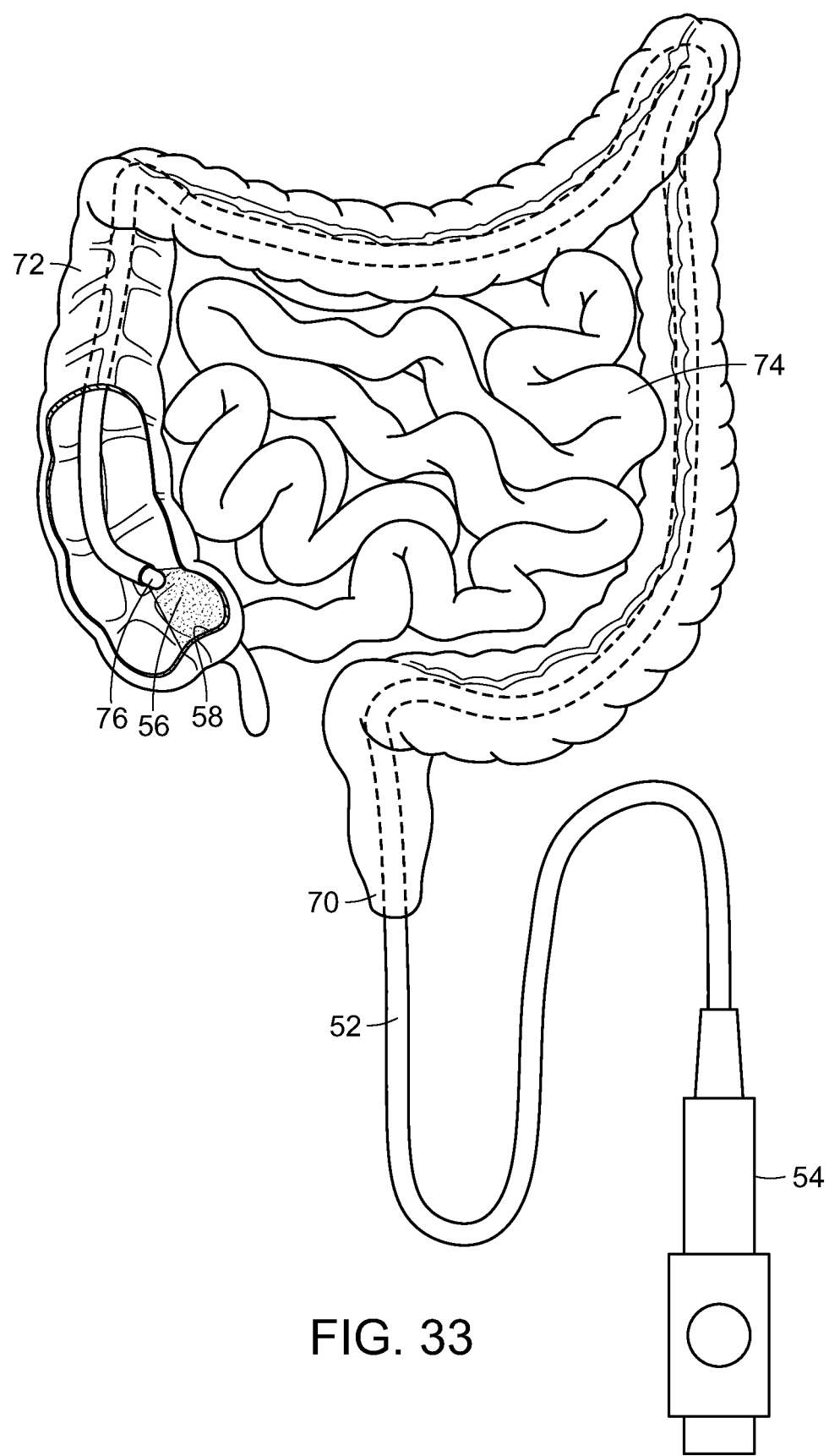
FIG. 33 is a diagrammatic view of a colonoscope providing photostimulation to an intestinal or colon area of the body, in accordance with the present invention.

With reference now to FIG. 33, a colonoscope 54 could have flexible optical tube 52 thereof inserted into the anus and rectum 70 and into either the large intestine 72 or small intestine 74 so as to deliver the selected laser light or other energy source 56 to the area and tissue to be treated, as illustrated. This could be used to assist in treating colon cancer as well as other gastrointestinal issues.

Typically, the procedure could be performed similar to a colonoscopy in that the bowel would be cleared of all stool, and the patient would lie on his/her side and the physician would insert the long, thin light tube portion 52 of the colonoscope 54 into the rectum and move it into the area of the colon, large intestine 72 or small intestine 74 to the area to be treated. The physician could view through a monitor the pathway of the inserted flexible member 52 and even view the tissue at the tip of the colonoscope 54 within the intestine, so as to view the area to be treated. Using one of the other fiber optic or light tubes, the tip 76 of the scope would be directed to the tissue to be treated and the source of laser light or other radiation 56 would be delivered through one of the light tubes of the colonoscope 54 to treat the area of tissue to be treated, as described above, in order to stimulate HSP activation or production in that tissue 58.

Figure 34:
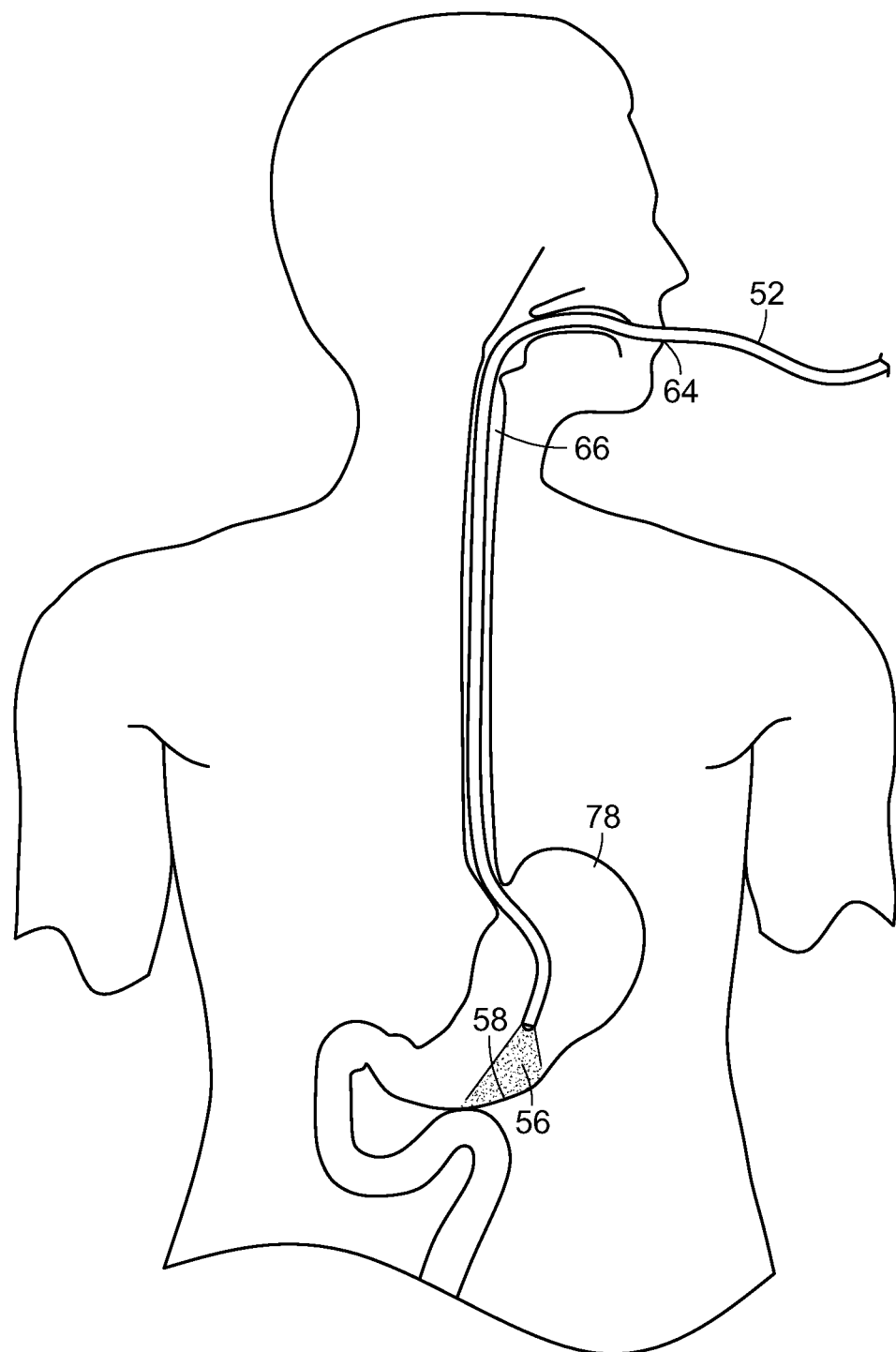
FIG. 34 is a diagrammatic view of an endoscope inserted into a stomach and providing treatment thereto, in accordance with the present invention.

With reference now to FIG. 34, another example in which the present invention can be advantageously used in the GI tract, for example what is frequently referred to as "leaky gut" syndrome, a condition of the gastrointestinal (GI) tract marked by inflammation and other metabolic dysfunction. Since the GI tract is susceptible to metabolic dysfunction similar to the retina, it is anticipated that it will respond well to the treatment of the present invention. This could be done by means of subthreshold, diode micropulsed laser (SDM) treatment, as discussed above, or by other energy sources and means as discussed herein and known in the art.

With continuing reference to FIG. 34, the flexible light tube 52 of an endoscope or the like is inserted through the patient's mouth 64 through the throat and trachea area 66 and into the stomach 78, where the tip or end 64 thereof is directed towards the tissue 58 to be treated, and the laser light or other energy source 56 is directed to the tissue 58. It will be appreciated by those skilled in the art that a colonoscope could also be used and inserted through the rectum 70 and into the stomach 78 or any tissue between the stomach and the rectum.

If necessary, a chromophore pigment could be delivered to the GI tissue orally to enable absorption of the radiation. If, for instance, unfocused 810 nm radiation from a laser diode or LED were to be used, the pigment would have an absorption peak at or near 810 nm. Alternatively, the wavelength of the energy source could be adjusted to a slightly longer wavelength at an absorption peak of water, so that no externally applied chromophore would be required.

Figure 35:
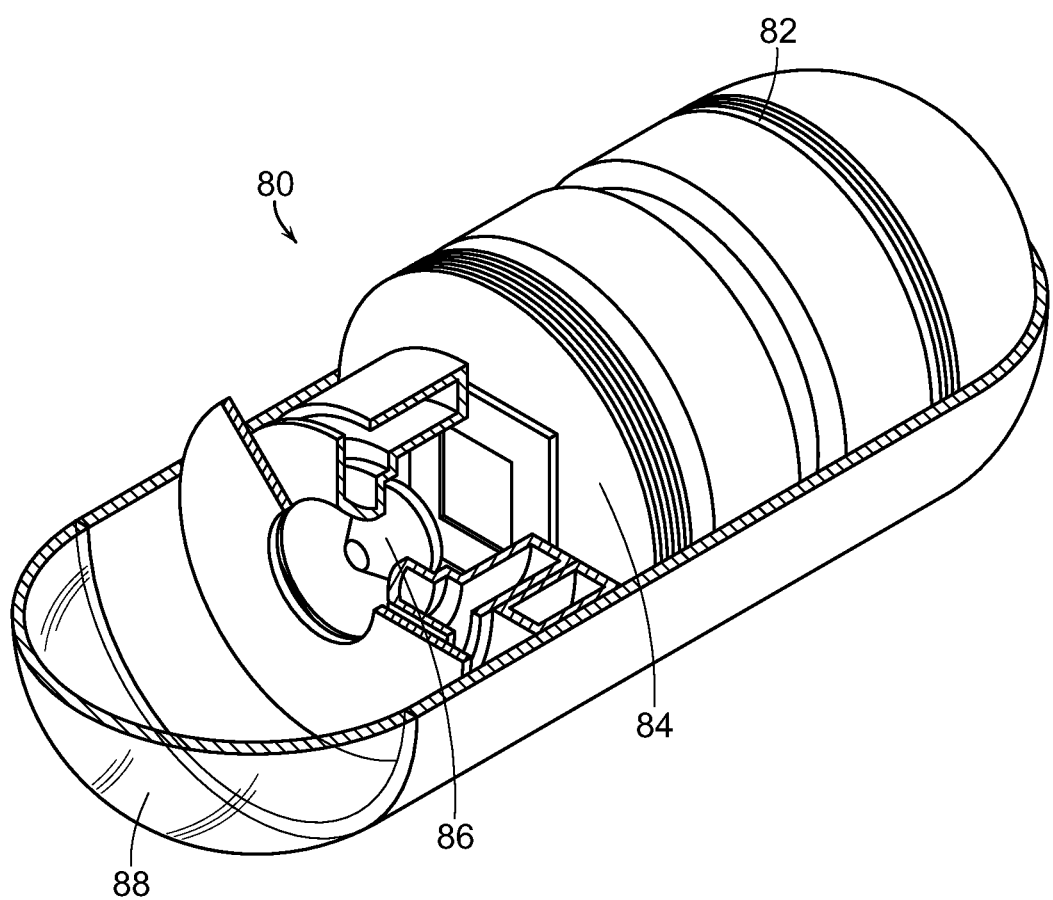
FIG. 35 is a partially sectioned perspective view of a capsule endoscope, used in accordance with the present invention.

It is also contemplated by the present invention that a capsule endoscope 80, such as that illustrated in FIG. 35, could be used to administer the radiation and energy source in accordance with the present invention. Such capsules are relatively small in size, such as approximately one inch in length, so as to be swallowed by the patient. As the capsule or pill 80 is swallowed and enters into the stomach and passes through the GI tract, when at the appropriate location, the capsule or pill 80 could receive power and signals, such as via antenna 82, so as to activate the source of energy 84, such as a laser diode and related circuitry, with an appropriate lens 86 focusing the generated laser light or radiation through a radiation-transparent cover 88 and onto the tissue to be treated. It will be understood that the location of the capsule endoscope 80 could be determined by a variety of means such as external imaging, signal tracking, or even by means of a miniature camera with lights through which the doctor would view images of the GI tract through which the pill or capsule 80 was passing through at the time. The capsule or pill 80 could be supplied with its own power source, such as by virtue of a battery, or could be powered externally via an antenna, such that the laser diode 84 or other energy generating source create the desired wavelength and pulsed energy source to treat the tissue and area to be treated.

As in the treatment of the retina in previous applications, the radiation would be pulsed to take advantage of the micropulse temperature spikes and associated safety, and the power could be adjusted so that the treatment would be completely harmless to the tissue. This could involve adjusting the peak power, pulse times, and repetition rate to give spike temperature rises on the order of 10° C., while maintaining the long term rise in temperature to be less than the FDA mandated limit of 1° C. If the pill form 80 of delivery is used, the device could be powered by a small rechargeable battery or over wireless inductive excitation or the like. The heated/stressed tissue would stimulate activation or production of HSP and facilitate protein repair, and the attendant benefits thereof.

From the foregoing examples, the technique of the present invention is limited to the treatment of conditions at near body surfaces or at internal surfaces easily accessible by means of fiber optics or other optical delivery means. The reason that the application of SDM or PEMR to activate HSP activity is limited to near surface or optically accessibly regions of the body is that the absorption length of IR or visible radiation in the body is very short. However, there are conditions deeper within tissue or the body which could benefit from the present invention. Thus, the present invention contemplates the use of ultrasound and/or radio frequency (RF) and even shorter wavelength electromagnetic (EM) radiation such as microwave which have relatively long absorption lengths in body tissue. The use of pulsed ultrasound is often preferable to RF electromagnetic radiation to activate remedial HSP activity in abnormal tissue that is inaccessible to surface SDM or the like. Pulsed ultrasound sources can also be used for abnormalities at or near surfaces as well.

Figure 36:
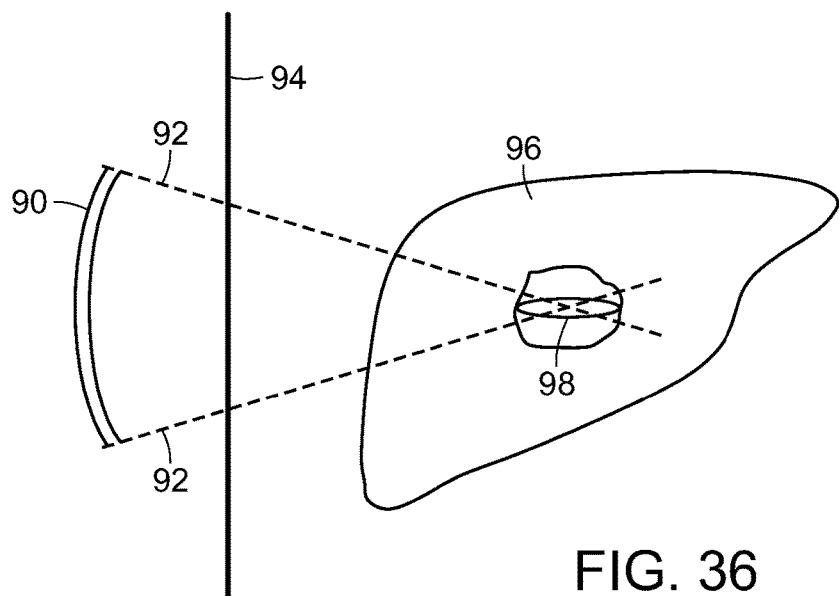
FIG. 36 is a diagrammatic view of a pulsed high intensity focused ultrasound for treating tissue internal the body, in accordance with the present invention.

With reference now to FIG. 36, with ultrasound, microwave or RF, a specific region deep in the body can be specifically targeted by using one or more beams that are each focused on the target site. The pulsating heating will then be largely only in the targeted region where the beams are focused and overlap.

As illustrated in FIG. 36, an ultrasound transducer 90 or the like generates a plurality of ultrasound beams 92 which are coupled to the skin via an acoustic-impedance-matching gel, and penetrate through the skin 94 and through undamaged tissue in front of the focus of the beams 92 to a target organ 96, such as the illustrated liver, and specifically to a target tissue 98 to be treated where the ultrasound beams 92 are focused. As mentioned above, the pulsating heating will then only be at the targeted, focused region 98 where the focused beams 92 overlap. The tissue in front of and behind the focused region 98 will not be heated or affected appreciably.

The present invention contemplates not only the treatment of surface or near surface tissue, such as using the laser light or the like, deep tissue using, for example, focused ultrasound RF, or microwave beams or the like, but also treatment of blood diseases, and other bodily fluid diseases, such as sepsis. As indicated above, focused ultrasound treatment could be used both at surface as well as deep body tissue, and could also be applied in this case in treating blood. However, it is also contemplated that the SDM and similar PEMR treatment options which are typically limited to surface or near surface treatment of epithelial cells and the like be used in treating blood or fluid diseases at areas where the blood or fluid is accessible through a relatively thin layer of tissue, such as the earlobe.

Figure 37:
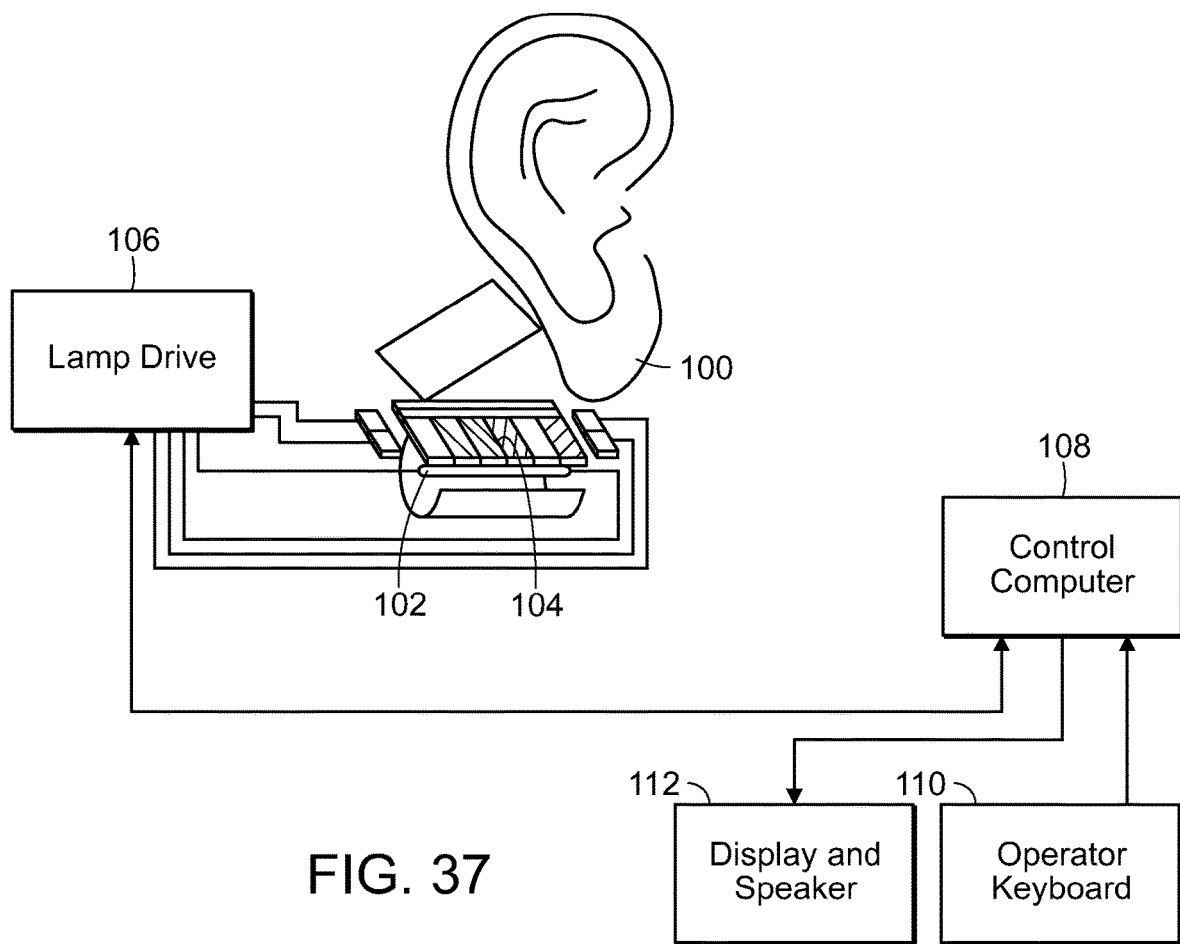
FIG. 37 is a diagrammatic view for delivering therapy to the bloodstream of a patient, through an earlobe, in accordance with the present invention.
Figure 38:
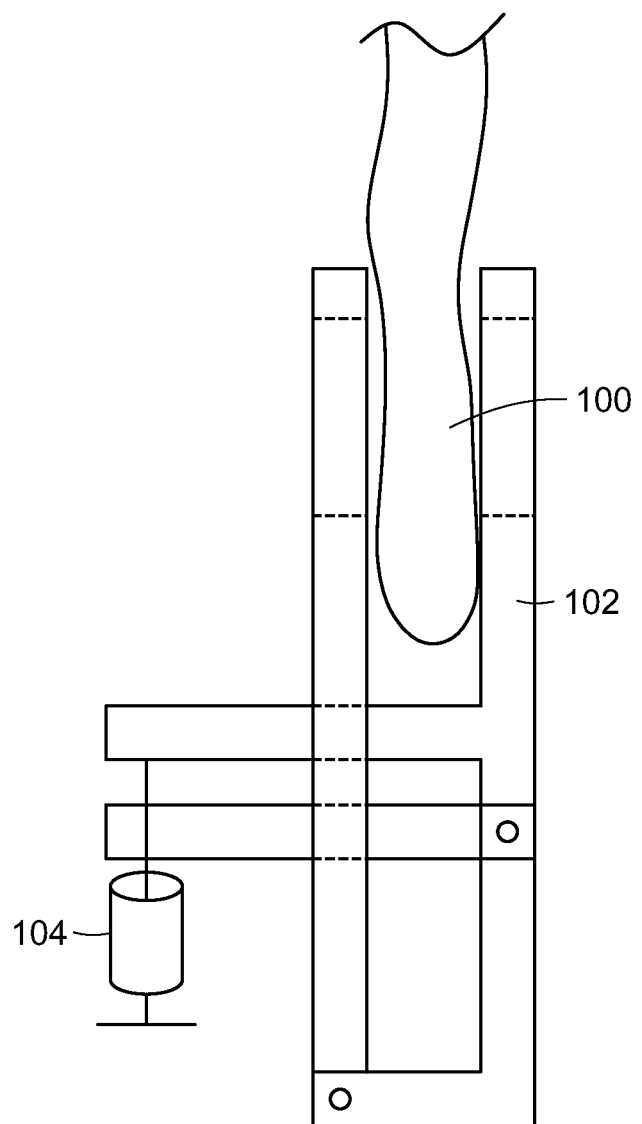
FIG. 38 is a cross-sectional view of a stimulating therapy device of the present invention used in delivering photostimulation to the blood, via an earlobe, in accordance with the present invention.

With reference now to FIGS. 37 and 38, treatment of blood disorders simply requires the transmission of SDM or other electromagnetic radiation or ultrasound pulses to the earlobe 100, where the SDM or other radiation source of energy could pass through the earlobe tissue and into the blood which passes through the earlobe. It would be appreciated that this approach could also take place at other areas of the body where the blood flow is relatively high and/or near the tissue surface, such as fingertips, inside of the mouth or throat, etc.

With reference again to FIGS. 37 and 38, an earlobe 100 is shown adjacent to a clamp device 102 configured to transmit SDM radiation or the like. This could be, for example, by means of one or more laser diodes 104 which would transmit the desired frequency at the desired pulse and pulse train to the earlobe 100. Power could be provided, for example, by means of a lamp drive 106. Alternatively, the lamp drive 106 could be the actual source of laser light, which would be transmitted through the appropriate optics and electronics to the earlobe 100. The clamp device 102 would merely be used to clamp onto the patient's earlobe and cause that the radiation be constrained to the patient's earlobe 100. This may be by means of mirrors, reflectors, diffusers, etc. This could be controlled by a control computer 108, which would be operated by a keyboard 110 or the like. The system may also include a display and speakers 112, if needed, for example if the procedure were to be performed by an operator at a distance from the patient.

As mentioned above, although FIGS. 37 and 38 illustrate, for exemplary purposes, the treatment of a bodily fluid, namely blood, through a readily accessible external earlobe 100, it will be appreciated that the pulsed energy source of the present invention can be applied to other external areas of the body, internal areas of the body, and utilize a wide variety of energy sources, including laser light, radiofrequency, microwave, and ultrasound. Moreover, the present invention is not only limited to the treatment of blood and blood diseases, but can also be applied to other bodily fluids, such as lymph fluid, etc. The type of bodily fluid treated may dictate the area where the treatment occurs, such as applying the energy source in an armpit, tonsil, etc. when treating lymph fluid.

Although not specifically described above, it will be appreciated that various diseases or potential diseases could be treated in various areas of the body, depending upon the disease and the target tissue to be treated either for treatment purposes or for prophylactic or protective therapy. For example, IPF may be treated by PEMR infrared laser locally via bronchoscopic application. Heart disease, due to the heart being located near the bronchial tree and lungs, could also be treated via bronchoscopy. Alternatively, as infrared absorption lengths are small, as indicated above, PEMR radiofrequency, ultrasound or microwave may be used to treat the heart, lungs, etc. An additional advantage would be not requiring the discomfort of a bronchoscope being inserted into the lungs of the patient.

Once again, the selected treatment type and operating procedure and parameters could change depending upon the location of the chronic progressive disease. For example, Alzheimer disease may be treated by RF application to the brain. A person having cancer, or a risk for cancer, could have the energy source in accordance with the present invention applied to the organ(s) or area of the body in question, whether it be a tissue or blood (generally not the cancer itself, as activation of HSPs in cancer cells may enhance the survival and growth of the cancer; but to treat components of the immune system to enhance their effectiveness against the cancer). Even mental conditions, such as depression, could potentially be treated in accordance with the present invention.

The present invention also contemplates that the time course, and possibly powers, and other energy and operating parameters may need to be changed depending upon the tissue, organ, or area of the body to be treated. For example, for idiopathic pulmonary fibrosis and other lung diseases, such parameters may need to be changed due to the convective air flow which can cool the lung tissue. Having the individual exhale and hold his or her breath for a couple of seconds can also alter these energy parameters as an inflated lung has a conductivity of 0.2 S/m while a deflated lung has a conductivity twice as large, 0.41 S/m, and the absorption length is inversely proportional to the square root of the conductivity. The important aspect is that the tissue or bodily fluid is heated very quickly up to approximately 11° C. while maintaining a much lower temperature, such as below 6° C. or even 1° C. over several minutes, such as 6 minutes. This will provide the therapeutic benefit, such as activating HSPs, while not damaging the bodily fluid, cells and tissue.

Figure 39:
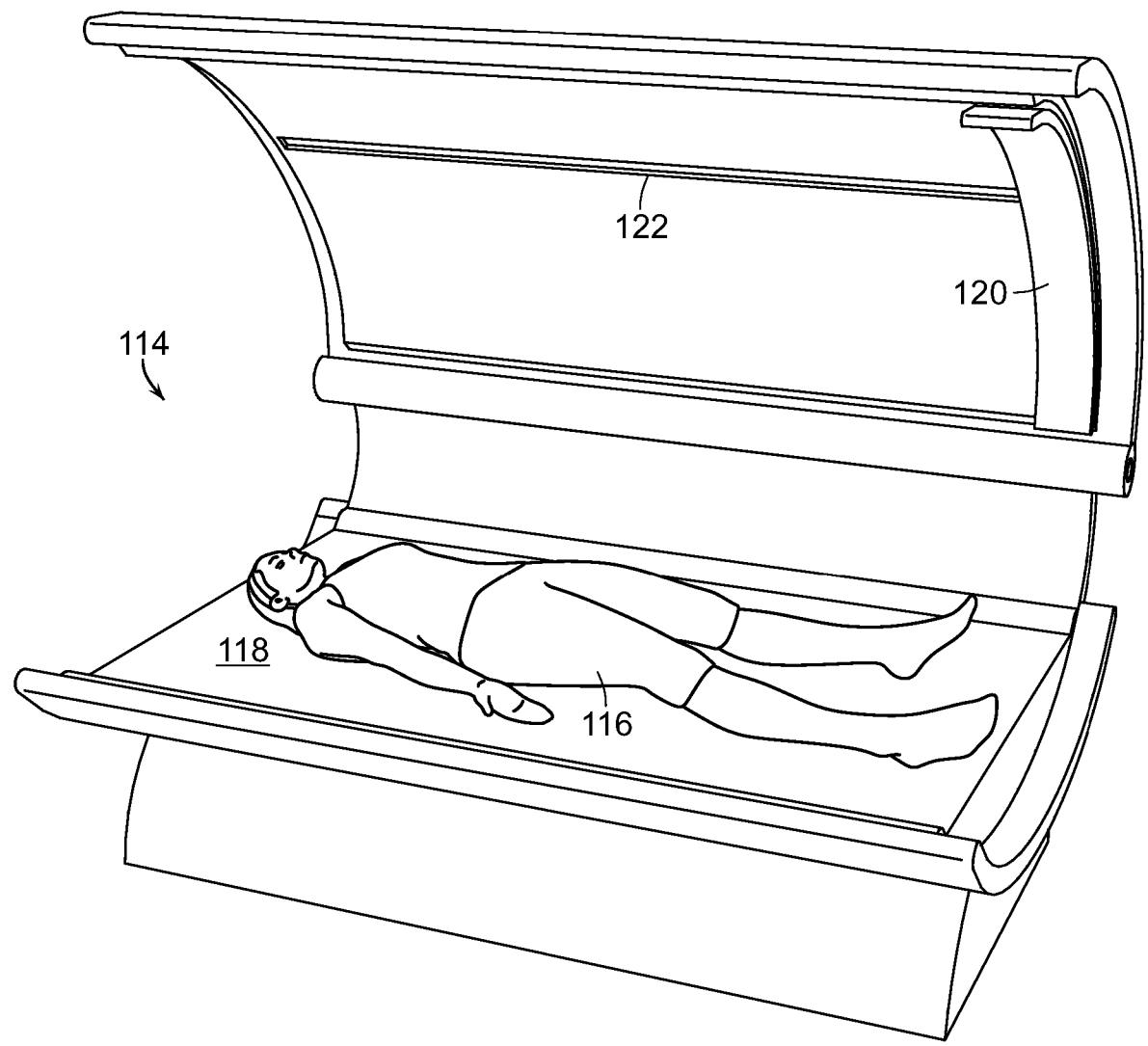
FIG. 39 is a diagrammatic and perspective view of a device for treating multiple areas or an entire body of an individual, in accordance with the present invention.

With reference now to FIG. 39, it is contemplated by the present invention that some diseases or risk of diseases may require treatment of multiple areas of the body. For example, diabetes may be treated by microwave, RF application or the like to many areas of the body, and potentially the entire body. Also, the individual may either have multiple chronic progressive diseases or may be at a risk of having multiple chronic progressive diseases which could require treatment of various areas of the body. Furthermore, since the process of treatment in accordance with the present invention appears to have only beneficial therapeutic and protective consequences, without permanently damaging or destroying cells or tissue, the entire body could be treated as healthy cells and tissue would not be negatively impacted by the application of the pulsed energy source applied in accordance with the present invention while those that are damaged would be benefitted.

Accordingly, with continuing reference to FIG. 39, a device 114 is contemplated by the present invention which can hold and/or support an entire body 116, such as by means of a platform 118 upon which the individual lies. It will be understood, however, that the individual could be in different positions, such as standing, and not necessarily need to lie down. The device 114 would include a pulsed energy emitter 120 which could emit a pulsed energy source having the parameters discussed above so as to treat various types of tissue, organs, bodily fluids, etc. of the individual. This could be, for example, by means of microwave, radiofrequency (RF) and/or ultrasound, or even light sources used to treat external portions of the individual's body or bodily fluids passing adjacent to such surfaces. The fluid, organs in question or other tissue could be treated accordingly. In fact, as mentioned above, the entire body could be treated as the emitter 120 is moved, such as along track 122, to different areas of the body, either progressively or in a predetermined pattern, in such a manner so as to fairly quickly treat the desired areas of target tissue or target bodily fluid and/or the entire body by heating up the areas to the predetermined temperature while maintaining the predetermined lower temperature over a more prolonged period of time. The whole body treatment could be a sum of the localized treatments. This could be a way, for example, to treat diabetes and other similar diseases which affect the entire body or multiple areas of the body. This could also be, for example, a system and method for protectively and prophylactically treating the whole body of an individual, such as on a period basis.

The proposed treatment with a train of electromagnetic or ultrasound pulses has two major advantages over earlier treatments that incorporate a single short or sustained (long) pulse. First, the short (preferably subsecond) individual pulses in the train activate cellular reset mechanisms like HSP activation with larger reaction rate constants than those operating at longer (minute or hour) time scales. Secondly, the repeated pulses in the treatment provide large thermal spikes (on the order of 10,000) that allow the cell's repair system to more rapidly surmount the activation energy barrier that separates a dysfunctional cellular state from the desired functional state. The net result is a "lowered therapeutic threshold" in the sense that a lower applied average power and total applied energy can be used to achieve the desired treatment goal.

Although several embodiments have been described in detail for purposes of illustration, various modifications may be made without departing from the scope and spirit of the invention. Accordingly, the invention is not to be limited, except as by the appended claims.

What is claimed is:

1. A process for treating biological tissue or fluid having, or a risk of having, a chronic progressive disease, comprising the steps of:
    providing a pulsed energy source having energy parameters including wavelength or frequency, duty cycle and pulse train duration; and
    applying the pulsed energy source to a target tissue or a target fluid having a chronic progressive disease or a risk of having a chronic progressive disease for the pulse train duration comprising less than one second to therapeutically treat the diseased target tissue or target fluid or prophylactically treat the target tissue or target fluid to prevent disease in the target tissue or target fluid;
    wherein the pulsed energy source energy parameters are selected and the pulsed energy applied to the target tissue or target fluid so that the target tissue or the target fluid temperature is raised between six degrees Celsius to eleven degrees Celsius at least during application of the pulsed energy source to the target tissue or target fluid, but the target tissue or target fluid temperature several minutes after application of the pulsed energy source is only raised one degree Celsius or less to achieve a therapeutic or prophylactic effect while not permanently damaging the target tissue or target fluid; and
    wherein the applying the pulsed energy source step comprises inserting a device into a cavity of a body to apply the pulsed energy source to the target tissue or target fluid.

2. The process of claim 1, wherein the applying step comprises the step of stimulating heat shock protein activation in the target tissue or target fluid.

3. The process of claim 1, wherein after a six minute period of time from the application of the pulsed energy source, the temperature of the target tissue or target fluid is raised one degree Celsius or less.

4. The process of claim 1, wherein the pulsed energy source energy parameters are selected so that 20 to 40 joules of energy is absorbed by each cubic centimeter of the target tissue or target fluid.

5. The process of claim 1, including the step of determining that the target tissue or target fluid has a chronic progressive disease or is at risk of having a chronic progressive disease.

6. The process of claim 1, wherein the pulsed energy source is applied to a plurality of target tissue areas, and wherein adjacent target tissue areas are separated by at least a predetermined distance to avoid thermal tissue damage.

7. The process of claim 6, wherein the applying the pulsed energy step comprises directing the pulsed energy source to an exterior of a body which is adjacent to the target tissue or has a target bodily fluid supply close to the surface of the exterior area of the body.

8. The process of claim 6, wherein the pulsed energy is shifted and applied to the target tissue until the pulsed energy has been applied to all of the target tissue.

9. A process for treating biological tissue or fluid having, or a risk of having, a chronic progressive disease, comprising the steps of:
    providing a pulsed energy source having energy parameters including wavelength or frequency, duty cycle and pulse train duration; and
    applying the pulsed energy source to a target tissue or a target fluid having a chronic progressive disease or a risk of having a chronic progressive disease for the pulse train duration comprising less than one second to therapeutically treat the diseased target tissue or target fluid or prophylactically treat the target tissue or target fluid to prevent disease in the target tissue or target fluid; and
    wherein the pulsed energy source energy parameters are selected and the pulsed energy applied to the target tissue or target fluid so that the target tissue or the target fluid temperature is raised between six degrees Celsius to eleven degrees Celsius at least during application of the pulsed energy source to the target tissue or target fluid, but the target tissue or target fluid temperature several minutes after application of the pulsed energy source is only raised one degree Celsius or less to achieve a therapeutic or prophylactic effect while not permanently damaging the target tissue or target fluid; and
    wherein the pulsed energy source comprises a radio frequency.

10. The process of claim 9, wherein the pulsed energy source comprises a radio frequency between three to six megahertz, a duty cycle between 2.5% to 5%, and a pulse train duration between 0.2 to 0.4 seconds.

11. The process of claim 10, wherein the radio frequency is generated with a device having a coil radii between 2 and 6 mm and between 13 and 57 amp turns.

12. A process for treating providing protective therapy for biological tissue or fluid having, or a risk of or having, a chronic progressive disease, comprising the steps of:
    determining that a target tissue or target bodily fluid has a chronic progressive disease or is at risk of having a chronic progressive disease;
    providing a radio frequency pulsed energy source having energy parameters including wavelength or frequency, duty cycle and pulse train duration; and
    applying the pulsed energy source to the target tissue or the target fluid determined to have a chronic progressive disease or a risk of having a chronic progressive disease for the pulse train duration comprising less than one second to therapeutically treat the diseased target tissue or target fluid or prophylactically treat the target tissue or target fluid to prevent disease in the target tissue or target fluid;
    wherein the energy parameters are selected and the pulsed energy applied to the target tissue or target bodily fluid so as to raise a target tissue or bodily target fluid temperature between six and eleven degrees Celsius at least during application of the pulsed energy to achieve a therapeutic or prophylactic effect but the average temperature rise of the target tissue or target fluid over several minutes is maintained at or below one degree Celsius so as to not permanently damage the target tissue or target bodily fluid; and
    wherein the pulsed energy source comprises a radio frequency between three to six megahertz, a duty cycle between 2.5% to 5%, and a pulse train duration between 0.2 to 0.4 seconds.

13. The process of claim 12, wherein the applying step comprises the step of stimulating heat shock protein activation in the target tissue or target fluid.

14. The process of claim 12, wherein the average temperature of the target tissue or target fluid is maintained at one degree Celsius or less over a six minute period of time.

15. The process of claim 12, wherein the pulsed energy source energy parameters are selected so that 20 to 40 joules of energy is absorbed by each cubic centimeter of the target tissue or target fluid.

16. The process of claim 12, wherein the applying the pulsed energy source step comprises inserting a device into a cavity of a body to apply the pulsed energy source to the target tissue or target fluid.

17. The process of claim 12, wherein the applying the pulsed energy step comprises directing the pulsed energy source to an exterior of a body which is adjacent to the target tissue or has a target bodily fluid supply close to the surface of the exterior area of the body.

18. The process of claim 12, wherein the pulsed energy source is applied to a plurality of target tissue areas, and wherein adjacent target tissue areas are separated by at least a predetermined distance to avoid thermal tissue damage.

19. The process of claim 18, wherein the pulsed energy is shifted and applied to the target tissue until the pulsed energy has been applied to all of the target tissue.

20. The process of claim 12, wherein the radio frequency is generated with a device having a coil radii between 2 and 6 mm and between 13 and 57 amp turns.

\* \* \* \* \*